(12) United States Patent
Theopold et al.

(10) Patent No.: US 6,511,936 B1
(45) Date of Patent: Jan. 28, 2003

(54) CATALYST COMPOUNDS WITH β-DIMINATE ANIONIC LIGANDS AND PROCESSES FOR POLYMERIZING OLEFINS

(75) Inventors: Klaus H. Theopold, Newark, DE (US); Woo-Kyu Kim, Bridgewater, NJ (US); Leonard A. MacAdams, Newark, DE (US); John M. Power, Kingwood, TX (US); Javier M. Mora, Houston, TX (US); Albert P. Masino, Kingwood, TX (US)

(73) Assignees: University of Delaware, Newark, DE (US); Chevron Chemical Co., San Francisco, CA (US)

( * ) Notice: Subject to any disclaimer, the term of this patent is extended or adjusted under 35 U.S.C. 154(b) by 0 days.

(21) Appl. No.: 09/373,729

(22) Filed: Aug. 13, 1999

Related U.S. Application Data

(63) Continuation-in-part of application No. 09/022,414, filed on Feb. 12, 1998, now abandoned.

(51) Int. Cl.[7] .................... B01J 31/00; C08F 4/06; C07F 9/00; C07F 17/00; C07F 13/00

(52) U.S. Cl. .................. 502/167; 526/172; 556/32; 556/42; 556/43; 556/45; 556/46; 556/51; 556/52; 556/57; 556/58; 556/137; 556/138; 556/140; 556/410; 556/424

(58) Field of Search .................. 502/123, 167; 556/32, 39, 43, 46, 52, 58, 413, 424, 42, 45, 51, 57, 137, 138, 140, 410; 526/172

(56) References Cited

U.S. PATENT DOCUMENTS

| | | | |
|---|---|---|---|
| 4,960,747 A | 10/1990 | Van Doorn et al. | 502/167 |
| 4,994,534 A * | 2/1991 | Rhee et al. | 526/88 |
| 5,055,438 A | 10/1991 | Canich | 502/117 |
| 5,075,394 A * | 12/1991 | McDaniel et al. | 502/103 |
| 5,075,426 A * | 12/1991 | Zielinski | 534/15 |
| 5,177,253 A | 1/1993 | Drent et al. | 560/207 |
| 5,179,225 A | 1/1993 | Drent et al. | 560/207 |
| 5,304,588 A * | 4/1994 | Boysen et al. | 523/204 |
| 5,399,636 A | 3/1995 | Alt et al. | 526/129 |
| 5,418,200 A | 5/1995 | Carney et al. | 502/117 |
| 5,420,320 A | 5/1995 | Zenk et al. | 556/43 |
| 5,434,116 A | 7/1995 | Sone et al. | 502/103 |
| 5,495,036 A * | 2/1996 | Wilson et al. | 502/117 |
| 5,516,739 A | 5/1996 | Barborak et al. | 502/161 |
| 5,554,777 A | 9/1996 | Hefner et al. | 556/21 |
| 5,561,216 A | 10/1996 | Barborak et al. | 528/392 |
| 5,565,547 A | 10/1996 | Hefner et al. | 528/392 |
| 5,587,439 A | 12/1996 | DiMaio | 526/142 |
| 5,589,556 A | 12/1996 | Razavi | 526/170 |
| 5,594,080 A | 1/1997 | Waymouth et al. | 526/126 |
| 5,714,556 A | 2/1998 | Johnson et al. | 526/135 |
| 5,777,050 A | 7/1998 | Friederichs et al. | 526/123.1 |
| 5,817,849 A * | 10/1998 | Wilson et al. | 502/103 |
| 6,069,237 A * | 5/2000 | Ewen et al. | 534/15 |
| 6,127,497 A * | 10/2000 | Matsunaga et al. | 526/141 |
| 6,228,794 B1 * | 5/2001 | Jordan et al. | 502/155 |

FOREIGN PATENT DOCUMENTS

| | | | | |
|---|---|---|---|---|
| DE | 4202889 | * | 8/1993 | 211/65 |
| EP | 0803520 | | 10/1997 | |
| WO | WO 9748736 | * | 8/1993 | 4/80 |
| WO | WO 95/33776 | | 12/1995 | |
| WO | WO 96/00245 | * | 1/1996 | |
| WO | WO 98/22424 | | 5/1998 | |
| WO | 98/30609 | | 7/1998 | |
| WO | WO 98/30610 | | 7/1998 | |
| WO | WO 98/30612 | | 7/1998 | |
| WO | WO 98/37109 | | 8/1998 | |
| WO | WO 98/49208 | | 11/1998 | |
| WO | WO 96/23010 | | 8/1999 | |

OTHER PUBLICATIONS

R. Ernst et al., J. Am. Chem. Soc., vol. 104, 1982, pp. 3737–3739.*

R. Ernst et al., J. Am. Chem. Soc., vol. 107, 1985, pp. 5016–5018.*

Brookhart et al., "[(3,5–(CF3)2C6H3)4B]–[H(OEt2)2]+: A Convenient Reagent for Generation and Stabilization of Cationic, Highly Organometallic Complexes", Organometallics 1992, 11, 3920–3922.

Potesil et al., "Thin–Layer Chromatography of Enamino Ketones, II*," Journal of Chromatoraphy, 312 (1984) 387–393.

McGeachin, S.G., "Synthesis and properties of some b–dilketimines derived from acetylacetone, and their metal complexes," Canadian Journal of Chemistry, vol. 46, 1968.

Parks et al., The Synthesis, Solution Stereochemistry, and Electron Delocalization Properties of BIS(b–iminoamino)nickel(II) complexes.

Honeybourne et al., "Some Metal Complexes of 1,3–Di–-imines." Chemical Communications, 1968.

Healy et al., "Crystallographic and N.M.R.–Relaxation Studies on BIS[{N,N'–(1,3–dimethylpropanediylidene)–dianilinato](1–)nickel(II)," Australian Journal of Chemistry, vol. 32, No. 4, Apr. 1979.

Kuhn et al., "(C7H13BF2)Cr(C))3: A Vinamidine (1,5–Diazapenta–1,e–diene) Boron Difluoride as an Cyclohexadienide Type Ligand," London Journal of Chemical Society, Chemical Communications, No. 15, 1989, 975–976.

Giannini et al., "Migratory Aptitude of the Zr–C Functionalities Bonded to a Macrocyclic Structure: Thermally– and Solvent–Assisted Intra– and Intermolecular Migrations in Dialkyl (dibenzotetramethyltetraazaannulene)zirconium(IV)," Journal of American Chemical Society, 1995, 117, 5801–5811.

Uhrhammer et al., "Cationic d0 Metal Alkyls Incorporating Tetraaza–Macrocycle Ancillary Ligadns. Synthesis and Reactivity of (Me8taa)M(R)+ and (Me4taen)M(R)+(M–Zr, Hf) Complexes," Journal of American Chemical Society, 1993, 115, 8439–8494.

Black et al. "Tetraaza Macrocycles as Ancillary Ligands in Early Metal Alkyl Chemistry. Synthesis and Characterization of Out–of–Plane (Me4taen) ZrX2 (X=Alkyl,Benzyl, NMe2,Cl) and (Me4taen)ZrX2(NHMe2) (X=Cl,CCPh) Complexes," Organometallics, 1995, 14, 3539–3550.

Feldman et al., "Electrophilic Metal Precursors and a B–Diimine Ligand for Nickel(II)_and Palladium(II)–Catalyzed Ethylene Polymerization," Organometallics, 1997, 16, 1514–1516.

Scollard et al., "Living Polymerization of a–Olefins by Chelating Diamide Complexes of Titanium," Journal of American Chemical Society, 1996, 118, 10008–10009.

Killian et al., "Living Polymerization of a–Olefins Using Nia–a–Diimine Catalysts. Synthesis of New Block Polymers Based on a–Olefins," Journal of American Chemical Society, 1996, 118, 11664–11665.

Yang et al., "'Cation–like' Homogeneous Olfein Polymerization Catalysts Based upon ziroconocene Alkyls and Tris(pentafluorophenyl)borane," Journal of American Chemical Society, 1991, 113, 3623–3625.

Yamamoto et al., "Mechanism of Carbene Formation from the Excited States of Diazirine and Diazomethane" An MC–SCF Study, Journal of American Chemical Society, 1994, 116, 2064–2074.

Manzer et al., "Tetrahydrofuran Complexes of Selected Early Transition Metals," Inorganic Syntheses vol. XXI, John Wiley and Sons, 135–140. No Date Available.

Herwig et al., "Chromium Trichloride Tetrahydrofuranate," Apr. 1958.

Gibson, Vernon C. et al., "Chromium(III) complexes bearing N,N–chelate ligands as ethene polymerization catalysts," Chem. Commun., 1998, pp. 1651–1652.

Budzelaar, Peter H.M., et al., "b–Diiminato Complexes of V(III) and Ti(III)—Formation and Structure of Stable Paramagnetic Dialkymetal Compounds," Eur. J. Inorg. Chem, 1998, p. 1485+.

Richeson, Darrin S. et al., "Facile Insertion of Nitriles into Paramagnetic Chromium (III) Alkyls. Crystal Structure of a u2–Ketimino Complex," J. Am. Chem. Soc., 1987, 109, 5868–70.

Lappert et al., Recent studies on metal and metalloid bis (trimethylsilyl) methyls . . . , Journal of Organometallic Chemistry 500, (1995) 203–217.

Scollard, et al., Polymerization of aplha–Olefins by Chelating diamide Complexes of Titanium, Macromolecules, 1996, 5241–5243.

Kim et al., Organometallics, 17(21), 4541–4543, 1998.

Rahim et al., Synthesis and Structure of Acyclic Bis (ketenimine) Complexes of Zirconium, Organometallics, 17(7) 1998, 1315–1323.

Hitchcock et al. "Transformation of the Bis(trimethylsilyl)methyl into Aza–allyl and B–dikeinimato . . . " J. Chem. Soc., Chem Commun., 2637–2638, May 1994.*

Lappert et al. "Recent Studies on Metal and Metalloid bis(trimethylsily)methyls and the Transformation . . . " J. Organomet. Chem., 500, 203–217, Oct. 1995.*

H.F. Mark et al. "Encyclopedia of Polymer Science and Engineering" vol. 7, 2nd edition, 1987, pp. 480–488, Jun. 1987.*

* cited by examiner

*Primary Examiner*—Mark L. Bell
*Assistant Examiner*—J. Pasterczyk
(74) *Attorney, Agent, or Firm*—Pillsbury Winthrop LLP

(57) ABSTRACT

The present invention relates to catalyst systems, processes for making such catalysts, intermediates for such catalysts, and olefin polymerization processes using such catalysts wherein such catalyst includes a component represented by the following formula 1A:

IA

[Chemical structure showing a metal complex with $R^1$, $R^2$, $R^3$, R, R' substituents and $M(T)_a(L)_b$]

or

[Chemical structure showing the cationic form with $X^-$ counterion]

wherein

R and R' independently represent a hydrogen atom, or a substituted or unsubstituted, branched or unbranched hydrocarbyl or organosilyl radical;

$R^1$, $R^2$, and $R^3$ independently represent a hydrogen atom, or a substituted or unsubstituted, branched or unbranched hydrocarbyl radical;

M is a group IIIB, IVB, VB, VIB, VIIB or VIII transition metal;

T independently represents a univalent anionic ligand such as a hydrogen atom, or a substituted or unsubstituted hydrocarbyl halogeno, aryloxido, arylorganosilyl, alkyloriganosilyl, amido, arylamido, phosphido, or arylphosphido group, or two T groups taken together represent an alkylidene or a cyclometallated hydrocarbyl bidentate ligand;

L independently represents a sigma donor stabilizing ligand; X, which is optional, represents a relatively weakly coordinated anion; and a=0 to 4 inclusive, b=0 to 4 inclusive, provided a+b≦4.

51 Claims, 9 Drawing Sheets

CATALYST COMPOUNDS WITH β-DIMINATE ANIONIC LIGANDS AND PROCESSES FOR POLYMERIZING OLEFINS

This is a Continuation-in-Part of: National Appln. No. 09/022,414 filed Feb. 12, 1998, now abandoned.

FIELD OF THE INVENTION

The present invention relates to catalyst systems, processes for making such catalysts, intermediates for such catalysts, supports for such catalysts and olefin polymerization processes using such catalysts.

BACKGROUND OF THE INVENTION

Olefin polymers are useful as plastics for packaging materials, molded items, films, etc., and as elastomers for molded goods, industrial belts of various types, tires, adhesives, and other uses. It has been well known in the art that the structures of olefin polymers, and hence their properties and capability of use, are highly dependent on the catalyst used during their synthesis. Therefore, as the potential applications for polymers have changed and developed over the past years so too has the need for new and more catalyst systems and improved polymerization processes utilizing such catalysts become necessary.

SUMMARY OF THE INVENTION

In accordance with the present invention, there is provided a novel catalyst system for the polymerization of olefins, said catalyst system including a transition metal complex with at least one β-diiminate bidentate ligand.

There is also provided in accordance with the present invention novel catalyst compounds, and supported catalyst compounds, for the polymerization of olefins, said compounds being represented by Formulas I(A&B), as follows:

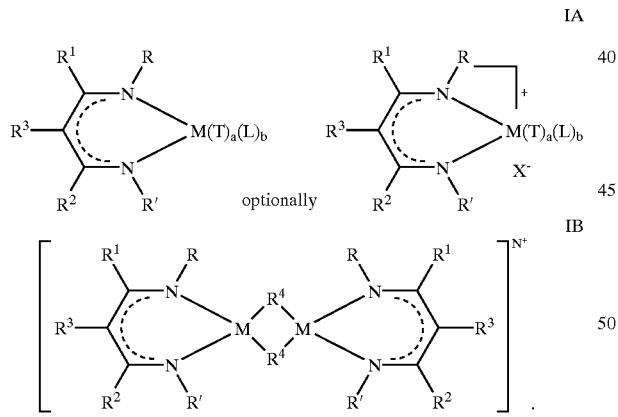

wherein
- R and R' independently represent a hydrogen atom, or a substituted or unsubstituted, branched or unbranched hydrocarbyl or organosilyl radical;
- $R^1$, $R^2$, and $R^3$ independently represent a hydrogen atom, or a substituted or unsubstituted, branched or unbranched hydrocarbyl radical;
- $R^4$ independently represents a bridging ligand, preferably including a hydrogen atom, or a substituted or unsubstituted, branched or unbranched hydrocarbyl, halogeno, aryloxido, arylorganosilyl, alkylorganosilyl, amido, arylamido, phosphido, or arylphosphido group;
- M independently represents a group IIIB, IVB, VB, VIB, VIIB or VIII transition metal;
- N=an integer from 0 to 3, preferably 0 or 1;
- each T independently represents a univalent anionic ligand such as a hydrogen atom, or a substituted or unsubstituted hydrocarbyl, halogeno, aryloxido, arylorganosilyl, alkylorganosilyl, amido, arylamido, phosphido, or arylphosphido group, or two T groups may together form other anionic ligands such as an alkylidene or a cyclometallated hydrocarbyl radical;
- each L independently represents a sigma donor stabilizing ligand or one L together with one T may together represent a second β-diiminate ligand represented by Formula II (below);
- X, which is optional, represents a relatively weakly coordinated anion; and
- a=an integer from 0 to 4 inclusive, b=an integer from 0 to 4 inclusive, provided a+b≦4.

Further provided in accordance with the present invention is a novel process for the polymerization of olefins. The process provides for the polymerization of one or more olefins in the presence of a homogeneous catalyst comprising a catalyst or catalysts represented by Formulas I(A&B) or a heterogeneous catalyst system comprising at least one Formula I(A&B) catalyst and one or more co-catalysts.

The present invention also provides for a novel process of making a catalyst component represented by Formulas I(A&B) by contacting at least one group IIIB, IVB, VB, VIB, VIIB or VIII transition metal containing compound with at least one compound containing at least one β-diiminate ligand represented by the following Formula II, in particular a compound represented by Formula III (below):

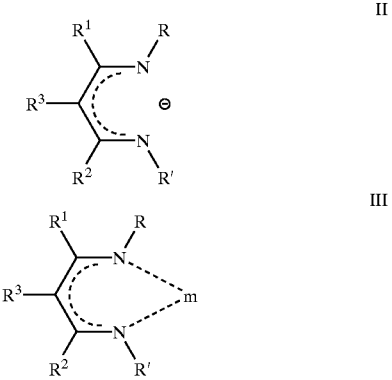

wherein
- R, R', $R^1$, $R^2$ and $R^3$ have the same meanings stated above; and
- represents a group that is readily displaced by a transition metal, for example hydrogen or a group comprising a group IA or IIA metal.

DETAILED DESCRIPTION OF THE INVENTION

Figure 1:
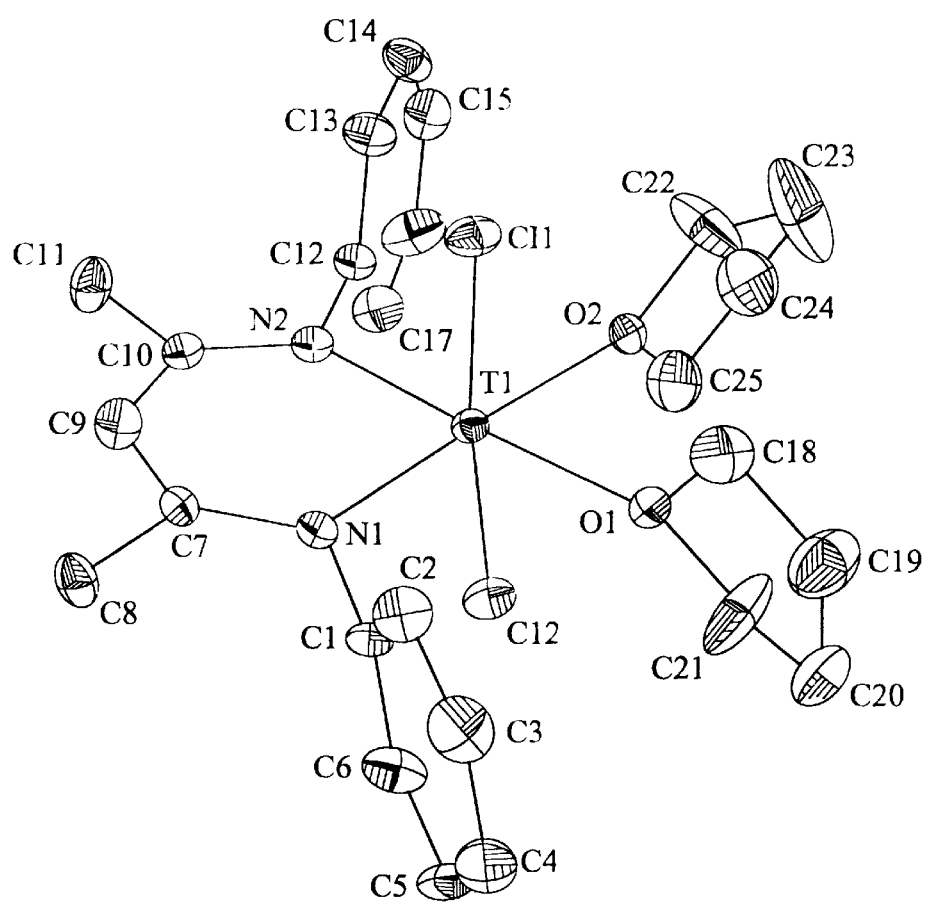
FIG. 1 depicts the crystal structure of the (Ph)$_2$ nacnacTiCl$_2$(THF)$_2$, prepared in Example 1A.

Herein certain terms are used to define certain chemical groups and compounds. These terms are defined below.

"alkyl metal" or "metal alkyl" refer to a compound having an alkyl radical bound directly to a metal. For example, an alkyl metal (or metal alkyl) would include alkyl aluminum (or aluminum alkyl).

"group IA, IIA, IIB, IIIA, IIIB, IVB, VB, VIB, VIIB or VIII" refers to the metals within the respective group number of the Periodic Table of the Elements (CRC Handbook of Chemistry and Physics, 78$^{th}$ ed. 1997–1998). For example, group IVB would include titanium, zirconium, etc. and group VIII would include palladium, platinum, cobalt, etc.

"hydrocarbyl" refers to a univalent group containing only carbon and hydrogen. if not otherwise stated, hydrocarbyl as used herein preferably contains 1 to about 30 carbon atoms.

"linear $\alpha$-olefin" refers to an olefin, defined below, wherein R$^{10}$ represents a hydrogen atom or an n-alkyl. If not otherwise stated, linear $\alpha$-olefin as used herein preferably contains 2 to about 12 carbon atoms.

"olefin" refers to a compound of formula CH$_2$=CHR$^{10}$, wherein R$^{10}$ represents a hydrogen atom or n-alkyl or branched alkyl, preferably hydrogen or n-alkyl.

"organosilyl" refers to a univalent group containing at least one carbon to silicon bond. One example is trimethylsilylmethyl.

"Polymerization" refers to a process that produces polymers, copolymers, terpolymers, etc. that generally have a degree of polymerization of at least about 20 or more. However, the process is also useful to produce oligomers of a lower degree of polymerization.

"saturated hydrocarbyl" refers to a hydrocarbyl radical that is free from double or triple bonds, also referred to as unsaturated bonds. Examples of such groups include alkyl and cycloalkyl.

"substituted hydrocarbyl" refers to a hydrocarbyl radical that contains one or more substituent groups.

"transition metals" refers generally to the group IIB, IVB, VB, VIB, VIIB or VIII transition metals. If not otherwise stated, transition metals as used herein preferably includes the group IVB, VB, or VIB transition metals.

"unsaturated liydrocarbyl" refers to a hydrocarbyl radical that contains one or more double or triple bonds. Examples of such groups include olefinic, acetylenic, or aromatic groups.

"unsubstituted hydrocarbyl" refers to a hydrocarbyl radical that contains no substituent groups.

The present invention concerns catalysts and polymerization processes for olefins in the presence of various homogenous transition metal catalysts complexed with at least one $\beta$-diiminate bidentate ligand or a catalyst system comprising at least one such transition metal catalyst with one or more co-catalysts. The $\beta$-diiminate ligand may be represented by Formula II, as follows:

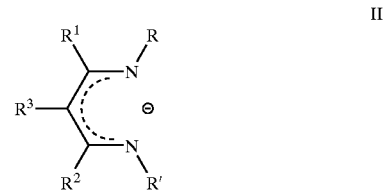

II wherein

R, R', R$^1$, R$^2$ and R$^3$ have the meanings stated above; and
said transition metal also has bound to it a ligand that may be displaced by said olefin or added to said olefin.

The following Reaction Scheme 1 details one way of synthesizing a $\beta$-diiminate precursor compound corresponding to the $\beta$-diiminate monoanionic ligand, represented by Formula II. This synthesis reaction is further discussed in the journal articles by S. G. McGeachin Canadian J. of Chem. v.46, pp. 1903–1912 (1968) and T. Potesil and H. Potesilova, J. of Chromatogr., v.312, pp. 387–393 (1984), the disclosures of which are hereby incorporated by reference. It will be appreciated from this series of transformations that the $\beta$-diimine compound can readily be prepared with different groups on each of the nitrogen atoms by utilizing two different substituted amines in the reaction sequence. By analogy to the familiar "acac" nickname for the acetylacetonato moiety, the nickname "nacnac" will be used herein to refer to the 2,4-pentane diiminato moiety, represented by Formula II. For example, the hydrogen or lithium bridged diimine structures in the last two steps of Reaction Scheme 1 may be represented herein as nacnacH and nacnacLi, respectively. The nacnac terminology used herein may further include a prefix indicating the type of radical group present in the R and R' positions, for instance, "Me" to represent methyl or "Ph" to represent phenyl (e.g., (MPh)(Me)nacnacH or (Ph)$_2$nacnacH).

Reaction Scheme 1: Synthesis of $\beta$-Diiminates ((R)(R')nacnacLi)

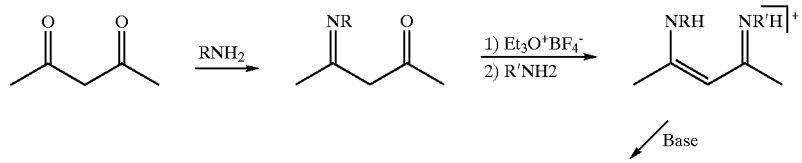

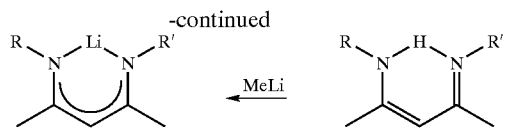

The catalyst compound of the present invention may be prepared in a variety of ways, using techniques and, in addition to the novel β-diimine compounds and corresponding monoanionic β-diiminate ligands, known precursors for the cationic and anionic portions of the catalyst compound. The catalyst compound of the present invention may be formed either beforehand or in situ (i.e., in the vessel in which the polymerization is to take place).

The β-diimine compounds of Formula III. which may serve as precursors for the monoanionic bidentate ligand, represented by Formula II, can be reacted with a transition metal compound to form a catalyst compound, as represented by Formula I(A&B), that is useful for the polymerization of olefins. In a preferred form of the β-diimine compounds of Formula III, the hydrogen or metal containing group represented by m includes hydrogen or a group IA metal, in particular, lithium, sodium or potassium.

Useful transition metal containing compounds for forming such catalyst compounds include those which comprise a group IIIB, IVB, VB, VIB, VIIB or VIII transition metal having ligands that may be displaced by the monoanionic bidentate ligand derived from the β-diimine precursor compound. Particularly suitable transition metal containing compounds include transition metal salts having ligands, in addition and/or including those represented by T and L of Formula I, that are readily displaceable by the ligand derived from the diimine precursor compound under conditions that do not adversely affect either the transition metal compound or ligand adducts thereof. These transition metal salts include transition metal halides (such as dichloride, trichloride or tetrachloride, with trichloride being preferred), transition metal carboxylates (such as acetates), transition metal alkoxides (such as methoxides), or transition metal sulfonates (such as triflates or tosylates). Typically, these catalysts may be formed in the presence of a suitable solvent. Suitable solvents include Lewis bases such ethers, thioethers, amines or nitriles with diethylether and tetrahydrofuran being preferred. In addition, a metal alkyl including, in particular, metal alkyls having a group IA, IIA or IIIA metal such as lithium alkyls (such as alkyl methyl lithium, ethyl lithium, n-propyl and/or i-propyl lithium, n-butyl, or t-butyl lithium), aluminum alkyls, preferably including aluminum trialkyls (such as trimethyl aluminum, triethyl aluminum, triisobutylaluminum or trioctyl aluminum), Grignard reagants and the like may be simultaneously reacted with the other reactants to form the desired catalyst compound. Alternatively, a compound comprising the β-diiminate ligand, such as those represented by Formula I (A&B), can be subsequently reacted with such metal alkyls to form the desired catalyst compound or a compound of Formula I (A&B) can be reacted in situ and/or in the presence of an olefin to provide a catalyst having the desired activity.

With respect to the catalyst compounds represented by Formula I (A&B), above, the relatively weakly coordinated anion X, when present, may be any suitable anion known for this purpose. Suitable anions are often bulky anions, particularly those that delocalize their negative charge. X, in Formula I (A&B), preferably represents tetrakis [3,5-bis (trifluoromethyl)phenyl]borate (herein referred to as BArF$^-$), (phenyl)$_4$B$^-$, (C$_6$F$_5$)$_4$B$^-$, (CH$_3$)(C$_6$F$_5$)$_3$B$^-$, PF6$^-$, BF$_4^-$, SbF$_6^-$, trifluoromethanesulfonate (herein referred to as triflate or OTf$^-$), and p-toluenesulfonate (herein referred to as tosylate or OTs$^-$). Preferred weakly coordinating anions include BArF$^-$ and (C$_6$F$_5$)$_4$B. Catalyst compounds of Formula I (A&B) wherein the weakly coordinated anion is present may be made by further reacting a compound of Formula I (A&B) having at least one alkyl group, with about one equivalent of a strong acid, the conjugate base of which is a non-coordinating anion such as noted for X above, in the presence of a suitable solvent. Suitable solvents include, for example, methylene chloride, hexane, benzene, toluene, chlorobenzene, diethyl ether and the like.

The substituent groups represented by R, R', R$^1$, R$^2$ and R$^3$ should be selected so that they do not substantially interfere or impede the particular type of polymerization reaction for which the catalyst is designed. Whether a particular group is likely to interfere can initially be judged by one skilled in the art based on the parameters of the process where the catalyst will be employed. For instance, in polymerization processes where an alkyl aluminum compound is used, catalyst containing an active (relatively acidic) hydrogen atom, such as hydroxyl or carboxyl may not be suitable because of the known reaction between alkyl aluminum compounds and such active hydrogen containing groups (but such polymerization processes may still be possible if enough "extra" alkyl aluminum compound is added to react with these groups). However, in very similar polymerization processes where alkyl aluminum compounds are not present, these groups containing active hydrogen may be present. An important factor to consider in determining the operability of compounds containing any particular functional group are the effect of the group on the coordination of the metal atom, and side reactions of such a group with other process ingredients, such as those noted above. Therefore, of course, the further away from the metal atom the functional group is, the less likely it is to influence, say, a polymerization. If there is doubt as to whether a particular functional group, in a particular position, will affect a reaction, simple minimal experimentation will provide the requisite answer.

In a preferred form of Formula I (A&B), R and R' independently represent a hydrogen atom, or an alkyl, aryl, alkylaryl, arylorganosilyl, or alkylorganosilyl radical. Preferably, R and R' will independently include such radicals wherein the carbon atom, directly bound to the nitrogen, has at least two carbon atoms bound thereto, for example, isopropyl, phenyl, 2,6-isopropylphenyl, 2,6-dimethylphenyl, 2,6-diethylphenyl, 4-methylphenyl, 2,4,6-trimethylphenyl or 2-t-butylphenyl. R$^1$, R$^2$, and R$^3$ independently represent a hydrogen atom or a hydrocarbyl radical, preferably a hydrogen atom or an alkyl radical having 1–6 carbon atoms, and more preferably a hydrogen atom or methyl radical. M independently represents a group IVB, VB or VIB transition metal, preferably, chromium, vanadium or titanium. These variables defining the preferred forms of the compounds represented by Formula I (A&B) are equally applicable, when present, to the preferred forms of the β-diiminate ligand and β-diiminate compound represented by Formula II & III, respectively.

Each T can independently represent an anionic ligand and $R^4$ can independently represent any suitable bridging ligand such as those that include a hydrogen atom, or a substituted or unsubstituted, branched or unbranched hydrocarbyl, halogeno, aryloxido, arylorganosilyl, alkylorganosilyl, amido, arylamido, phosphido, or arylphosphido group, or two T groups may together form other anionic ligands such as an alkylidene or a cyclometallated hydrocarbyl radical. Exemplary hydrocarbyl groups for T and $R^4$, in Formula I, include methyl, ethyl, propyl, butyl, amyl, isoamyl, hexyl, iso-butyl, heptyl, octyl, nonyl, decyl, cetyl, 2-ethylhexyl, phenyl and the like, with methyl being preferred. Exemplary halogeno groups forT and $R^4$ include chloro, bromo, fluoro, and iodo, with chloro being preferred. Exemplary alkoxido and aryloxido groups for T include methoxido, ethoxido, phenoxido and substituted phenoxido's. Exemplary amido groups for T and $R^4$ include dimethylamido, diethylamido, methylethylamido, di-t-butylamido, diisopropylamido and the like. Exemplary arylamido groups for T and $R^4$ include diphenylamido and other substituted phenyl amido's. Exemplary phosphido groups for T and $R^4$ include diphenylphosphido, dicyclohexylphosphido, diethylphosphido, dimethylphosphido and the like. Exemplary alkylidene anionic ligands, for two T groups taken together, include methylidene, ethylidene and propylidene.

Each L in the above Formula I can represent any suitable electron donor ligand. Suitable ligands include those containing an atom, such as oxygen, nitrogen, phosphorous or sulfur, which has a non-bonded electron pair. Examples of these ligands include, but are not limited to, ethers, amines, phosphines and thioethers. Ethers such as tetrahydrofuran (THF) and amines such as pyridine are preferred, with THF being particularly preferred.

In a preferred form of the catalytic compound represented by Formula IA, a and b independently represent integers from 0 to 3, inclusive. More preferably, a and b independently represent either 0 or 2. It will be appreciated that when Formula IA is meant to characterize a mixture of two or more catalytic compounds whereby a and b represent an average of the a and b values of the catalytic compounds, a and b may independently represent any number from 0 to 4, including 1.2 to 1.8.

A preferred compound of the present invention includes those comprising at least two β-diiminate bidentate ligands, each β-diiminate bidentate ligand independently represented by Formula II. The compounds include those wherein two or more of the β-diiminate bidentate ligands are coordinated to a common transition metal and polynuclear metal complexes wherein there are two or more transition metals bridged together each having at least one β-diiminate bidentate ligand coordinated thereto. These would include, for example, compounds comprising transition metals in various oxidation states including the +II and +III, as well as compounds represented by formula I(A)

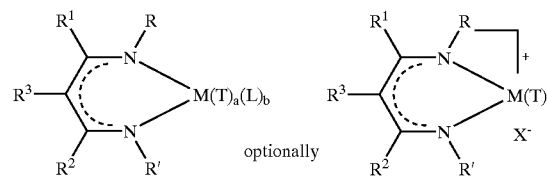

IA wherein a and b are both at least I such that at least one L group together with at least one T group represent a β-diiminate ligand represented by Formula II. In the event, that a and/or b are greater than 1, the additional L and T groups will represent any of those groups discussed herein including together an additional β-diiminate ligand represented by Formula II.

The polymerization reaction using the catalyst of the present invention may be carried out with a catalyst compound represented by Formula I (A&B) either by itself, referred to as a homogenous catalyst system, or with one or more co-catalysts. The catalyst and/or co-catalysts may initially be in a solid state or in solution. The olefin and/or olefins may be in the gas or liquid state (including gas dissolved in a solvent). A liquid, which may or may not be a solvent for any or all of the reactants and/or products may also be present. Suitable liquids include alkanes, cycloalkanes, halogenated alkanes and cycloalkanes, and ethers. Solvents that are especially useful include methylene chloride, hexane, toluene, dichlorobenzene, and benzene.

Co-catalysts useful in the practice of the present invention are group IIA, IIB, IIIA and IIB metal alkyls having at least one alkyl group, preferably an alkyl group having 1 to 8 carbon atoms, bonded to the metal. Suitable metal alkyls include dialkyl magnesium, dialkyl zinc, trialkyl boranes, triarylboranes and aluminum alkyls. Suitable aluminum alkyls include trialkylaluminums (such as trimethylaluminum, triethylaluminum, triisobutylaluminum, and trioctylaluminum). Trialkylaluminums with alkyl groups of four carbons or greater are preferred. Other aluminum alkyls useful in the practice of the present invention include alkylaluminum alkoxides (such as diethylaluminum ethoxide and ethylalurninum diethoxide), and alkylaluminum halides (such as diethylaluminum chloride, diethylaluminum bromide, diethylaluminum iodide, diethylaluminum fluoride, ethyl aluminum dichloride, ethyl aluminum dibromide, ethyl aluminum diiodide, ethyl aluminum difluoride and ethyl aluminum sesquichloride). Suitable triarylboranes include those that are fluorine substituted (such as tripentafluorophenyl borane).

Other suitable aluminum alkyls are aluminoxanes including those represented by the general formula $(R''—Al—O)_n$ for the cyclic form and $R''(R''—Al—O)_n—Al(R'')_2$ for the linear form. In these formulas, R" independently represents an alkyl group (such as methyl, isopropyl, butyl and the like) preferably with more than two carbon atoms, more preferably with 3–5 carbon atoms, and n is an integer, preferably from about 1 to about 20. Most preferably, R includes a methyl or isobutyl group. Mixtures of linear and cyclic aluminoxanes useful in this invention include, but are not limited to, ethyl aluminoxanes, isobutyl aluminoxane, and methyl aluminoxane.

The preferred metal alkyl co-catalysts generally include aluminoxanes and trialkylaluminum. When a co-catalyst is used, the mole ratio of the metal alkyl co-catalyst to catalyst should be from about 1:1 to about 1000:1. The preferred mole ratio being from about 10:1 to about 200:1.

The catalyst system of the present invention may be used in either slurry or gas phase polymerization processes. After catalysts have been formed, the polymerization reaction isconducted by intermixing the monomer charge with a catalytic amount of the catalyst at a temperature and at a pressure sufficient to initiate the polymerization reaction. If desired, an organic solvent may be used as a diluent and to facilitate materials handling. The polymerization reaction is carried out at temperatures of from about −100° C. up to about 200° C., depending on the operating pressure, the pressure of the entire monomer charge, the particular catalyst being used, and its concentration. Preferably, the temperature is from about 20° C. to about 135° C. The pressure can be any pressure sufficient to initiate the polymerization of the monomer charge. For instance, the pressure may range from atmospheric up to about 1000 psig. As a general rule, a pressure of about 20 to about 800 psig is preferred.

When the catalyst is used in a slurry-type process, an inert solvent medium is used. The solvent should be one which is inert to all other components and products of the reaction system, and be stable at the reaction conditions being used. It is not necessary, however, that the inert organic solvent medium also serve as a solvent for the polymer produced. The inert organic solvents which may be used include saturated aliphatic hydrocarbons (such as hexane, heptane, pentane, isopentane, isooctane, purified kerosene and the like), saturated halogenated alkanes (such as dichloromethane, choloroform and the like) saturated cycloaliphatic hydrocarbons (such as cyclohexane, cyclopentane, dimethylcyclopentane, and the like), aromatic hydrocarbons (such as benzene, toluene, xylene and the like). Particularly preferred solvents are dichloromethane, toluene, cyclohexane, hexane, benzene and heptane.

When the catalyst is used in a gas phase process, it may be suspended in a fluidized bed with, e.g., ethylene. Temperature, pressure and ethylene flow rates are adjusted so as to maintain acceptable fluidization of the catalyst particles and resultant polymer particles.

The catalyst of the present invention may be employed on a solid catalyst support (as opposed to just being added as a solid or in solution), for instance on silica gel or any other suitable catalyst support that does not adversely affect the performance of the catalyst. By supported is meant that the catalyst may simply be carried physically on the surface of the solid support, may be adsorbed, absorbed, or carried by the support by other means.

In the catalyst systems of the present invention, the catalyst may be deposited onto an inorganic support. Preferably, the support is calcined at a temperature of between 200 to 800° C., more preferably to a temperature of between 300 to 600° C. Suitable inorganic metal oxide supports include silica, alumina, silica-alumina mixtures, thoria, zirconia, magnesium oxide and similar oxides. Suitable inorganic metal phosphates include aluminum phosphate, zirconium phosphate, magnesium-containing alumina phosphate and alumina aluminum phosphate. Silicas, aluminum phosphates and alumina aluminum phosphates are preferred. Suitable silica supports include Davison 952, Davison 955, Crosfield EP-10, Crosfield EP17MS, PQ MS3030 and the like. Further examples of useful supports are the following: alumina aluminum phosphates with aluminum to phosphorus ratios of about 5:1 to 1:1 as disclosed in U.S. Pat. Nos. 4,080,311 and 4,219,444; magnesia-alumina-aluminum phosphates as described in U.S. Pat. No. 4,210,560; zinc oxide-cadmium oxide-alumina-aluminum phosphates such as those disclosed in U.S. Pat. No. 4,367,067; and the calcium, barium, and/or strontium oxide-alumina-aluminum phosphates described in U.S. Pat. Nos. 4,382,877 and 4,382,878 (all noted patents are hereby incorporated in the entirety by reference). The acidity of these supports can be adjusted by judicious inclusion of basic metals such as alkali and alkaline earth metals (Ca, Be, Mg, K, Li) to counteract excessive acidity. Other useful supports include magnesium halides, particularly magnesium chloride, such as those described in "Transition Metals and Organometallics as Catalysts for Olefin Polymerization" (1988, Springer-Verlag) edited by W. Kaminsky and H. Sinn and "Transition Metal Catalyzed Polymerizations-Ziegler-Natta and Metathesis Polymerizations" (1988, Cambridge University Press) edited by R. Quirk.

The supports useful in this invention should have a high surface area. In general, these supports should have the characteristics listed in the following table:

| Property | Broad Range | Preferred Range |
|---|---|---|
| Surface Area | 25–600 m$^2$/g | 100–370 m$^2$/g |
| Pore Volume | 0.25–5 cm$^3$/g | 0.7–3.5 cm$^3$/g |
| Mean Particle Diameter | 30–200 microns | 60–140 microns |

Preferably, the pore size distribution is broad, with a significant percentage of the pores in the macropore range (>500 Angstroms). Preferably, at least 50% of the pores are macropores. It is also desirable that the support be substantially anhydrous before the catalyst compound is deposited on it. Thus, it is desirable to calcine the support prior to deposition of the catalyst compound.

The supported catalysts of this invention are readily prepared by a variety of techniques include those known in the art. For example, a solution of the catalyst compound in aliphatic, aromatic and/or cycloaliphatic hydrocarbons, or ethers such as diethyl ether or tetrahydrofuran can be stirred with the support until the catalyst compound is adsorbed on or reacted with the support. Suitable liquids for forrming such solutions include alkanes, cycloalkanes, halogenated alkanes and cycloalkanes. Liquids that are especially useful include methylene chloride, hexane, toluene, dichlorobenzene, and benzene. The amount of catalyst compound relative to the amount of support will vary considerably depending upon such factors as the particle size of the support, its pore size and surface area, the solubility of the catalyst in the solvent employed, and the amount of catalyst compound which is to be deposited on the support. However, in general the amount of catalyst compound used is adjusted so that the final metal content (calculated as the element), relative to the support, is in the range of from about 0.01 to about 10 weight percent. In most cases, the most desirable level is in the range of about 0.1 to about 5 weight percent.

Preferred olefins and cycloolefins in the polymerization include at least one or more of the following monomers: ethylene, propylene, 1-butene, cyclopentene, 1-hexene; with ethylene and mixtures of ethylene with propylene and/or 1-hexene being more preferred. Ethylene alone is especially preferred. Oligomers may also be used, with or without a co-monomer. As may be desired, more than one monomer may be employed in which case a copolymer will be the likely product obtained. However, depending on the reactants employed and the given reaction conditions, polymerization may not always occur.

EXAMPLES

The following examples are given as particular embodiments of the invention and to demonstrate the practice and advantages thereof. It is understood that the examples are given by way of illustration and are not intended to limit the specification or the claims that follow in any manner.

In preparation of the following catalysts, all manipulations were performed under vacuum using glove box or Schlenk techniques. The chemicals are commercially available from sources such as Strem Chemical Co. and Aldrich Chemical Co. Methylaluminoxane (MAO), unless otherwise noted, was used as a 10 wt. % in toluene solution. Methyl lithium (MeLi) was used as a 1.4M solution or as a solid obtained by evaporation of the solvent. Aniline and Aniline-$d_5$ ($C_6D_5NH_2$) was freshly distilled just prior to use. Trimethylsilylmethyllithium was supplied as a 1.0M solution in pentane and crystallized as a white crystalline solid from solution at −30° C. prior to use. Benzene-d$_6$ (C$_6$D$_6$) and Tetrahydrofuran-d$_8$ (THF-d$_8$) were pre-dried with Na and stored under vacuum over a Na/K alloy prior to use. Pyridine-d$_5$ (pyr-d$_5$) and Dichloromethane-d$_2$ (CD$_2$Cl$_2$) were dried with CaH$_2$ and vacuum distilled onto pre-activated 4 Å molecular sieves prior to use. Pentane, Diethylether, Tetrahydrofuran (THF), and Hexamethyldisiloxane (HMDS) were dried over Na/benzophenone prior to use.

Trichloro tris(tetrahydrofuran) vanadium (VCl$_3$(THF)$_3$) and Trichloro tris(tetrahydrofuran) titanium (TiCl$_3$(THF)$_3$) are prepared from the corresponding metal trichloride (TiCl$_3$ and VCl$_3$, respectively) by reaction with anhydrous tetrahydrofuran as noted in the article by Manzer, L. E. *Inorganic Synthesis* Vol. XXI, pp. 135–140, John Wiley & Sons (1982) the complete disclosure of which is hereby incorporated by reference.

Trichloro tris(tetrahydrofuran) chromium (CrCl$_3$(THF)$_3$) is prepared by converting anhydrous chromium trichloride into its tetrahydrofuranate by continuous extraction with anhydrous tetrahydrofuran of its solid form admixed with catalytic amounts of zinc dust as noted in the article by Herwig, W.; Zeiss, H. H, *Jounial of Organic Chemistry* Vol. 23, p. 1404 (1958) ) the complete disclosure of which is hereby incorporated by reference.

The crystalline oxonium acid [(3,5-(CF$_3$)$_2$C$_6$H$_3$)$_4$B]$^-$[H(OEt$_2$)$_2$]$^+$ is synthesized by exposing a solution of Na[(3,5-(CF$_3$)$_2$C$_6$H$_3$)$_4$B] in ether to HCl and isolating the [(3,5-(CF$_3$)$_2$C$_6$H$_3$)$_4$B]$^-$[H(OEt$_2$)$_2$]$^+$. This synthesis is discussed in the article by Brookhart, M.; Grant, B.; Volpe, A. F., *Organoinetallics* Vol. 11, No. 11, pp. 3920–3922 (1992).

Analytical Procedures:

NMR spectra were recorded using one or more of the following spectrometers Bruker AM-250, WM-250 or 400; chemical shifts were referenced to the residual proton resonance of the deuterated solvent indicated.

Fourier Transform Infra Red spectra were recorded on a Mattson Alpha Centauri spectrometer with a resolution of 4 cm$^{-1}$.

UV-VIS spectra were recorded using a Bruins Omega 20 spectrophotometer and a Beckman DU 640 spectrometer.

Mass spectra were obtained from the University of Delaware Mass Spectrometry Facility.

Elemental analyses were performed either by Oneida Research Services, Whiteboro, N.Y. 13492 or Schwarzkopf Microanalytical Laboratory, Woodside, N.Y. 11377. Note: the elemental analyses for Examples 1A and 1B did not fit the calculated values, presumably, due to the loss of the coordinated solvents resulting from vigorous pumping under high vacuum.

Room temperature magnetic susceptibilities were determined using a Johnson-Matthey Magnetic Susceptibility Balance which utilizes a modification of the Gouy method. The molar magnetic susceptibility was corrected for diamagnetism using Pascal constants and the effective magnetic moment ($\mu_{eff}$) was calculated from the expression:

$$\mu_{eff} = 2.828(T_{10}\chi m)^{1/2}$$

where T is the temperature in Kelvin and $\chi$m is the molar magnetic susceptibility corrected for diamagnetism.

Preparation of 2-N-Phenylamino-4-N'-Phenylimino-2-Pentene, (Ph)$_2$nacnacH

In a flask, re-distilled aniline was mixed with a molar equivalent (eq.) of 2,4-pentanedione and benzene were mixed. The mixture was boiled on an oil-bath and the distilled-off azeotropic mixture (benzene-water) was replaced with benzene until all water was separated. Then, the surplus solvent was removed by distillation. The crude product was re-distilled in vacuo (boiling point approx.75° C.) to give a crystalline substance which was re-crystallized from n-hexane to yield fine yellowish crystals of 2-N-phenylamido-2'-penten-4-one.

These 2-N-phenylamido-2'-penten-4-one yellow crystals were then used to prepare (Ph)$_2$nacnacH in accordance with the Reaction Scheme 1 (above). A molar eq. of triethyloxonium tetrafluoroborate in dichloromethane was added dropwise to the 2-N-phenylamido-2'-penten-4-one in the same solvent. The mixture was allowed to stand for 30 minutes. Then, 1 molar eq. of aniline in dichloromethane was added. After 1 hour the solvent was removed completely in vacuo and the residual oil was dissolved in hot ethyl acetate and the 2-N-phenylamino-2'-penten-4-phenylimmonium tetrafluoroborate product was allowed to crystallize.

The free base of the ligand, (Ph)$_2$nacnacH was prepared from the cationic salt, 2-N-phenylamino-2'-penten-4-phenylimmonium tetrafluoroborate. An equimolar reaction with potassium hydride (KH) (optionally MeLi) resulted in about a 98% yield of yellow neutral, deprotonated, (Ph)$_2$nacnacH crystals. Alternatively, a metal salt, for instance (Ph)$_2$nacnacLi (or (Ph)$_2$nacnacK), could have been formed from the 2-N-phenylamino-2'-penten-4-phenylimmonium tetrafluoroborate cation salt and two equivalents of MeLi (or KH). Deuterated versions of these compounds are formed by substituting aniline-d$_5$ for unlabeled aniline.

Example 1A

Preparation of 2,4-pentane di(N-phenyl)iminato Dichloro Bis-tetrahydrofuran Titanium, (Ph)$_2$nacnacTiCl$_2$(THF)$_2$ and the Corresponding Compound with the Deuterated Ligand, (Ph-d$_5$)$_2$nacnac:

1.50 g (6.0 mmoles) of (Ph)$_2$nacnacH was dissolved in 50 ml of THF and cooled to −30° C. 1 equivalent (132 mg) of MeLi was slowly added as a solid with stirring. The resulting (Ph)$_2$nacnacLi was added dropwise over a three hour period, to a cooled 2.223 g (6.0 mmole) solution of TiCl$_3$(THF)$_3$ in IS0 ml of THF. The color of the solution changed from sky blue to brown, then to dark brown. The reaction mixture was concentrated to 50 ml, and cooled to −30° C. for crystallization. A dark brown microcrystalline powder was isolated by filtration and washed with cold THF several times. After drying under vacuum, 2.92 g (95% yield) of (Ph)$_2$nacnacTiCl$_2$(THF)$_2$ as microcrystalline brown compound was isolated.

The resulting compounds were analytically tested and the results are shown in Tables 1A.1–3. The single crystal X-ray diffraction results are shown in FIG. 1.

TABLE 1A.1

ANALYTICAL DATA FOR
(Ph)$_2$nacnacTiCl$_2$(THF)$_2$
(Ph-d$_5$)$_2$nacnacTiCl$_2$(THF)$_2$

| | | | | | | | |
|---|---|---|---|---|---|---|---|
| $^1$H NMR(CD$_2$Cl$_2$)$^a$: | 103.1 | 89.5 | 11.4 | 6.25 | 3.65 | 3.27 | 1.61 |
| δ (ppm) | (6H, b) | (1H, b) | (2H) | (4H) | (8H) | (2H) | (8H) |
| $^1$H NMR(THF-d$_8$)$^a$: | 27.07 | 12.79 | 8.07 | 3.95 | 3.31 | *** | *** |
| δ (ppm) | (6H) | (1H) | (4H) | (4H) | (2H) | | |
| $^1$H NMR (THF-d$_8$)$^a$: † | 108.76 | 85.80 | *** | *** | *** | *** | *** |
| δ (ppm) | (6H) | (1H) | | | | | |
| $^2$H NMR (THF)$^a$: | 16.1 | 15.4 | 6.1 | *** | *** | *** | *** |
| δ (ppm) | (4D) | (2D) | (4D) | | | | |
| IR-KBr$^b$: (cm$^{-1}$): | 3053 m | 2971 s | 2928 m | 2876 m | 1591 m | 1534 s | 1483 s |
| | 1447 m | 1359 s | 1290 m | 1263 s | 1185 w | 1066 w | 919 m |
| | 840 s | 761 m | 709 s | 518 w | 447 w | *** | *** |
| IR-KBr$^b$: (cm$^{-1}$): † | 2969 m | 2928 m | 2890 m | 2876 m | 2271 w | 1575 m | 1530 m |
| | 1432 m | 1369 vs | 1298 vs | 1250 w | 1147 w | 1015 m | 875 m |
| | 852 m | 824 w | 769 w | 557 m | 464 w | *** | *** |

| | | |
|---|---|---|
| Mass Spectrometry: m/z (%) | 367(100.0) [M$^+$-(THF)$_2$] | 311.8(3.1) [M$^+$-Cl(THF)$_2$] |
| Mass Spectrometry:† m/z (%) | 377.03(100.0) [M$^+$-(THF)$_2$] | 342.06(3.4) [M$^+$-Cl(THF)$_2$] |
| UV-vis (THF)$^c$: λ$_{max}$(ε) | 517(493.6 M$^{-1}$ cm$^{-1}$) | 445(2383.9 M$^{-1}$ cm$^{-1}$) |
| μ$_{eff}$ | 2.0(std. dev. 1), μ$_B$ (294K) | |
| Melting Pt. Range: | 154–159° C. | |
| C$_{25}$H$_{33}$N$_2$O$_2$TiCl$_2$ | | |
| Calculated: (%) | C 58.69  H 6.51  N 5.48 | |
| Measured: (%) | | |
| Sample 1 | C 56.86  H 5.89  N 3.77 | |
| Sample 2 | C 57.36  H 6.51  N 5.52 | |

Table Notes:
(Applicable for Tables 1A-6)
†-indicates analytical results for corresponding catalyst prepared using deuterated ligand, (Ph-d$_5$)$_2$nacnac(H).
$^a$-indicates solvent used for NMR measurements.
$^b$-indicates solvent used for IR measurements.
$^c$-indicates solvent used for UV-VIS measurements.
Letter designations after the numbers in the IR results provide an indication of the strength of the designated peak:
vs = very strong, s = strong, m = medium, and w = weak.

TABLE 1.A-2

Interatomic Distances and Angles for (Ph)$_2$nacnac TiCl$_2$(THF)$_2$

| Bond | Distance (Å) | Bond | Distance (Å) |
|---|---|---|---|
| Ti—N(1) | 2.086(3) | C(4)—C(5) | 1.366(6) |
| Ti—N(2) | 2.088(3) | C(5)—C(6) | 1.392(5) |
| Ti—O(2) | 2.209(3) | C(7)—C(9) | 1.386(5) |
| Ti—O(1) | 2.213(3) | C(7)—C(8) | 1.513(5) |
| Ti—Cl(1) | 2.3888(10) | C(9)—C(10) | 1.415(5) |
| Ti—Cl(2) | 2.4001(10) | C(10)—C(11) | 1.525(5) |
| N(1)—C(7) | 1.336(4) | C(12)—C(13) | 1.378(6) |
| N(1)—C(1) | 1.439(5) | C(12)—C(17) | 1.386(5) |
| N(2)—C(10) | 1.325(4) | C(13)—C(14) | 1.395(6) |
| N(2)—C(12) | 1.439(5) | C(14)—C(15) | 1.379(6) |
| O(1)—C(21) | 1.440(6) | C(15)—C(16) | 1.354(7) |
| O(1)—C(18) | 1.458(5) | C(16)—C(17) | 1.396(6) |
| O(2)—C(22) | 1.428(6) | C(18)—C(19) | 1.470(7) |
| O(2)—C(25) | 1.475(5) | C(19)—C(20) | 1.468(8) |
| C(1)—C(2) | 1.378(5) | C(20)—C(21) | 1.514(8) |
| C(1)—C(6) | 1.383(6) | C(22)—C(23) | 1.455(8) |
| C(2)—C(3) | 1.392(6) | C(23)—C(24) | 1.463(9) |
| C(3)—C(4) | 1.378(6) | C(24)—C(25) | 1.491(7) |

| Bond Angle | Angle (deg.) | Bond Angle | Angle (deg.) |
|---|---|---|---|
| N(1)—Ti—N(2) | 87.52(12) | C(6)—C(1)—N(1) | 119.9(3) |
| N(1)—Ti—O(2) | 176.65(12) | C(1)—C(2)—C(3) | 120.8(4) |
| N(2)—Ti—O(2) | 95.73(9) | C(4)—C(3)—C(2) | 119.4(4) |
| N(1)—Ti—O(1) | 95.39(10) | C(5)—C(4)—C(3) | 120.3(4) |
| N(2)—Ti—O(1) | 175.83(13) | C(4)—C(5)—C(6) | 120.4(4) |
| O(2)—Ti—O(1) | 81.40(11) | C(1)—C(6)—C(5) | 120.0(4) |
| N(1)—Ti—Cl(1) | 92.48(9) | N(1)—C(7)—C(9) | 123.9(3) |
| N(2)—Ti—Cl(1) | 89.35(10) | N(1)—C(7)—C(8) | 120.6(3) |
| O(2)—Ti—Cl(1) | 88.33(9) | C(9)—C(7)—C(8) | 115.5(3) |
| O(1)—Ti—Cl(1) | 87.55(8) | C(7)—C(9)—C(10) | 127.9(3) |
| N(1)—Ti—Cl(2) | 91.33(9) | N(2)—C(10)—C(9) | 124.1(3) |
| N(2)—Ti—Cl(2) | 94.06(10) | N(2)—C(10)—C(11) | 120.3(3) |
| O(2)—Ti—Cl(2) | 87.69(9) | C(9)—C(10)—C(11) | 115.6(3) |
| O(1)—Ti—Cl(2) | 88.86(8) | C(13)—C(12)—N(2) | 119.7(3) |
| Cl(1)—Ti—Cl(2) | 175.0(4) | C(17)—C(12)—N(2) | 120.9(4) |
| C(7)—N(1)—C(1) | 117.1(3) | C(12)—C(13)—C(14) | 120.5(4) |
| C(7)—N(1)—Ti | 127.4(2) | C(15)—C(14)—C(13) | 119.4(5) |
| C(1)—N(1)—Tith[001b] | 115.3(2) | | |
| C(10)—N(2)—C(12) | 116.8(3) | C(16)—C(15)—C(14) | 120.5(4) |
| C(10)—N(2)—Ti | 127.7(2) | C(15)—C(16)—C(17) | 120.7(4) |
| C(12)—N(2)—Ti | 115.2(2) | C(12)—C(17)—C(16) | 119.6(4) |
| C(21)—O(1)—C(18) | 106.5(3) | C(1)—C(18)—C(19) | 107.4(4) |
| C(21)—O(1)—Ti | 126.5(3) | C(20)—C(19)—C(18) | 108.0(4) |
| C(18)—O(1)—Ti | 126.7(3) | C(19)—C(20)—C(21) | 104.9(5) |
| C(22)—O(2)—C(25) | 107.1(3) | O(1)—C(21)—C(20) | 106.4(4) |
| C(22)—O(2)—Ti | 127.4(3) | O(2)—C(22)—C(23) | 108.2(5) |
| C(25)—O(2)—Ti | 125.2(3) | C(22)—C(23)—C(24) | 107.1(5) |

TABLE 1.A-2-continued

Interatomic Distances and Angles for (Ph)₂nacnac TiCl₂(THF)₂

| C(2)—C(1)—C(6) | 119.1(3) | C(23)—C(24)—C(25) | 103.2(5) |
|---|---|---|---|
| C(2)—C(1)—N(1) | 120.9(4) | O(2)—C(25)—C(24) | 106.0(5) |

(Note: the bond designations are with reference to FIG. 1 and the values noted in parentheses after the distances and angles represent the estimated standard deviation.)

TABLE 1A.3

Structure Determination Summary for (Ph)₂nacnacTiCl₂(THF)₂

Crystal Data

| | |
|---|---|
| Formula | $C_{25}H_{33}Cl_2N_2O_2Ti$ |
| Formula Weight | 512.33 |
| Crystal color | red |
| Crystal Size (mm) | 0.35 × 0.25 × 0.14 |
| Crystal System | orthorhombic |
| Space Group | Pna2₁ |
| Unit Cell Dimensions | a = 19.5601(8)Å |
| | b = 9.4959(4)Å |
| | c = 13.5555(5)Å |
| | α = 90° |
| | β = 90° |
| | γ = 90° |
| Volume | 2517.8(2)Å³ |
| Z | 4 |
| Density (calc.) | 1.352 g/cm³ |
| Absorption Coefficient | 5.76 cm⁻¹ |
| F(000) | 1076 |

Data collection

| | |
|---|---|
| Diffractometer Used | Siemens P4 |
| Radiation | MoKα(1 = 0.71073Å) |
| Temperature | 223(2)K |
| Monochromator | Highly oriented graphite crystal |
| 2θ Range (w) | 4.16 to 56.66 |
| Scan type | Omega, Phi |
| Scan Range | 0.3° |
| Index Ranges | −18 < h < 20 |
| | −12 < k < 11 |
| | −18 < l < 17 |
| Reflections Collected | 9097 |
| Independent Reflections | 4584 ($R_{int}$ = 3.41%) |
| Observed Reflections | 3916 |

Solution and Refinement

| | |
|---|---|
| System Used | SHELXTL (5.03) |
| Solution | Direct Methods |

TABLE 1A.3-continued

Structure Determination Summary for (Ph)₂nacnacTiCl₂(THF)₂

| | |
|---|---|
| Refinement Method | Full-Matrix Least-Squares |
| Quantity minimized | $S[w(F_o^2-F_c^2)^2]/S[(wF_o^2)^2]^{1/2}$ |
| Hydrogen Atoms | idealized contributions |
| Weighting Scheme | $w^{-1} = s^2(F) + 0.0010\ F^2$ |
| Final R Indices (obs. data) | R = 4.15%, wR = 10.51% |
| R Indices (all data) | R = 5.34%, wR = 11.50% |
| Goodness-of-Fit | 1.272 |
| Data-to-Parameter Ratio | 15.8:1 |
| Largest Difference Peak | 0.355 |
| Largest Difference Hole | −0.249 |

Example 1B

Preparation of 2,4-pentane di(N-phenyl)iminato Dichloro bis-tetrahydrofuran Vanadium, (Ph)₂nacnac VCl₂(THF)₂ and the Corresponding Compound with the Deuterated Ligand, (Ph-d₅)₂nacnac:

3.72 mmole (0.93 g) of (Ph)₂nacnac(H) was dissolved in 50 ml of THF and cooled to −30° C. in a round bottom flask. 3.72 mmoles MeLi solution was added slowly and allowed to stir for two hours to give a yellow solution of (Ph)₂nacnacLi in THF with gas evolution. After the reaction mixture was allowed to stir until no more bubbles were observed, it was cooled to −30° C. In a separate round bottom flask, 3.72 mmoles (1.37 g) of VCl₃(THF)₃ was dissolved in 150 ml of THF. The THF solution of (Ph)₂nacnacLi was then transferred to an addition funnel and added dropwise to the THF solution of VCl₃(THF)₃ over a three hour period. The color of the solution slowly changed from dark red to purple brown and finally dark green. After stirring overnight, the solvent was evaporated to dryness. The resulting brown solid, was extracted with toluene, by trituration in ether. The brown solution was then filtered and toluene was vacuum removed. The solid was dissolved in THF which turned dark green. The THF solution was cooled to −30° C. for crystallization. Dark green microcrystalline powder was isolated by filtration and washed with cold THF several times. After drying under vacuum, 1.05 g (55% yield) of (Ph)₂nacnacVCl₂(THF)₂ was isolated.

Figure 2:
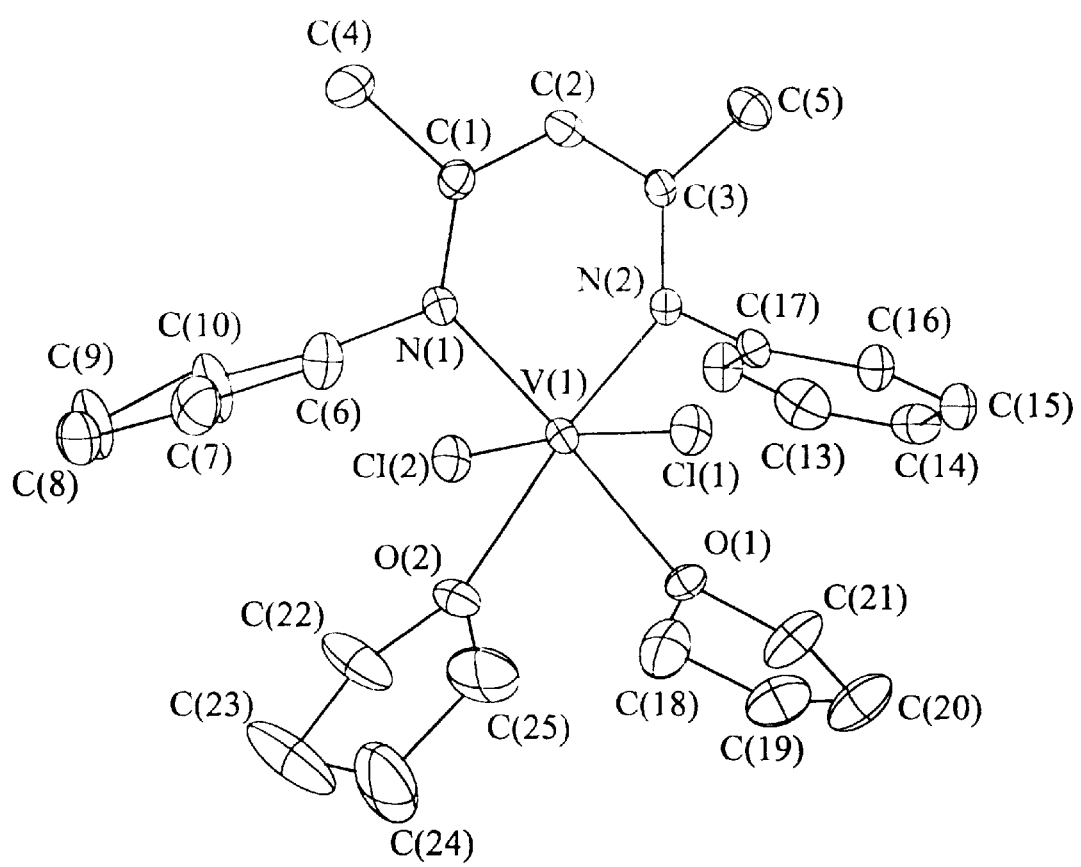
FIG. 2 depicts the crystal structure of the (Ph)$_2$ nacnacVCl$_2$(THF)$_2$, prepared in Example 1B.

The resulting compounds were analytically tested and the results are shown in Tables 1B.1–3. The single crystal X-ray diffraction results are shown in FIG. 2.

TABLE 1B.1

ANALYTICAL DATA FOR (Ph)₂nacnacVCl₂(THF)₂ (Ph-d₅)₂nacnacVCl₂(THF)₂

| | | | | | | | |
|---|---|---|---|---|---|---|---|
| ¹H NMR(CD₂Cl₂)ᵃ: δ (ppm) | 111.52 (2H, b) | 99.81 (2H, b) | 86.72 (1H, b) | 25-8 (4H, vb) | 8.49 (1H) | 5.55 (11H, b) | 1.83 (8H) |
| ¹H NMR(THF-d₈)ᵃ: δ (ppm) | 107.59 (6H) | 86.92 (1H) | 12.22 (4H) | 6.23 (6H) | *** | *** | *** |
| ¹H NMR (THF-d₈)ᵃ: † δ (ppm) | 108.76 (6H) | 85.80 (1H) | *** | *** | *** | *** | *** |
| ²H NMR (THF)ᵃ: δ (ppm) | 12.1 (4D) | 6.2 (6D) | *** | *** | *** | *** | *** |
| IR-KBrᵇ: (cm⁻¹): | 3053 m 1485 m 924 s | 3031 m 1435 s 920 m | 2928 s 1430 m 875 s | 2927 m 1368 m 844 s | 2879 m 1319 s 784 w | 1590 m 1066 w 779 m | 1532 s 1021 s 708 s 524 w |
| IR-KBrᵇ: (cm⁻¹): † | 2968 m 1382 vs 811 w | 2927 m 1318 vs 779 w | 2876 m 1242 vs 556 m | 2269 w 1021 s 457 m | 1561 m 924 w *** | 1528 vs 870 m *** | 1430 m 854 m *** |

TABLE 1B.1-continued

ANALYTICAL DATA FOR
(Ph)$_2$nacnacVCl$_2$(THF)$_2$
(Ph-d$_5$)$_2$nacnacVCl$_2$(THF)$_2$

| | | |
|---|---|---|
| Mass Spectrometry: m/z (%) | 369.99(37)[M$^+$-(THF)$_2$] | 299.04(32) [M$^+$-Cl(THF)$_2$] |
| Mass Spectrometry:† m/z (%) | 380.02(100.0)[M$^+$-(THF)$_2$] | 345.05(2.54) [M$^+$-Cl(THF)$_2$] |
| UV-vis (THF)$^c$: λ$_{max}$(ε) | 598(1,318.4 M$^{-1}$cm$^{-1}$) | 474(1,404.2 M$^{-1}$ cm$^{-1}$) 350(10,574.7 M$^{-1}$ cm$^{-1}$) |
| μ$_{eff}$ | 3.2(std. dev. 1), μ$_B$ (294K) | |
| Melting Pt. Range: | 162–164° C. | |
| C$_{25}$H$_{33}$N$_2$O$_2$VCl$_2$ | | |
| Calculated: (%) | C 58.26  H 6.45  N 5.44 | |
| Measured: (%) | C 57.81  H 6.37  N 3.77 | |

TABLE 1B.2

Interatomic Distances and Angles for (Ph)$_2$nacnacVCl$_2$(THF)$_2$

| Bond | Distance (Å) | Bond | Distance (Å) |
|---|---|---|---|
| V(1)—N(1) | 2.023(2) | C(6)—C(11) | 1.382(4) |
| V(1)—N(2) | 2.030(2) | C(7)—C(8) | 1.379(5) |
| V(1)—O(1) | 2.208(2) | C(8)—C(9) | 1.366(5) |
| V(1)—O(2) | 2.221(2) | C(9)—C(10) | 1.393(4) |
| V(1)—Cl(1) | 2.3592(6) | C(10)—C(11) | 1.389(3) |
| V(1)—Cl(2) | 2.3646(6) | C(12)—C(13) | 1.383(4) |
| O(1)—C(21) | 1.445(4) | C(12)—C(17) | 1.385(4) |
| O(1)—C(18) | 1.456(4) | C(13)—C(14) | 1.397(4) |
| O(2)—C(25) | 1.447(4) | C(14)—C(15) | 1.382(4) |
| O(2)—C(22) | 1.480(4) | C(15)—C(16) | 1.386(4) |
| N(1)—C(1) | 1.345(3) | C(16)—C(17) | 1.393(4) |
| N(1)—C(11) | 1.430(3) | C(18)—C(19) | 1.506(5) |
| N(2)—C(3) | 1.337(3) | C(19)—C(20) | 1.471(6) |
| N(2)—C(17) | 1.431(3) | C(20)—C(21) | 1.488(5) |
| C(1)—C(2) | 1.400(3) | C(22)—C(23) | 1.518(5) |
| C(1)—C(4) | 1.523(4) | C(23)—C(24') | 1.39(2) |
| C(2)—C(3) | 1.395(4) | C(23)—C(24) | 1.559(13) |
| C(3)—C(5) | 1.509(3) | C(24)—C(25) | 1.383(10) |
| C(6)—C(7) | 1.380(4) | C(24')—C(25) | 1.597(12) |

| Bond Angle | Angle (deg.) | Bond Angle | Angel (deg.) |
|---|---|---|---|
| N(1)—V(1)—N(2) | 90.94(9) | N(2)—C(3)—C(2) | 123.5(2) |
| N(1)—V(1)—O(2) | 94.15(7) | N(2)—C(3)—C(5) | 120.6(2) |
| N(2)—V(1)—O(2) | 174.89(9) | C(2)—C(3)—C(5) | 115.8(2) |
| N(1)—V(1)—O(1) | 174.75(9) | C(7)—C(6)—C(11) | 120.9(3) |
| N(2)—V(1)—O(1) | 93.45(7) | C(8)—C(7)—C(6) | 120.0(3) |
| O(2)—V(1)—O(1) | 81.44(8) | C(9)—C(8)—C(7) | 119.8(3) |
| N(1)—V(1)—Cl(1) | 89.68(7) | C(8)—C(9)—C(10) | 120.7(3) |
| N(2)—V(1)—Cl(1) | 91.35(7) | C(11)—C(10)—C(9) | 119.7(3) |
| O(2)—V(1)—Cl(1) | 88.24(7) | C(6)—C(11)—C(10) | 118.9(3) |
| O(1)—V(1)—Cl(1) | 87.33(6) | C(6)—C(11)—N(1) | 120.2(2) |
| N(1)—V(1)—Cl(2) | 93.78(7) | C(10)—C(11)—N(1) | 120.8(2) |
| N(2)—V(1)—Cl(2) | 92.22(7) | C(13)—C(12)—C(17) | 121.0(3) |
| O(2)—V(1)—Cl(2) | 87.90(7) | C(12)—C(13)—C(14) | 119.6(3) |
| O(1)—V(1)—Cl(2) | 88.93(6) | C(15)—C(14)—C(13) | 119.8(3) |
| Cl(1)—V(1)—Cl(2) | 174.99(3) | C(14)—C(15)—C(16) | 120.2(3) |
| C(21)—O(1)—C(18) | 106.5(2) | C(15)—C(16)—C(17) | 120.4(3) |
| C(21)—O(1)—V(1) | 126.8(2) | C(12)—C(17)—C(16) | 119.0(3) |
| C(18)—O(1)—V(1) | 125.8(2) | C(12)—C(17)—N(2) | 120.3(2) |
| C(25)—O(2)—C(22) | 108.2(3) | C(16)—C(17)—N(2) | 120.7(2) |
| C(25)—O(2)—V(1) | 126.5(2) | O(1)—C(18)—C(19) | 105.9(3) |
| C(22)—O(2)—V(1) | 125.0(2) | C(20)—C(19)—C(18) | 106.0(3) |
| C(1)—N(1)—C(11) | 116.4(2) | C(19)—C(20)—C(21) | 107.0(3) |
| C(1)—N(1)—V(1) | 126.2(2) | O(1)—C(21)—C(20) | 107.2(3) |
| C(11)—N(1)—V(1) | 117.1(2) | O(2)—C(22)—C(23) | 104.8(3) |
| C(3)—N(2)—C(17) | 117.6(2) | C(24')—C(23)—C(22) | 102.0(7) |
| C(3)—N(2)—V(1) | 125.8(2) | C(22)—C(23)—C(24) | 105.5(5) |
| C(17)—N(2)—V(1) | 116.4(2) | C(25)—C(24)—C(23) | 106.9(7) |
| N(1)—C(1)—C(2) | 123.3(2) | C(23)—C(24')—C(25) | 104.7(6) |
| N(1)—C(1)—C(4) | 120.3(2) | C(24)—C(25)—O(2) | 110.7(5) |
| C(2)—C(1)—C(4) | 116.4(2) | O(2)—C(25)—C(24') | 102.3(7) |
| C(3)—C(2)—C(1) | 128.8(2) | | |

(Note:
the bond designations are with reference to FIG. 2 and the values noted in parentheses after the distances and angles represent the estimated standard deviation.)

TABLE 1B.3

Structure Determination Summary for (Ph)$_2$nacnacVCl$_2$(THF)$_2$

| Crystal Data | |
|---|---|
| Formula | C$_{25}$H$_{33}$Cl$_2$N$_2$O$_2$V |
| Formula weight | 515.37 |
| Crystal color | black block |
| Crystal Size (mm) | 0.35 × 0.25 × 0.14 |
| Crystal System | orthorhombic |
| Space Group | Pna2$_1$ |
| Unit Cell Dimensions | a = 19.515(4)Å |
| | b = 9.5341(2)Å |
| | c = 13.4898(3)Å |
| | α = 90° |
| | β = 90° |
| | γ = 90° |
| Volume | 2510.72(9)Å$^3$ |
| Z | 4 |
| Density (calc.) | 1.363 g/cm$^3$ |
| Absorption Coefficient | 6.32 cm$^{-1}$ |
| F(000) | 1080 |
| Data collection | |
| Diffractometer | Siemens P4 |
| Radiation | MoKα(1 = 0.71073Å) |
| Temperature | 218(2)K |
| Monochromator | Highly oriented graphite crystal |
| 2θ Range (w) | 4.16 to 56.56° |
| Scan type | Omega, Phi |
| Scan Range | 0.3° |
| Index Ranges | −25 < h < 12 |
| | −10 < k < 12 |
| | −17 < l < 17 |
| Reflections Collected | 9021 |
| Independent Reflections | 5585 (R$_{int}$ = 2.04%) |
| Observed Reflections | 4948 |
| Solution and Refinement | |
| System Used | SHELXTL (5.03) |
| Solution | Direct Methods |
| Refinement Method | Full-Matrix Least-Squares |
| Quantity minimized | S[w(F$_o^2$—F$_c^2$)$^2$]/S[(wF$_o^2$)$^2$]$^{1/2}$ |
| Hydrogen Atoms | Idealized contributions |

TABLE 1B.3-continued

Structure Determination Summary for $(Ph)_2nacnacVCl_2(THF)_2$

| | |
|---|---|
| Weighting Scheme | $w^{-1} = s^2(F) + 0.0010\ F^2$ |
| Final R Indices (obs. data) | R = 3.75%, wR = 8.23% |
| R Indices (all data) | R = 4.67%, wR = 9.77% |
| Goodness-of-Fit | 1.390 |
| Data-to-Parameter Ratio | 18.6:1 |
| Largest Difference Peak | 0.301 |
| Largest Difference Hole | −0.240 |

Example 1C

Preparation of 2,4-pentane di(N-phenyl)iminato Dichloro bis-tetrahydrofuran Chromium, $(Ph)_2nacnacCrCl_2(THF)_2$ and the Corresponding Compound with the Deuterated Ligand, $(Ph-d_5)_2nacnac$:

2.40 mmole (0.6 g,) of $(Ph)_2nacnacH$ was dissolved in 50 ml of THF and cooled to −30° C. 2.40 mmoles (53 mg) of MeLi was slowly added as a solid with stirring. The THF solution of $(Ph)_2nacnacLi$ prepared in-situ was then slowly added over a three hour period to a slurry of 2.40 mmoles (900 mg,) of $CrCl_3(THF)_3$ in 150 ml of THF. The color of the solution changed from a purple to red brown. After stirring at room temperature overnight, the reaction mixture was concentrated to 50 ml and cooled to −30° C. for crystallization. A brown microcrystalline powder was isolated by filtration. After washing with cold THF several times and drying under vacuum, 2.09 mmoles (1.08 g, 87% yield) of the resulting $(Ph)_2nacnacCrCl_2(THF)_2$ compound was isolated.

Figure 3:
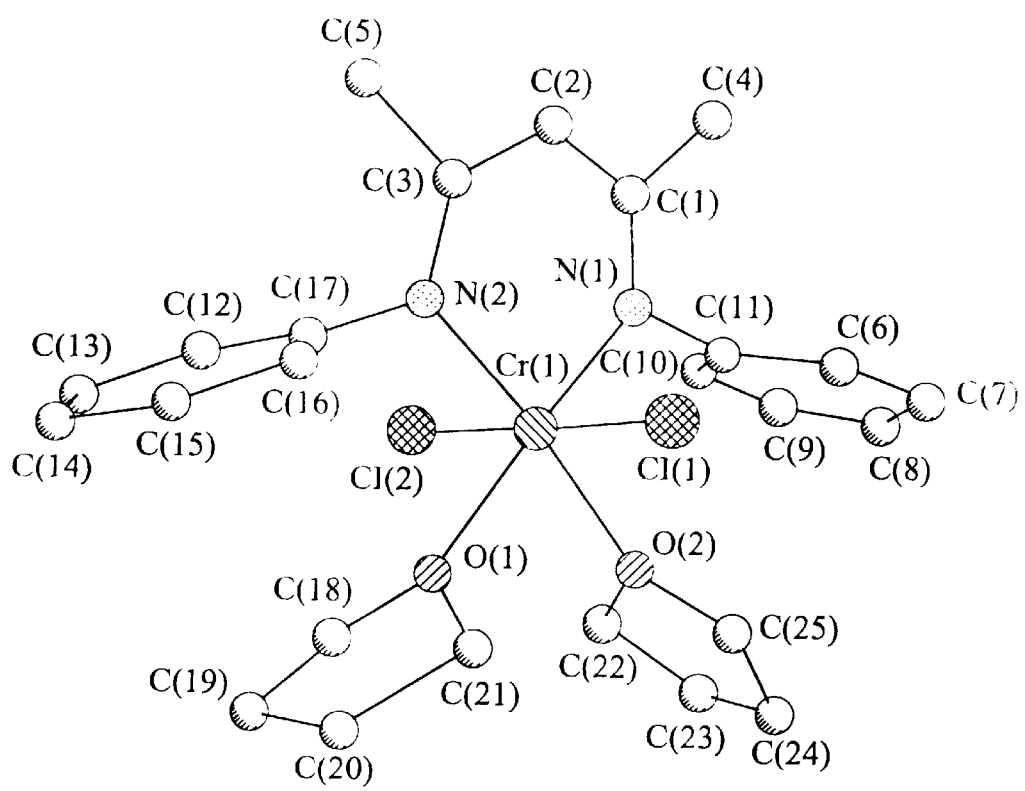
FIG. 3 depicts the crystal structure of the (Ph)$_2$ nacnacCrCl$_2$(THF)$_2$, prepared in Example 1C.

The resulting compounds were analytically tested and the results are shown in Tables 1C.1–3. The single crystal X-ray diffraction results are shown in FIG. 3.

TABLE 1C.1

ANALYTICAL DATA FOR
$(Ph)_2nacnacCrCl_2(THF)_2$
$(Ph-d_5)_2nacnacCrCl_2(THF)_2$

| | | | | | | | |
|---|---|---|---|---|---|---|---|
| $^1$H NMR(CD$_2$Cl$_2$)$^a$: δ (ppm) | 111.52 (2H, b) | 99.81 (2H, b) | 86.72 (1H, b) | 25-8 (4H, vb) | 8.49 (1H) | 5.55 (11H, b) | 1.83 (8H) |
| $^1$H NMR(THF-d$_8$)$^a$: δ (ppm) | 15.46 (6H) | 6.19 (4H) | 12.22 (4H) | 6.23 (6H) | *** | *** | *** |
| $^1$H NMR (THF-d$_8$)$^a$: † δ (ppm) | 16.1 (4D) | 15.4 (2D) | 6.1 (4D) | *** | *** | *** | *** |
| IR-KBr$^b$: (cm$^{-1}$): | 3050 w  3017 m  2966 s  2928 s  2883 s  1590 w  1555 vs 1530 vs  1484 vs  1448 vs  1387 vs  1263 s  1200 s  1065 w  1017 s 921 m  871 m  848 s  764 m  710 s  662 w  526 m  477 w | | | | | | |
| IR-KBr$^b$: (cm$^{-1}$): † | 2967 m  2926 m  2878 m  2269 m  1550 m  1528 vs  1430 m 1381 vs  1320 vs  1157 m  1016 m  969 w  869 m  855 m 811 w  753 m  558 m  427 m  ***  ***  *** | | | | | | |
| UV-vis(THF)$^c$: $\lambda_{max}(\epsilon)$ | 598(1,318.4 M$^{-1}$ cm$^{-1}$) | | 474(1,404,2 M$^{-1}$ cm$^{-1}$) | | | 350(10,574.7 M$^{-1}$ cm$^{-1}$) | |
| Mass Spectrometry: m/z (%) | 370.76(41.24) [M$^+$-(THF)$_2$] | | 335.81(41.60) [M$^+$-Cl(THF)$_2$] | | | 300.86(6.01) [M$^+$-Cl$_2$(THF)$_2$] | |
| Mass Spectrometry:† m/z (%) | 381.02(19.41) [M$^+$-(THF)$_2$] | | 346.05(46.83) [M$^+$-Cl(THF)$_2$] | | | 311.09(5.45) [M$^+$-Cl$_2$(THF)$_2$] | |
| UV-vis (THF)$^c$: $\lambda_{max}(\epsilon)$ | 527(572.2 M$^{-1}$ cm$^{-1}$) | | 419(8,232.5 M$^{-1}$ cm$^{-1}$) | | | 400(5,711.7 M$^{-1}$cm$^{-1}$) | |
| $\mu_{eff}$ | 4.1(std. dev. 1), $\mu_B$ (294K) | | | | | | |
| Melting Pt. Range: | 174–180° C. | | | | | | |
| $C_{25}H_{33}N_2O_2CrCl_2$ | | | | | | | |
| Calculated: (%) | C 58.14   H 6.44   N 5.42 | | | | | | |
| Measured: (%) | C 57.95   H 6.81   N 5.51 | | | | | | |

TABLE 1C.2

Interatomic Distances and Angles for $(Ph)_2nacnacCrCl_2(THF)$
(Note: the bond designations are with reference to FIG. 3 and the values noted in parentheses after the distances and angles represent the estimated standard deviation.)

| Bond | Distance (Å) | Bond | Distance (Å) |
|---|---|---|---|
| Cr(1)—N(1) | 2.032(6) | C(6)—C(7) | 1.398(7) |
| Cr(1)—N(2) | 2.033(5) | C(7)—C(8) | 1.415(8) |
| Cr(1)—O(2) | 2.141(5) | C(8)—C(9) | 1.347(9) |
| Cr(1)—O(1) | 2.144(5) | C(9)—C(10) | 1.402(8) |
| Cr(1)—Cl(1) | 2.3392(12) | C(10)—C(11) | 1.415(7) |
| Cr(1)—Cl(2) | 2.3532(12) | C(12)—C(17) | 1.369(7) |
| O(1)—C(18) | 1.462(8) | C(12)—C(13) | 1.406(8) |
| O(1)—C(21) | 1.464(8) | C(13)—C(14) | 1.383(8) |
| O(2)—C(25) | 1.459(8) | C(14)—C(15) | 1.393(8) |
| O(2)—C(22) | 1.473(8) | C(15)—C(16) | 1.374(8) |
| N(1)—C(1) | 1.315(8) | C(16)—C(17) | 1.424(7) |
| N(1)—C(11) | 1.459(7) | C(18)—C(19) | 1.526(9) |
| N(2)—C(3) | 1.323(8) | C(19)—C(20) | 1.519(11) |
| N(2)—C(17) | 1.453(7) | C(20)—C(21) | 1.492(10) |
| C(1)—C(2) | 1.431(7) | C(22)—C(23) | 1.497(10) |
| C(1)—C(4) | 1.537(8) | C(23)—C(24') | 1.40(3) |

TABLE 1C.2-continued

Interatomic Distances and Angles for $(Ph)_2nacnacCrCl_2(THF)$
(Note: the bond designations are with reference to FIG. 3 and the values noted in parentheses after the distances and angles represent the estimated standard deviation.)

| | | | |
|---|---|---|---|
| C(2)—C(3) | 1.412(8) | C(23)—C(24) | 1.58(2) |
| C(3)—C(5) | 1.525(8) | C(24)—C(25) | 1.47(2) |
| C(6)—C(11) | 1.377(8) | C(24')—C(25) | 1.50(3) |

| Bond Angle | Angle (deg.) | Bond Angle | Angle (deg.) |
|---|---|---|---|
| N(1)—Cr(1)—N(2) | 91.7(2) | N(2)—C(3)—C(2) | 124.7(5) |
| N(1)—Cr(1)—O(2) | 93.4(2) | N(2)—C(3)—C(5) | 121.2(6) |
| N(2)—Cr(1)—O(2) | 174.8(2) | C(2)—C(3)—C(5) | 114.1(6) |
| N(1)—Cr(1)—O(1) | 176.0(2) | C(11)—C(6)—C(7) | 121.7(5) |
| N(2)—Cr(1)—O(1) | 92.1(2) | C(6)—C(7)—C(8) | 118.0(5) |
| O(2)—Cr(1)—O(1) | 82.7(2) | C(9)—C(8)—C(7) | 120.5(6) |
| N(1)—Cr(1)—Cl(1) | 88.5(2) | C(8)—C(9)—C(10) | 122.2(6) |
| N(2)—Cr(1)—Cl(1) | 89.5(2) | C(9)—C(10)—C(11) | 118.0(6) |
| O(2)—Cr(1)—Cl(1) | 90.1(2) | C(6)—C(11)—C(10) | 119.6(5) |
| O(1)—Cr(1)—Cl(1) | 90.28(13) | C(6)—C(11)—N(1) | 121.1(5) |
| N(1)—Cr(1)—Cl(2) | 90.6(2) | C(10)—C(11)—N(1) | 119.1(5) |
| N(2)—Cr(1)—Cl(2) | 90.1(2) | C(17)—C(12)—C(13) | 120.8(5) |
| O(2)—Cr(1)—Cl(2) | 90.3(2) | C(14)—C(13)—C(12) | 119.8(5) |
| O(1)—Cr(1)—Cl(2) | 90.71(13) | C(13)—C(14)—C(15) | 119.5(6) |
| C(1)—Cr(1)—Cl(2) | 178.95(11) | C(16)—C(15)—C(14) | 121.3(5) |
| C(18)—O(1)—C(21) | 106.3(6) | C(15)—C(16)—C(17) | 119.3(5) |
| C(18)—O(1)—Cr(1) | 126.5(4) | C(12)—C(17)—C(16) | 119.3(5) |
| C(21)—O(1)—Cr(1) | 125.8(4) | C(12)—C(17)—N(2) | 121.6(5) |
| C(25)—O(2)—C(22) | 107.4(6) | C(16)—C(17)—N(2) | 119.0(5) |
| C(25)—O(2)—Cr(1) | 126.9(4) | O(1)—C(18)—C(19) | 105.9(6) |
| C(22)—O(2)—Cr(1) | 125.2(5) | O(20)—C(19)—C(18) | 103.8(6) |
| C(1)—N(1)—C(11) | 117.1(5) | C(21)—C(20)—C(19) | 107.4(6) |
| C(1)—N(1)—Cr(1) | 125.7(4) | C(1)—C(21)—C(20) | 106.8(6) |
| C(11)—N(1)—Cr(1) | 116.8(4) | C(2)—C(22)—C(23) | 105.8(7) |
| C(3)—N(2)—C(17) | 117.7(5) | C(24')—C(23)—C(22) | 100.4(12) |
| C(3)—N(2)—Cr(1) | 125.3(4) | C(22)—C(23)—C(24) | 109.4(9) |
| C(17)—N(2)—Cr(1) | 117.0(4) | C(25)—C(24)—C(23) | 101.3(13) |
| N(1)—C(1)—C(2) | 124.6(6) | C(23)—C(24')—C(25) | 109(2) |
| N(1)—C(1)—C(4) | 121.2(5) | C(24)—C(25)—O(2) | 112.3(10) |
| C(2)—C(1)—C(4) | 114.2(6) | O(2)—C(25)—C(24') | 103(2) |
| C(3)—C(2)—C(1) | 126.9(6) | | |

TABLE 1C.3

Structure Determination Summary for $(Ph)_2nacnacCrCl_2(THF)$

Crystal Data

| | |
|---|---|
| Empirical Formula | $C_{25}H_{33}Cl_2N_2O_2Cr$ |
| Color; Habit | brown plate |
| Crystal Size (mm) | 0.35 × 0.35 × 0.12 |
| Crystal System | orthorhombic |
| Space Group | $Pna2_1$ |
| Unit Cell Dimensions | a = 19.6220(4) Å |
| | b = 9.5971(2) Å |
| | c = 13.4509(3) Å |
| | α = 90° |
| | β = 90° |
| | γ = 90° |
| Volume | 2533.00(9) Å$^3$ |
| Z | 4 |
| Formula Weight | 516.43 |
| Density (calc.) | 1.354 g/cm$^3$ |
| Absorption Coefficient | 6.87 cm$^{-1}$ |
| F(000) | 1084 |

Data Collection

| | |
|---|---|
| Diffractometer Used | Siemens P4/CCD |
| Radiation | MoKα (l = 0.71073 Å) |
| Temperature | 218(2) K |
| Monochromator | Highly oriented graphite crystal |
| 2θ Range (w) | 4.16 to 56.12° |
| Scan type | Omega, Phi |
| Scan With | 0.3° |

TABLE 1C.3-continued

Structure Determination Summary for $(Ph)_2nacnacCrCl_2(THF)$

| | |
|---|---|
| Index Ranges | −24 < h < 25 |
| | −12 < k < 12 |
| | −16 < l < 13 |
| Reflections Collected | 9160 |
| Independent Reflections | 4228 ($R_{int}$ = 13.02%) |
| Observed Reflections | 2408 |

Solution and Refinement

| | |
|---|---|
| System Used | SHELXTL (5.03) |
| Solution | Direct Methods |
| Refinement Method | Full-Matrix Least-Squares |
| Quantity minimized | $S[w(F_o^2 - F_c^2)^2]/S[(wF_o^2)^2]^{1/2}$ |
| Hydrogen Atoms | Idealized contributions |
| Weighting Scheme | $w^{-1} = s^2(F) + 0.0010F^2$ |
| Final R Indices (obs. data) | R = 5.35%, wR = 11.14% |
| R Indices (all data) | R = 10.56%, wR = 16.45% |
| Goodness-of-Fit | 0.808 |
| Data-to-Parameter Ratio | 14.2:1 |
| Largest Difference Peak | 0.375 |
| Largest Difference Hole | −0.880 |

Example 2A

Preparation of 2,4-pentane di(N-phenyl)iminato Chloro Methyl Vanadium, $(Ph)_2nacnacV(Cl)(Me)$:

0.97 mmoles (0.500 g) of $(Ph)_2nacnacVCl_2(THF)_2$, reference Example 1B, was dissolved in 150 ml of THF and the solution was cooled to −30° C. 0.97 mmoles of MeLi in ether was slowly added to the suspension of $(Ph)_2$ nacnacVCl$_2$(THF)$_2$ in THF which caused a color change from dark green to dark red brown. After stirring for 5 hours, the reaction mixture was evaporated to dryness. The residual THF was removed by trituration in ether. The brown solid was then extracted with ether and filtered to remove LiCl. The ether solution was concentrated and cooled to −30° C. for crystallization. A microcrystalline brown powder was filtered and washed with cold pentane. After drying under vacuum, 0.202 g (59% yield) of $(Ph)_2nacnacV(Cl)(Me)$ was isolated. The resulting compound was analytically tested and the results are shown in Table 2A.

TABLE 2A

ANALYTICAL DATA FOR $(Ph)_2nacnacV(Cl)(Me)$

| $^1H\ NMR(C_6D_6)^a$: | 8.70 | −3.90 | *** | *** | *** | *** | *** |
|---|---|---|---|---|---|---|---|
| δ (ppm) | (6H, vb) | (2H, vb) | | | | | |
| IR-KBr$^b$: (cm$^{-1}$) | 3057 w | 3029 w | 2992 w | 2959 w | 2918 w | 2848 w | 1592 m |
| | 1530 s | 1510 m | 1483 s | 1447 m | 1427 m | 1371 s | 1339 s |
| | 1299 m | 1262 m | 1184 w | 1071 w | 1023 m | 1023 s | 997 m |
| | 937 w | 918 w | 854 w | 799 w | 754 s | 700 s | 515 m |
| Mass Spectrometry: m/z (%) | 350(15) [M$^+$] | | 335(100) [M$^+$—CH$_2$] | | | 299(6) [M$^+$—CH$_3$CL] | |
| UV-vis (Et$_2$O):$^c$ λ$_{max}$(ε) | 541(4.27 × 10$^4$ M$^{-1}$ cm$^{-1}$) | | | | 435(1.42 × 10$^5$ M$^{-1}$ cm$^{-1}$) | | |
| μ$_{eff}$ | 3.0(std. dev. 1), μ$_B$ (294K) | | | | | | |
| Melting Pt. Range: | 132–134° C. | | | | | | |
| C$_{18}$H$_{20}$N$_2$VCl | | | | | | | |
| Calculated: (%) | C 61.64 | H 5.75 | N 7.99 | | | | |
| Measured: (%) | C 61.53 | H 5.74 | N 7.98 | | | | |

Example 2B
Preparation of 2,4-pentane di(N-phenyl)iminato Chloro Trimethylsilylmethyl Vanadium, $(Ph)_2nacnacV(Cl)(CH_2Si(CH_3)_3)$:

0.58 mmoles (300 mg) of $(Ph)_2nacnacVCl_2(THF)_2$, reference Example 1B, was dissolved in 50 ml of diethylether and the solution was cooled to −30° C. 0.58 mmoles of $LiCH_2Si(CH_3)_3$ in a diethylether solution was added slowly to the $(Ph)_2nacnacVCl_2(THF)_2$ in diethylether solution which clouded the brown solution without an observable color change. After stirring overnight at room temperature, the reaction mixture was evaporated to dryness. The dark brown oil was dissolved in pentane and evaporated to dryness twice to remove residual THF. The solid was then extracted with pentane and filtered to remove LiCl. The solvent was again evaporated and the dark red brown oil was dissolved in a minimum amount of HMDS with some drops of pentane and cooled to −30° C. for crystallization. 124 mg (505 yield) of dark brown $(Ph)_2nacnacV(Cl)(CH_2Si(CH_3)_3$ crystals were isolated after two crystallization extraction cycles. The crystals were analytically tested and the results are shown in Table 2B.

Example 3A

Preparation of 2,4-pentane di(N-phenyl)iminato Dimethyl Vanadium, $(Ph)_2nacnacVMe_2$:

5.0 mmoles (2.58 g,) of $(Ph)_2nacnacVCl_2(THF)_2$, reference Example 1B, was suspended in 150 ml of THF and cooled to −30°. 11.0 mmoles (2.2 equiv.) of MeLi was added slowly causing a color change from dark green to dark brown. After stirring for 5 hours, the reaction mixture was evaporated to dryness. The brown solid was dissolved in diethylether and evaporated to dryness twice to remove residual THF. The solid was then extracted with diethlyether and filtered to remove LiCl. The solution was concentrated to 30 ml of ether and cooled to −30° C. for crystallization. 1.397 g of brown cubic $(Ph)_2nacnacVMe_2$ crystals containing chloride impurity of $(Ph)_2nacnacV(Cl)(Me)$ were isolated after vacuum drying. The content of the chloride impurity ranges from 18 to 50%.

Figure 4:
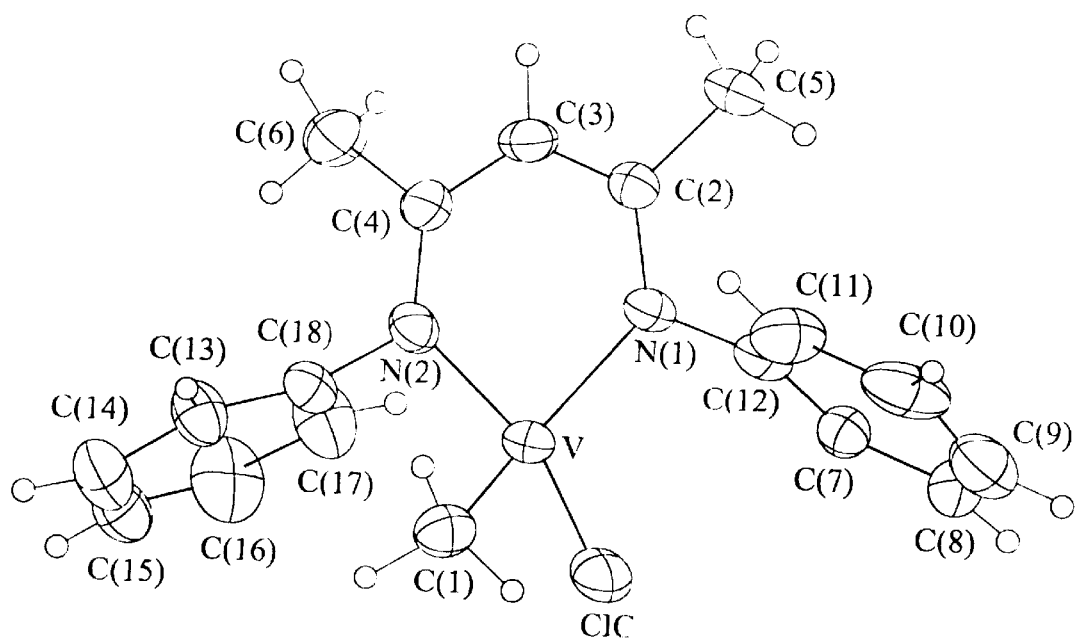
FIG. 4 depicts the crystal structure of the (Ph)$_2$ nacnacVMe$_2$, prepared in Example 3A.

The resulting compounds were analytically tested and the results are shown in Tables 3A.1–3. The single crystal X-ray diffraction results are shown in FIG. 4.

TABLE 2B

ANALYTICAL DATA FOR $(Ph)_2nacnacV(Cl)(CH_2Si(CH_3)_3)$

| $^1H\ NMR(C_6D_6)$:$^a$ | 8.69 | −1.40 | 3.16 | *** | *** | *** | *** |
|---|---|---|---|---|---|---|---|
| δ (ppm) | (6H) | (9H) | (2H) | | | | |
| IR-KBr$^b$: (cm$^{-1}$) | 3056 w | 3026 w | 2999 w | 2956 m | 2922 m | 2850 w | 1593 m |
| | 1532 s | 1510 m | 1485 s | 1447 m | 1431 m | 1371 vs | 1299 m 1251 m |
| | 1071 w | 1022 m | 998 m | 848 s | 757 m | 701 s | 488 w 471 w |
| Mass Spectrometry: m/z (%) | | | 422(7) [M$^+$] | | | 335(57) [M$^+$-CH$_2$Si(CH$_3$)$_3$] | |
| UV-vis (Et$_2$O):$^c$ λ$_{max}$(ε) | | | 541(266 M$^{-1}$ cm$^{-1}$) | | | 629(421 M$^{-1}$ cm$^{-1}$) | |
| μ$_{eff}$ | | | 3.0(std. dev. 1), μ$_B$ (294K) | | | | |
| Melting Pt. Range: | | | 250–254° C. | | | | |
| C$_{21}$H$_{28}$N$_2$ClVSi | | | | | | | |
| Calculated: (%) | C 59.70 | H 6.69 | N 6.63 | | | | |
| Measured: (%) | C 59.59 | H 6.58 | N 6.39 | | | | |

TABLE 3A.1

ANALYTICAL DATA FOR (Ph)$_2$nacnacVMe$_2$

| $^1$H NMR(C$_6$D$_6$)$^a$:<br>δ (ppm) | 8.68<br>(6H) | −4.99<br>(2H) | *** | *** | *** | *** | *** |
|---|---|---|---|---|---|---|---|
| IR-KBr$^b$: (cm-1) | 3053 m | 3031 m | 2968 s | 2927 m | 2879 m | 1590 m | 1532 s |
| | 1485 s | 1435 m | 1430 m | 1368 m | 1319 s | 1066 w | 1021 s |
| | 924 w | 920 m | 875 s | 844 s | 784 w | 779 m | 708 s | 524 w |
| Mass Spectrometry:<br>m/z (%) | 330(23.4)<br>[M$^+$] | | | 315(22.29)<br>[M$^+$-CH$_3$] | | 300(29.24)<br>[M$^+$-2 CH$_3$] | |
| UV-vis (Et$_2$O)$^c$:<br>λ$_{max}$(ε) | 597(194.4 M$^{-1}$ cm$^{-1}$) | | | | 446(334 M$^{-1}$ cm$^{-1}$) | | |
| μ$_{eff}$ | 3.1(std. dev. 1), μ$_B$ (294K) | | | | | | |
| Melting Pt. Range: | 125–129° C. | | | | | | |
| C$_{19}$H$_{23}$N$_2$V | | | | | | | |
| Calculated: (%) | C 69.08 | H 7.02 | N 8.48 | | | | |
| Measured: (%) | C 64.76 | H 6.36 | N 8.29 | | | | |

TABLE 3A.2

Interatomic Distances and Angles for (Ph)$_2$nacnacVMe$_2$
(Note: the bond designations are with reference to FIG. 4 and the values noted in parentheses after the distances and angles represent the estimated standard deviation.)

| Bond | Distance (Å) | Bond | Distance (Å) |
|---|---|---|---|
| V—N(1) | 1.963(3) | C(7)—C(8) | 1.398(5) |
| V—N(2) | 1.972(3) | C(7)—C(12) | 1.415(6) |
| V—C(1) | 2.080(4) | C(8)—C(9) | 1.387(6) |
| V—C | 2.126(4) | C(9)—C(10) | 1.385(7) |
| N(1)—C(2) | 1.353(5) | C(10)—C(11) | 1.396(6) |
| N(1)—C(12) | 1.448(5) | C(11)—C(12) | 1.378(6) |
| N(2)—C(4) | 1.335(5) | C(13)—C(18) | 1.388(6) |
| N(2)—C(18) | 1.433(5) | C(13)—C(14) | 1.409(6) |
| C(2)—C(3) | 1.405(5) | C(14)—C(15) | 1.377(7) |
| C(2)—C(5) | 1.523(5) | C(15)—C(16) | 1.382(7) |
| C(3)—C(4) | 1.416(5) | C(16)—C(17) | 1.388(6) |
| C(4)—C(6) | 1.531(5) | C(17)—C(18) | 1.383(6) |

| Bond Angle | Angle (deg.) | Bond Angle | Angle (deg.) |
|---|---|---|---|
| N(1)—V—N(2) | 92.11(13) | C(3)—C(4)—C(6) | 117.6(3) |
| N(1)—V—C(1) | 111.1(2) | C(8)—C(7)—C(12) | 120.0(4) |
| N(2)—V—C(1) | 115.1(2) | C(9)—C(8)—C(7) | 120.4(4) |
| N(1)—V—C | 114.72(14) | C(10)—C(9)—C(8) | 119.4(4) |
| N(2)—V—C | 108.4(2) | C(9)—C(10)—C(11) | 120.5(4) |
| C(1)—V—C | 113.6(2) | C(12)—C(11)—C(10) | 120.9(4) |
| C(2)—N(1)—C(12) | 120.4(3) | C(11)—C(12)—C(7) | 118.6(4) |
| C(2)—N(1)—V | 127.6(3) | C(11)—C(12)—N(1) | 123.5(4) |
| C(12)—N(1)—V | 111.8(2) | C(7)—C(12)—N(1) | 117.6(3) |
| C(4)—N(2)—C(18) | 119.2(3) | C(18)—C(13)—C(14) | 119.6(4) |
| C(4)—N(2)—V | 127.2(3) | C(15)—C(14)—C(13) | 119.7(4) |
| C(18)—N(2)—V | 113.5(2) | C(14)—C(15)—C(16) | 120.3(4) |
| N(1)—C(2)—C(3) | 122.0(3) | C(15)—C(16)—C(17) | 120.4(5) |
| N(1)—C(2)—C(5) | 120.9(3) | C(18)—C(17)—C(16) | 119.9(4) |
| C(3)—C(2)—C(5) | 117.1(3) | C(17)—C(18)—C(13) | 120.1(4) |
| C(2)—C(3)—C(4) | 127.8(4) | C(17)—C(18)—N(2) | 120.2(4) |
| N(2)—C(4)—C(3) | 122.9(3) | C(13)—C(18)—N(2) | 119.5(4) |
| N(2)—C(4)—C(6) | 119.4(3) | | |

TABLE 3A.3

Structure Determination Summary for (Ph)$_2$nacnacVMe$_2$

Crystal Data

| | |
|---|---|
| Formula | C$_{19}$H$_{23}$N$_2$V |
| Formula weight | 330.13 |
| Crystal color | brown block |
| Crystal Size (mm) | 0.40 × 0.20 × 0.10 |
| Crystal System | monoclinic |
| Space Group | P2$_1$/n |
| Unit Cell Dimensions | a = 8.6616(2) Å |
| | b = 15.9937(4) Å |
| | c = 13.2812(1) Å |
| | α = 90° |
| | β = 93.317(2)° |
| | γ = 90° |
| Volume | 1836.78(8) Å$^3$ |
| Z | 4 |
| Density (calc.) | 1.220 g/cm$^3$ |
| Absorption Coefficient | 6.05 cm$^{-1}$ |
| F(000) | 712 |

Data Collection

| | |
|---|---|
| Diffractometer | Siemens P4 |
| Radiation | MoKα (l = 0.71073 Å) |
| Temperature | 295(2) K |
| Monochromator | Highly oriented graphite crystal |
| 2θ Range (w) | 3.98 to 56.30° |
| Scan type | Omega, Phi |
| Scan Range | 0.3° |
| Index Ranges | −11 < h < 10 |
| | 18 < k < 21 |
| | −17 < l < 16 |
| Reflections Collected | 7272 |
| Independent Reflections | 3894 (R$_{int}$ = 4.00%) |
| Observed Reflections | |

Solution and Refinement

| | |
|---|---|
| System Used | Siemens SHELXTL (5.03) |
| Solution | Direct Methods |
| Refinement Method | Full-Matrix Least-Squares |
| Quantity minimized | $S[w(F_o^2 - F_c^2)^2]/S[(wF_o^2)^2]^{1/2}$ |
| Hydrogen Atoms | Idealized contributions |
| Weighting Scheme | $w^{-1} = s^2(F) + 0.0010F^2$ |
| Final R Indices (obs. data) | R = 6.01%, wR = 15.52% |
| R Indices (all data) | R = 10.22%, wR = 19.76% |
| Goodness-of-Fit | 1.167 |
| Data-to-Parameter Ratio | 19.37:1 |
| Largest Difference Peak | 0.488 |
| Largest Difference Hole | −0.492 |

Example 3B
Preparation of 2,4-pentane di(N-phenyl)iminato bis-trimethyl Silylmethyl Vanadium, $(Ph)_2nacnacV(CH_2Si(CH_3)_3)_2$:

1.94 mmoles (1.00 g) of $(Ph)_2nacnacVCl_2(THF)_2$, reference Example 1B, was dissolved in 150 ml of THF and the solution was cooled to −30° C. 3.88 moles (0.366 g) of $LiCH_2Si(CH_3)_3$ crystals were slowly added to the THF solution which caused a color change from dark green to dark red brown. After stirring at room temperature for 4 hours, the reaction mixture was evaporated to dryness. By trituration in pentane, the residual THF was removed. A dark brown solid was extracted with pentane and filtered to remove LiCl. After the solvent was removed from the filtrate, the resulting brown oil was dissolved in HMDS and cooled to −30° C. No solid was isolated. However, 0.11 g (65% yield) of a dark brown oil, i.e., $(Ph)_2nacnacV(CH_2Si(CH_3)_3)_2$, was isolated by evaporation of the solvent. The oil was analyzed and the results are shown in Table 3B.

Example 5A
Preparation of 2,4-pentane di(N-phenyl)iminato Methyl Diethylether Tetrahydrofuran Vanadium Tetrakis-(3,5-bis-trifluoromethyl-phenyl)borate, $[(Ph)_2nacnacVMe(Et_2O)(THF)][B(C_6H_3(CF_3)_2)_4]$:

0.30 mmoles (100 mg) $(Ph)_2nacnacVMe_2$, reference Example 3A, was dissolved in 20 ml of diethylether and cooled to −30° C. In a separate flask, .30 mmoles (310 mg) of $H(Et_2O)_2[B(C_6H_3(CF_3)_2)_4]$ was dissolved in 10 ml of diethylether and cooled to −30° C. The diethylether solution of $H(Et_2O)_2[B(C_6H_3(CF_3)_2)_4]$ was slowly added by pipette to the cold solution of $(Ph)_2nacnacVMe_2$. With gas evolution, the color of the solution turned to slightly darker brown. 0.21 mmoles (278 mg, 69% yield) of orange $[(Ph)_2nacnacVMe(Et_2O)(THF)][B(C_6H_3(CF_3)_2)_4]$ crystals were isolated from a concentrated diethylether solution containing a several drops of THF that was cooled to −30° C.

Figure 5:
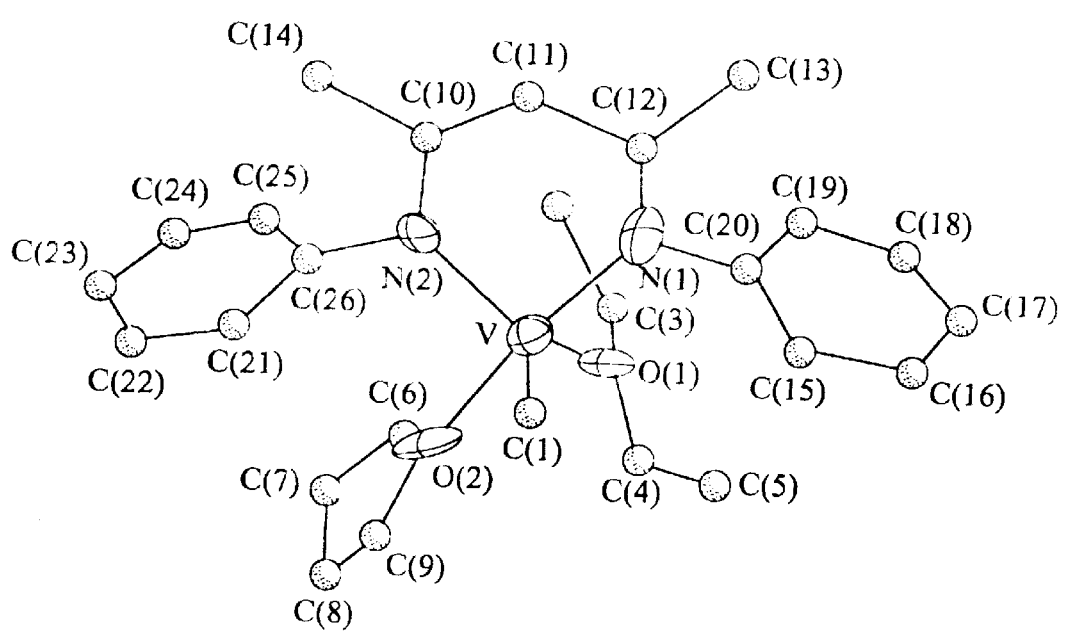
FIG. 5 depicts the crystal structure of the (Ph)$_2$nacnacVMe(Et$_2$O)(THF)[B(C$_6$H$_3$(CF$_3$)$_2$)$_4$], prepared in Example 5A (BArF anion not depicted).

The resulting compounds were analytically tested and the results are shown in Tables 5A.1–3. The single crystal X-ray diffraction results are shown in FIG. 5.

TABLE 3B

ANALYTICAL DATA FOR
$(Ph)_2nacnacV(CH_2Si(CH_3)_3)_2$

| $^1H\ NMR(C_6D_6)^a$: | 8.56 | −0.92 | −3.69 | *** | *** | *** | *** |
|---|---|---|---|---|---|---|---|
| δ (ppm) | (6H) | (18H) | (2H) | | | | |
| IR-neat$^b$: (cm$^{-1}$): | 3061 w | 3031 w | 2948 s | 2889 m | 2862 w | 2816 w | 1592 m |
| | 1528 s | 1510 s | 1483 vs | 1447 s | 1429 m | 1362 vs | 1262 m | 1241 s |
| | 1184 w | 1069 w | 1025 m | 935 w | 884 vs | 845 vs | 750 s | 700 vs |
| Mass Spectrometry: | 474.32(4.1) [M$^+$] | | 386.22(58.47) | | | 300(24.56) | | |
| m/z (%) | | | [M$^+$-SiMe$_4$] | | | [M$^+$-2 CH$_2$Si(CH$_3$)$_3$] | | |

Example 4
Preparation of 2,4-pentane di(N-phenyl)iminato (OTf)$_2$ bis-tetrahydrofuran Vanadium, $(Ph)_2nacnacV(OTf)_2(THF)_2$ 0.52 mmoles (270 mg,)$(Ph)_2nacnacVCl_2(THF)_2$, reference Example 1B, were dissolved in 40 ml of THF. 1.04 mmoles (280 mg) of AgOTf was added as a solid to the THF solution. After stirring overnight, the solution was filtered to remove AgCl. The dark green solution was concentrated and cooled to −30° C. for crystallization. 340 mg (87% yield) of dark green $(Ph)_2nacnacV(OTf)_2(THF)_2$ crystals were isolated. The crystals were analyzed and the results are shown in Table 4.

TABLE 4

ANALYTICAL DATA FOR
$(Ph)_2nacnacV(OTf)_2(THF)_2$

| $^1H\ NMR\ (THF\text{-}d_8)^a$: | 126.94 | 15.91 | 3.28 | *** | *** | *** | *** |
|---|---|---|---|---|---|---|---|
| δ (ppm) | (6h, vb) | (4H, vb) | (4H) | | | | |
| IR-KBr$^b$: (cm$^{-1}$) | 3061 w | 3031 w | 2985 w | 2933 w | 2907 w | 1592 w | 1540 m |
| | 1487 s | 1447 w | 1434 w | 1339 vs | 1236 vs | 1201 vs | 1014 s |
| | 928 w | 850 m | 844 s | 764 w | 710 m | 632 s | 524 w |
| Mass Spectrometry: | 597.98(6.4) [M$^+$-2 THF] | | | | 465.02(54.3) | | |
| m/z (%) | | | | | [M$^+$-SO$_2$CF$_3$, 2 THF] | | |
| UV-vis (THF)$^c$: | 598(1,318.4 | | 474(1,404.2 M$^{-1}$ cm$^{-1}$) | | 350(10,574.7 | | |
| λ$_{max}$(ε) | M$^{-1}$ cm$^{-1}$) | | | | M$^{-1}$ cm$^{-1}$) | | |
| μ$_{eff}$ | 3.2(std. dev. 1), μ$_B$ (294K) | | | | | | |
| Melting Pt. Range: | 160–163° C. | | | | | | |
| C$_{27}$H$_{33}$N$_2$O$_8$F$_6$S$_2$V | | | | | | | |
| Calculated: (%) | C 43.66 | H 4.48 | N 3.77 | | | | |
| Measured: (%) | C 42.53 | H 4.59 | N 3.87 | | | | |

TABLE 5A.1

ANALYTICAL DATA FOR
[(Ph)$_2$nacnacVMe(Et$_2$O)(THF)][B(C$_6$H$_3$(CF$_3$)$_2$)$_4$]

| $^1$H NMR(CD$_2$Cl$_2$)$^a$: δ (ppm) | 121.4 (6H, vb) | 90.5 (2H, vb) | 8.68 (4H, vb) | 7.73 (8H) | 7.57 (4H) | 0.90 (8H, b) | −2.46 (2H, vb) |
|---|---|---|---|---|---|---|---|
| IR-KBr$^b$: (cm$^{-1}$) | 3087 w | 2982 w | 2936 w | 2907 w | 1610 w | 1555 m | 1486 m |
| | 1450 w | 1429 w | 1356 vs | 1284 vs | 1158 vs, b | 1133 vs, b | 1020 m |
| | 938 s | 897 s | 795 w | 758 w | 710 s | 700 s | 679 s |
| | 670 s | 525 w | 496 w | | | | |
| UV-vis (Et$_2$O)$^c$: λ$_{max}$(ε) | 739(222 M$^{-1}$cm$^{-1}$) | | 609(334 M$^{-1}$cm$^{-1}$) | | 475(1350 M$^{-1}$cm$^{-1}$) | | |
| μ$_{eff}$ | 3.4(std. dev. 1), μ$_B$ (294K) | | | | | | |
| Melting Pt. Range: | 95–97° C. | | | | | | |
| C$_{58}$H$_{50}$N$_2$O$_2$F$_{24}$VB | | | | | | | |
| Calculated: (%) | C 53.02 | H 3.84 | N 2.13 | | | | |
| Measured: (%) | C 49.89 | H 3.28 | N 2.16 | | | | |

TABLE 5A.2

Interatomic Distances and Angles for the Cation of
[(Ph)$_2$nacnacVMe(Et$_2$O)(THF)][B(C$_6$H$_3$(CF$_3$)$_2$)$_4$]
(Note: the bond designations are with reference to FIG. 5 and the values noted in parentheses after the distances and angles represent the estimated standard deviation.)

| Bond | Distance (Å) | Bond | Distance (Å) |
|---|---|---|---|
| V—N(2) | 1.94(2) | C(8)—C(9) | 1.39(4) |
| V—N(1) | 2.00(2) | C(10)—C(11) | 1.38(3) |
| V—O(1) | 2.029(13) | C(10)—C(14) | 1.50(3) |
| V—C(1) | 2.09(2) | C(11)—C(12) | 1.53(3) |
| V—O(2) | 2.16(2) | C(12)—C(13) | 1.54(3) |
| O(1)—C(4) | 1.45(3) | C(15)—C(16) | 1.44(3) |
| O(1)—C(3) | 1.49(3) | C(15)—C(20) | 1.37(3) |
| O(2)—C(6) | 1.42(3) | C(16)—C(17) | 1.37(3) |
| O(2)—C(9) | 1.41(2) | C(17)—C(18) | 1.32(3) |
| N(1)—C(12) | 1.26(3) | C(18)—C(19) | 1.49(3) |
| N(1)—C(20) | 1.46(2) | C(19)—C(20) | 1.42(3) |
| N(2)—C(10) | 1.33(2) | C(21)—C(22) | 1.41(2) |
| N(2)—C(26) | 1.51(2) | C(21)—C(26) | 1.41(2) |
| C(2)—C(3) | 1.74(4) | C(22)—C(23) | 1.36(2) |
| C(4)—C(5) | 1.26(4) | C(23)—C(24) | 1.35(3) |
| C(6)—C(7) | 1.34(3) | C(24)—C(25) | 1.23(2) |
| C(7)—C(8) | 1.64(5) | C(25)—C(26) | 1.50(2) |

| Bond Angle | Angle (deg.) | Bond Angle | Angle (deg.) |
|---|---|---|---|
| N(2)—V—N(1) | 89.1(6) | C(6)—C(7)—C(8) | 97(2) |
| N(2)—V—O(1) | 134.4(6) | C(9)—C(8)—C(7) | 106(2) |
| N(1)—V—O(1) | 89.6(6) | C(8)—C(9)—O(2) | 110(2) |
| N(2)—V—C(1) | 95.7(10) | N(2)—C(10)—C(11) | 120(2) |
| N(1)—V—C(1) | 91.9(9) | N(2)—C(10)—C(14) | 119(2) |
| O(1)—V—C(1) | 129.0(10) | C(11)—C(10)—C(14) | 120(2) |
| N(2)—V—O(2) | 98.0(6) | C(10)—C(11)—C(12) | 129(2) |
| N(1)—V—O(2) | 171.0(6) | N(1)—C(12)—C(13) | 126(2) |
| O(1)—V—O(2) | 91.4(5) | N(1)—C(12)—C(11) | 116(2) |
| C(1)—V—O(2) | 92.9(9) | C(13)—C(12)—C(11) | 117(2) |
| C(4)—O(1)—C(3) | 109(2) | C(16)—C(15)—C(20) | 118(3) |
| C(4)—O(1)—V | 118.3(13) | C(17)—C(16)—C(15) | 123(2) |
| C(3)—O(1)—V | 131(2) | C(16)—C(17)—C(18) | 122(2) |
| C(6)—O(2)—C(9) | 105(2) | C(19)—C(18)—C(17) | 118(2) |
| C(6)—O(2)—V | 122.7(12) | C(18)—C(19)—C(20) | 119(2) |
| C(9)—O(2)—V | 132.3(13) | C(19)—C(20)—C(15) | 120(2) |
| C(12)—N(1)—C(20) | 111(2) | C(19)—C(20)—N(1) | 119(2) |
| C(12)—N(1)—V | 132(2) | C(15)—C(20)—N(1) | 121(2) |
| C(20)—N(1)—V | 116.4(12) | C(22)—C(21)—C(26) | 119(2) |
| C(10)—N(2)—C(26) | 112.5(14) | C(23)—C(22)—C(21) | 119(2) |
| C(10)—N(2)—V | 131.3(14) | C(22)—C(23)—C(24) | 119(2) |
| C(26)—N(2)—V | 116.0(11) | C(25)—C(24)—C(23) | 125(2) |
| O(1)—C(3)—C(2) | 106(2) | C(26)—C(25)—C(24) | 120(2) |
| C(5)—C(4)—O(1) | 128(3) | C(25)—C(26)—C(21) | 115(2) |
| C(7)—C(6)—O(2) | 117(2) | C(25)—C(26)—N(2) | 126.0(14) |
| | | C(21)—C(26)—N(2) | 119(2) |

TABLE 5A.3

Structure Determination Summary for
[(Ph)$_2$nacnacVMe(Et$_2$O)(THF)]B(C$_6$H$_3$(CF$_3$)$_2$)$_4$]

Crystal Data

| | |
|---|---|
| Formula | C$_{58}$H$_{50}$BF$_{24}$N$_2$O$_2$V |
| Formula Weight | 1324.75 |
| Crystal color | Orange-brown block |
| Crystal Size (mm) | 0.05 × 0.20 × 0.40 |
| Crystal System | monoclinic |
| Space Group | Cc |
| Unit Cell Dimensions | a = 20.1893(11) Å |
| | b = 15.6580(11) Å |
| | c = 20.1295(13) Å |
| | α = 90° |
| | β = 106.893(2)° |
| | γ = 90° |
| Volume | 6088.8(7) Å$^3$ |
| Z | 4 |
| Density (calc.) | 1.445 g/cm$^3$ |
| Absorption Coefficient | 2.79 cm$^{-1}$ |
| F(000) | 2688 |

Data collection

| | |
|---|---|
| Diffractometer | Siemens P4 |
| Radiation | MoKα (l = 0.71073 Å) |
| Temperature | 293(2) K |
| Monochromator | Highly oriented graphite crystal |
| 2θ Range (w) | 3.34 to 56.46° |
| Scan type | Omega, Phi |
| Scan Range | 0.3° |
| Index Ranges | −25 < h < 26 |
| | 0 < k < 20 |
| | −25 < l < 26 |
| Reflections Collected | 8943 |
| Independent Reflections | 17489 (R$_{int}$ = 10.94%) |
| Observed Reflections | 4631 |

TABLE 5A.3-continued

Structure Determination Summary for
[(Ph)$_2$nacnacVMe(Et$_2$O)(THF)][B(C$_6$H$_3$(CF$_3$)$_2$)$_4$]

| Solution and Refinement | |
|---|---|
| System Used | SHELXTL (5.03) |
| Solution | Direct Methods |
| Refinement Method | Full-Matrix Least-Squares |
| Quantity minimized | $S[w(F_o^2 - F_c^2)^2]/S[(wF_o^2)^2]^{a\ 1/2}$ |
| Hydrogen Atoms | Idealized contributions |
| Weighting Scheme | $w^{-1} = s^2(F) + 0.0010$ |
| Final R Indices (obs. data) | R = 14.8%, wR = 30.9% |
| R Indices (all data) | R = 24.9%, wR = 37.5% |
| Goodness-of-Fit | 1.800 |
| Data-to-Parameter Ratio | 11.1:1 |
| Largest Difference Peak | 2.565 |
| Largest Difference Hole | −0.531 |

Example 5B
Preparation of 2,4-pentane di(N-phenyl)iminato Methyl Bis-diethylether Vanadium Tetrakis-(3,5-bistrifluoromethylphenyl)borate, [(Ph)$_2$nacnacVMe(Et$_2$O)$_2$][B(C$_6$H$_3$(CF$_3$)$_2$)$_4$]:

Before the reaction, the drybox was flushed for 30 minutes in an attempt to remove all of the THF from the inert atmosphere. The same reaction sequence and the same reactant quantities as in Example 5A were followed for the synthesis of (Ph)$_2$nacnacVMe(Et$_2$O)$_2$[B(C$_6$H$_3$(CF$_3$)$_2$)$_4$]. Orange crystals of were isolated in moderate yield (195 mg, 46% yield) from a concentrated diethylether solution cooled to −30° C., and based on the analytical data shown in Table 5B the product is believed to contain [(Ph)$_2$nacnacVMe(Et$_2$O)$_2$][B(C$_6$H$_3$(CF$_3$)$_2$)$_4$].

Preparation 1: Reaction of 2-N-phenylamino-4-N'-phenylimino-3-pentenyl Dichloro Bis-tetrahydrofuran Chromium, (Ph)$_2$nacnacCrCl$_2$(THF)$_2$, with MeLi:

1.16 mmoles (600 mg) of (Ph)$_2$nacnacCrCl$_2$(THF)$_2$, reference Example 1C, was dissolved in THF and cooled to −30° C. 2 molar eq. of a MeLi solution was added dropwise to the (Ph)$_2$nacnacCrCl$_2$(THF)$_2$ solution. Upon addition of the MeLi solution, the suspension rapidly turned to brown. After the reaction mixture was allowed to stir at room temperature for 4 hours, the solution was evaporated to dryness. THF was removed by trituration in ether. The resulting solid was extracted with ether and filtered to remove LiCl. The black-green filtrate was then concentrated and cooled to −30° C. for crystallization. 210 mg (35% yield) of ((Ph)$_2$nacnac)$_2$Cr black green crystals of were isolated.

Figure 6:
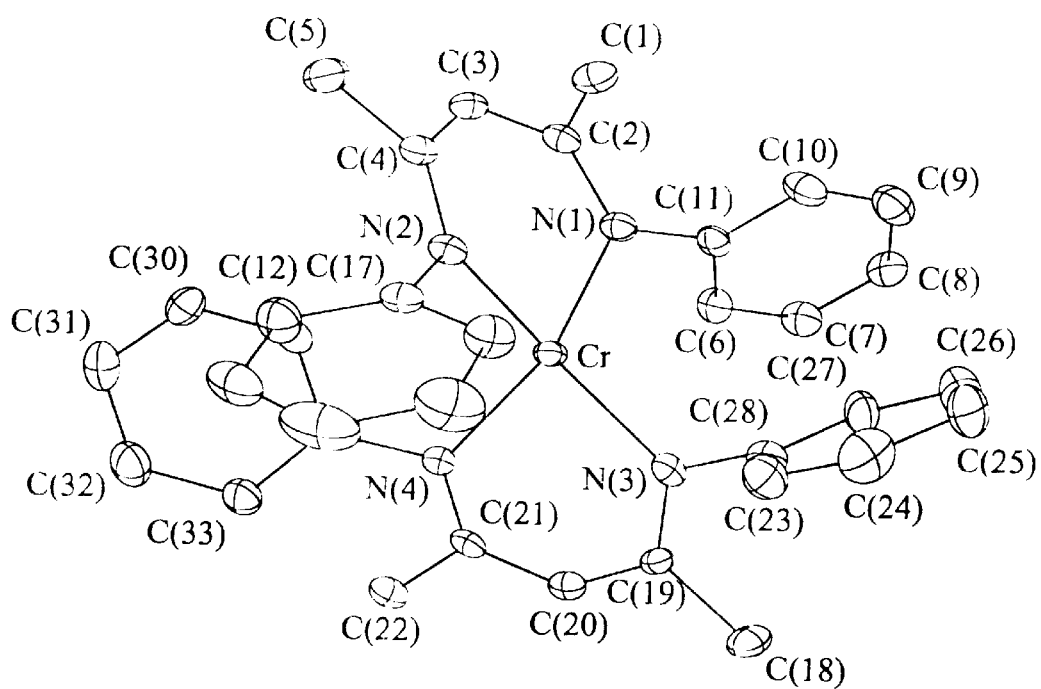
FIG. 6 depicts the crystal structure of the ((Ph)$_2$nacnac)$_2$Cr, prepared in Example 6.

The resulting compounds were analytically tested and the results are shown in Tables 6A.1–3. The single crystal X-ray diffraction results are shown in FIG. 6.

Preparation 2: Reaction of 2-N-Phenylamino-4-N'-Phenylimino-2-Pentene, (Ph)$_2$nacnacH, with MeLi and CrCl$_2$:

16 mmoles (4.0 g) of (Ph)$_2$nacnac(H) was dissolved in THF and cooled to −30° C. 16 mmoles (352 mg) MeLi was added to the THF solution of (Ph)$_2$nacnacH. Using an addition funnel, the THF–(Ph)$_2$nacnacLi solution was added dropwise, over a one hour period, to 8 mmoles (983 mg) of CrCl$_2$ in a THF solution. The reaction mixture was then allowed to stir at room temperature overnight. The solvent was removed to dryness and extracted with diethylether. The extract was then filtered to remove LiCl. 7.09 mmoles (3.7

TABLE 5B

ANALYTICAL DATA FOR
[(Ph)$_2$nacnacVMe(Et$_2$O)$_2$][B(C$_6$H$_3$(CF$_3$)$_2$)$_4$]

| $^1$H NMR(C$_6$D$_6$)$^a$: | 123.95 | 7.60 | 4.39 | −16.75 | *** | *** | *** |
|---|---|---|---|---|---|---|---|
| δ (ppm) | (6H, vb) | (4H) | (6H) | (1H, vb) | | | |
| IR-KBr$^b$: (cm$^{-1}$) | 3081 w | 2977 w | 2936 w | 2907 w | 2882 w | 1610 w | 1437 w |
| | 1355 vs | 1279 vs | 1126 m | 1027 w | 945 w | 887 m | 839 m |
| | 798 w | 771 w | 744 w | 713 m | 682 m | 448 w | *** |
| UV-vis (Et$_2$O)$^c$: | 776(266 | | | 629(421 | | 469(1400 | |
| λ$_{max}$(ε) | M$^{-1}$cm$^{-1}$) | | | M$^{-1}$cm$^{-1}$) | | M$^{-1}$cm$^{-1}$) | |
| $\mu_{eff}$ | 3.1(std. dev. 1), $\mu_B$ (294K) | | | | | | |
| Melting Pt. Range: | 89–93° C. | | | | | | |
| C$_{58}$H$_{52}$N$_2$O$_2$F$_{24}$VB | | | | | | | |
| Calculated: (%) | C 52.48 | H 3.95 | N 2.11 | | | | |
| Measured: (%) | C 49.41 | H 3.47 | N 2.11 | | | | |

Example 6A
Preparation of bis-(2,4-pentane di(N-phenyl)iminato) Chromium(II), ((Ph)$_2$nacnac)$_2$Cr:

g, 84% yield) of black ((Ph)$_2$nacnac)$_2$Cr crystals were isolated from a concentrated diethylether solution that was cooled to −30° C.

TABLE 6A.1

ANALYTICAL DATA FOR
((Ph)$_2$nacnac)$_2$Cr

| $^1$H NMR(C$_6$D$_6$)$^a$: | 123.95 | 7.60 | 4.39 | −16.75 | *** | *** | *** |
|---|---|---|---|---|---|---|---|
| δ (ppm) | (6H, vb) | (4H) | (6H) | (1H, vb) | | | |
| IR-KBr$^b$: (cm$^{-1}$) | 3055 w | 3029 w | 2922 w | 2879 m | 1591 w | 1540 s | 1515 m |
| | 1482 s | 1449 m | 1382 vs | 1276 w | 1264 w | 1021 m | 866 w |
| | 842 w | 752 w | 700 m | *** | *** | *** | *** |

TABLE 6A.1-continued

ANALYTICAL DATA FOR ((Ph)$_2$nacnac)$_2$Cr

| | | | |
|---|---|---|---|
| Mass Spectrometry: m/z (%) | 550.22(100) [M$^+$] | | 301.05(45.75) [M$^+$-C$_7$H$_{17}$N$_2$] |
| UV-vis (Et$_2$O)$^c$: | 348(shoulder) | | *** |
| $\lambda_{max}(\epsilon)$ | (10,444.5 M$^{-1}$cm$^{-1}$) | | |
| $\mu_{eff}$ | 5.1(std. dev. 1), $\mu_B$ (294K) | | |
| Melting Point: | 220° C. | | |
| C$_{34}$H$_{34}$N$_4$Cr | | | |
| Calculated: (%) | C 74.15 | H 6.23 | N 10.18 |
| Measured: (%) | C 72.42 | H 6.30 | N 10.01 |

TABLE 6A-2

Interatomic Distances and Angles for ((Ph)$_2$nacnac)$_2$Cr

| Bond | Distance (Å) | Bond | Distance (Å) |
|---|---|---|---|
| Cr-N(2) | 2.049(4) | C(12)-C(17) | 1.381(6) |
| Cr-N(3) | 2.055(4) | C(12)-C(13) | 1.406(7) |
| Cr-N(1) | 2.058(3) | C(13)-C(14) | 1.375(9) |
| Cr-N(4) | 2.069(3) | C(14)-C(15) | 1.353(9) |
| N(1)-C(2) | 1.336(5) | C(15)-C(16) | 1.392(7) |
| N(1)-C(11) | 1.451(5) | C(16)-C(17) | 1.380(6) |
| N(2)-C(4) | 1.314(5) | C(18)-C(19) | 1.522(6) |
| N(2)-C(17) | 1.432(5) | C(19)-C(20) | 1.389(6) |
| N(3)-C(19) | 1.323(5) | C(20)-C(21) | 1.381(6) |
| N(3)-C(28) | 1.431(5) | C(21)-C(22) | 1.505(6) |
| N(4)-C(21) | 1.339(5) | C(23)-C(24) | 1.378(7) |
| N(4)-C(34) | 1.424(5) | C(23)-C(28) | 1.385(6) |
| C(1)-C(2) | 1.515(6) | C(24)-C(25) | 1.372(9) |
| C(2)-C(3) | 1.401(6) | C(25)-C(26) | 1.359(8) |
| C(3)-C(4) | 1.406(6) | C(26)-C(27) | 1.376(7) |
| C(4)-C(5) | 1.513(6) | C(27)-C(28) | 1.393(6) |
| C(6)-C(7) | 1.377(6) | C(29)-C(30) | 1.377(6) |
| C(6)-C(11) | 1.379(6) | C(29)-C(34) | 1.398(6) |
| C(7)-C(8) | 1.379(8) | C(30)-C(31) | 1.388(7) |
| C(8)-C(9) | 1.363(7) | C(31)-C(32) | 1.387(7) |
| C(9)-C(10) | 1.378(7) | C(32)-C(33) | 1.383(7) |
| C(10)-C(11) | 1.380(6) | C(33)-C(34) | 1.398(6) |

| Bond Angle | Angle (deg.) | Bond Angle | Angle (deg.) |
|---|---|---|---|
| N(2)-Cr-N(3) | 149.78(14) | C(10)-C(11)-N(1) | 121.3(4) |
| N(2)-Cr-N(1) | 88.47(14) | C(17)-C(12)-C(13) | 120.0(5) |
| N(3)-Cr-N(1) | 105.49(4) | C(14)-C(13)-C(12) | 119.8(5) |
| N(2)-Cr-N(4) | 100.69(14) | C(15)-C(14)-C(13) | 119.7(5) |
| N(3)-Cr-N(4) | 89.35(14) | C(14)-C(15)-C(16) | 121.4(6) |
| N(1)-Cr-N(4) | 132.88(14) | C(17)-C(16)-C(15) | 119.7(5) |
| C(2)-N(1)-C(11) | 117.3(3) | C(12)-C(17)-C(16) | 119.3(4) |
| C(2)-N(1)-Cr | 121.6(3) | C(12)-C(17)-N(2) | 123.3(4) |
| C(11)-N(1)-Cr | 119.2(3) | C(16)-C(17)-N(2) | 117.2(4) |
| C(4)-N(2)-C(17) | 122.9(4) | N(3)-C(19)-C(20) | 123.6(4) |
| C(4)-N(2)-Cr | 126.2(3) | N(3)-C(19)-C(18) | 119.3(4) |
| C(17)-N(2)-Cr | 110.9(3) | C(20)-C(19)-C(18) | 117.2(4) |
| C(19)-N(3)-C(28) | 119.9(4) | C(21)-C(20)-C(19) | 128.7(4) |
| C(19)-N(3)-Cr | 125.5(3) | N(4)-C(21)-C(20) | 123.8(4) |
| C(28)-N(3)-Cr | 114.1(3) | N(4)-C(21)-C(22) | 120.1(4) |
| C(21)-N(4)-C(34) | 118.9(4) | C(20)-C(21)-C(22) | 116.0(4) |
| C(21)-N(4)-Cr | 123.1(3) | C(24)-C(23)-C(28) | 120.0(5) |
| C(34)-N(4)-Cr | 117.0(3) | C(25)-C(24)-C(23) | 120.7(5) |
| N(1)-C(2)-C(3) | 123.8(4) | C(26)-C(25)-C(24) | 119.2(5) |
| N(1)-C(2)-C(1) | 119.7(4) | C(25)-C(26)-C(27) | 121.7(6) |
| C(3)-C(2)-C(1) | 116.5(4) | C(26)-C(27)-C(28) | 119.3(5) |
| C(2)-C(3)-C(4) | 128.0(4) | C(23)-C(28)-C(27) | 119.1(4) |
| N(2)-C(4)-C(3) | 121.9(4) | C(23)-C(28)-N(3) | 118.8(4) |
| N(2)-C(4)-C(5) | 121.5(4) | C(27)-C(28)-N(3) | 122.1(4) |
| C(3)-C(4)-C(5) | 116.6(4) | C(30)-C(29)-C(34) | 121.2(4) |
| C(7)-C(6)-C(11) | 121.1(5) | C(29)-C(30)-C(31) | 120.3(4) |
| C(6)-C(7)-C(8) | 119.6(5) | C(30)-C(31)-C(32) | 119.5(5) |
| C(9)-C(8)-C(7) | 119.7(5) | C(33)-C(32)-C(31) | 119.8(5) |
| C(8)-C(9)-C(10) | 120.8(5) | C(32)-C(33)-C(34) | 121.5(4) |
| C(9)-C(10)-C(11) | 120.2(5) | C(33)-C(34)-C(29) | 117.6(4) |
| C(6)-C(11)-C(10) | 118.6(4) | C(33)-C(34)-N(4) | 122.2(4) |
| C(6)-C(11)-N(1) | 120.0(4) | C(29)-C(34)-N(4) | 120.1(4) |

(Note: the bond designations are with reference to FIG. 6 and the values noted in parentheses after the distances and angles represent the estimated standard deviation.)

TABLE 6A-3

Structure Determination Summary for ((Ph)$_2$nacnac)$_2$Cr

| | |
|---|---|
| Crystal Data | |
| Empirical Formula | C$_{34}$H$_{34}$N$_4$Cr |
| Formula Weight | 550.65 |
| Crystal color | Dark green plates |
| Crystal Size (mm) | 0.40 × 0.40 × 0.06 |
| Crystal System | triclinic |
| Space Group | P1 |
| Unit Cell Dimensions | a = 10.54650(10)Å |
| | b = 11.4442(2)Å |
| | c = 13.8021(2)Å |
| | α = 87.5203(9)° |
| | β = 72.7442(8)° |
| | γ = 65.33° |
| Volume | 1439.44(5)Å$^3$ |
| Z | 2 |
| Density (calc.) | 1.270 g/cm$^3$ |
| Absorption Coefficient | 4.27 cm$^{-1}$ |
| F(000) | 580 |
| Data collection | |
| Diffractometer Used | Siemens P4 |
| Radiation | MoKα (1 = 0.71073Å) |
| Temperature | 218(2)K |
| Monochromator | Highly oriented graphite crystal |
| 2θ Range(w) | 3.10 to 56.60° |
| Scan type | Omega, Phi |
| Scan Range | 0.30 |
| Index Ranges | −13 < h < 13 |
| | −14 < k < 14 |
| | 0 < l < 18 |
| Reflections Collected | 6231 |
| Independent Reflections | 6231 (R$_{int}$ = 0.0000%) |
| Observed Reflections | 4039 |
| Solution and Refinement | |
| System Used | SHELXTL (5.03) |
| Solution | Direct Methods |
| Refinement Method | Full-Matrix Least-Squares |
| Quantity minimized | $S[w(F_o^2 - F_c^2)^2]/S[(wF_o^2)^2]^{1/2}$ |
| Hydrogen Atoms | Idealized contributions |
| Weighting Scheme | $w^{-1} = s^2(F) + 0.0010$ |
| Final R Indices (obs. data) | R = 8.87%, wR = 21.76% |

TABLE 6A-3-continued

Structure Determination Summary for((Ph)$_2$nacnac)$_2$Cr

| | |
|---|---|
| R Indices (all data) | R = 11.77%, wR = 24.49% |
| Goodness-of-Fit | 1.100 |
| Data-to-Parameter Ratio | 17.7:1 |
| Largest Difference Peak | 0.892 |
| Largest Difference Hole | −0.812 |

Example 6B
Preparation of Bis-(2,4-pentane di(N-phenyl)iminato Monochloro) Chromnium, [(Ph)$_2$nacnac]$_2$CrCl:

1.45 mmoles (800 mg) of [(Ph)$_2$nacnac]$_2$Cr, as in preparation 2 of Example 6A, was dissolved in 100 ml of diethyl ether. Addition of tetrachloroethane (0.076 ml, 0.726 mmol) to the diethyl ether solution with stirring caused no immediate color change. After stirring overnight a brown-red solution was obtained. Evaporation of solvent to remove excess tetrachloroethane yielded a dark brown solid which was extracted by diethyl ether. Brown needle crystals (620 mg, 72.9% yield) were isolated by slow evaporation of solvent at room temperature.

TABLE 6B.1

ANALYTICAL DATA FOR ((Ph)$_2$nacnac)$_2$CrCl

| $^1$H NMR(C$_6$D$_6$)$^a$: δ (ppm) | 38.49 (12H, vb) | 7.1 (20H, b) | *** | *** | *** | *** | *** |
|---|---|---|---|---|---|---|---|
| IR-KBr$^b$: (cm$^{-1}$) | 3054 s | 3017 m | 2962 w | 2920 m | 1592 m | 1528 s | 1497 s |
| | 1410 s | 1388 s | 1254 m | 1185 m | 1070 w | 1024 m | 940 w |
| | 916 w | 841 w | 754 m | 705 s | 518 w | *** | *** |
| Mass Spectrometry: m/z (%) | | 585.13(78.29) [M$^+$] | | | | 550.1522(100) [M$^+$-Cl] | |
| UV-vis (Et$_2$O)$^c$: λ$_{max(ε)}$ | 656.0 (316.46 M$^{-1}$cm$^{-1}$) | | 663.0 (303.51 M$^{-1}$cm$^{-1}$) | | | 766 (177.5 M$^{-1}$cm$^{-}$) | |
| $μ_{eff}$ | | | 4.69(std. Dev. 1), $μ_B$ (294K) | | | | |
| Melting Point: | | | | | | | |
| C$_{34}$H$_{34}$N$_4$ClCr | | | | | | | |
| Calculated: (%) | C 69.7 | H 9.8 | N 9.56 | | | | |
| Measured: (%) | C 68.54 | H 5.72 | N 9.32 | | | | |

Polymerization Experiments
Method For Determining M$_w$, M$_n$, M$_z$, & M$_p$

The M$_w$, weight average molecular weight, M$_n$, number average molecular weight, weighted to the low end of the material, M$_z$, average weighted to the high end of the material, and M$_p$, the peak position molecular weight for the polymer samples are determined using Size Exclusion Chromatography (SEC) columns. SEC columns separate a polymer solution into fractions based on their 3-dimensional molecular size (hydrodynamic volume—Hv). These fractions are detected by a refractive index (RI) detector which responds linearly to the concentration of homogenous polymers. The molecular weight distribution (MWD) is then determined as the linear equivalent molecular weight relative to a linear calibration polyethylene (PE) standard (Chevron 9640). For high density PE (HDPE), the molecular weights determined can be considered an absolute quantity. For low density PE (LDPE), the average molecular weight (M$_w$) is underestimated proportionately to the additional weight of branches along the backbone. For samples containing a fairly consistent amount of branching, molecular weight distributions can be compared on a relative scale to each other.

Samples of the polymer are ground up to a 20 mesh size. 8 mg +/−0.2 mg are weighed into a 4 ml vial with three separate preparations per measurement. 4 mL of TCB (with 500 ppm antioxidant to prevent molecular decomposition) is added with an automatic solvent dispenser to each vial. Samples are dissolved in an oven for 4 Hours at 180° C. The vials are shaken 3 times over this 4 hour period. The samples are then tested using a Waters 150C Chromatography System equipped with 3 Mixed A+1 50A Polymer Laboratories (UK) Columns. The measurements are conducted under the following conditions:

Concentration: 2 mg/mL
Injection Volume: 400 uL
Flowrate: 1 mL/min
Column and Injector Compartment Temperature: 150C
Run Time: 1 Hour The Method of Calculation is: Weight fraction of polymer is weighted against molecular weight with Flow Rate Correction employed by referencing flow rate marker peak. The ViscoTek:TriSec Software Conventional Calibration Module ver. 3.00 is used to report M$_n$, M$_w$, M$_z$, M$_p$, and D average for the three separate preparations.

Method For Determining Short Chain Branching (SCB)

Samples were analyzed on a Varian Unity+ NMR spectrometer at a magnetic field of 7 Tesla with a 10 mm broadband probe tuned for C-13. Approximately 0.5 g of sample was placed in a 10 mm NMR tube and filled with 3 ml of a 3:1 1,2,4-trichlorobenzene/deuterated benzene mixture. The sample is warmed to 130° C. and allowed to dissolve until a clear solution is formed. When bubbles and voids in the viscous solution have been eliminated, the sample is ready for analysis. The sample is placed in the bore of the NMR magnet and heated to 130° C. The sample is allowed to come to thermal equilibrium and stabilize for 5 minutes. The sample is deuterium locked on to the deuterated benzene signal for magnet field stability and the sample's magnetic field is shimmed to reduce magnetic field inhomogeneities in order to increase resolution and the signal to noise ratio. The sample is pulsed every 5.9 seconds (0.9s acquisition time and 5s recycle delay for relaxation) for 2500 total transients making a total experiment time of 4 hours. The recorded free induction decay is Fourier transformed to yield the NMR spectrum. The spectrum is then phased and baseline corrected. The short chain branching content is determined using specific resonances that are characteristic and unique to each type of short chain branch (methyl through hexyl and longer). The ratio of the integrals of each characteristic resonance with the resonance for the polymer backbone (27.8 to 31.5 ppm) is taken and the ratio is reported as short chain branches per 1000 carbons. Low molecular weight carbon content is determined by the ratio of the integral of the characteristic resonance at 114 ppm to the integral of the polymer backbone.

Method For Determining Melting Point (Peak DSC M.P.)

Samples were analyzed on a Perkin-Elmer DSC7 differential scanning calorimeter with an intercooler attachment. The sample size of approximately 10 mg was placed in an aluminum pan and an aluminum lid was crimped on. The sample is heated twice, the first time to eliminate thermal history and the second time where the DSC sample measurement is recorded. The sample is heated from 0° C. the first time to 170° C. at 20° C./min, held for 5 minutes at 170° C., then control cooled at 10° C./min to 0° C. The sample is held at 0° C. for 1 minute then reheated at 20° C./min to 170° C. This second heating scan is recorded. The peaks are used to determine the melting points which generally appear between 90 to 140° C. The area under the curve is considered to be the heat of fusion of the polyethylene copolymer.

The following polymerization that resulted in formation of oligomers were characterized using an HP 5890 Gas Chromatograph fitted with a FID Detector, Helium Carrier Chrompack Column: WCOT ulti-metal 10M XO.53MM coating HT SIMDIST CBDF=0.15 UM. At the following conditions: 120° C.×1 min×10° C./min×150° C.×0 min and RampA: 6.0° C./min×350° C.×0 min.

Example 7
Polymerization of Ethylene in a NMR Tube Reaction in the Presence Of in-situ $(Ph)_2nacnacVMe_2[B(C_6F_5)_3]$:

Preparation 1 (in $CD_2Cl_2$):

0.0453 mmoles (15 mg) of $(Ph)_2nacnacVMe_2$, reference Example 3A, and 0.0453 mmoles (23 mg) of $B(C_6F_5)_3$ were transferred to an NMR tube reactor and $CD_2Cl_2$ was vacuum transferred. Ethylene (@1 atm.) was charged to the NMR tube and it was closed with a Teflon tap. After 5 minutes, a $^1H$ NMR spectrum was recorded. Only the ethylene resonance ($\delta$ 5.40 ppm) and a new peak $\delta$ 1.7 ppm was added to the original spectrum, reported in example 3A above. After 10 minutes, white particles of polyethylene had precipitated out of the solution. One more charge of ethylene (@1 atm) was added to the NMR tube and allowed to react for three hours. Another $^1H$ NMR reading was taken and the spectrum had all the resonances associated with the catalyst while the ethylene monomer peak had nearly disappeared.

Preparation 2 (in $C_6D6$):

Polymerization of ethylene was also tried in an NMR tube with $4.53\times10^{-5}$ moles (15 mg) of, reference Example 3A, and $4.53\times10^{-5}$ moles (23 mg) of $B(C_6F_5)_3$. Upon condensing $C_6D_6$, $(Ph)_2nacnacVMe_2$ and $B(C_6F_5)_3$ reacted to give a brown black oil which was not soluble in $C_6D_6$. After one day at room temperature, the ethylene monomer peak had decreased to approx. 40% (integrated to C6D6 peak) $^1H$ NMR ($C_6D_6$): broad peaks from 2.4 to 0.6 ppm.

Example 8
Polymerization Of Ethylene in a Parr Reactor in the Presence of $(Ph)_2nacnacVMe_2$ and Cocatalyst in $CH_2Cl_2$:

0.151 mmoles (50 mg) of $(Ph)_2nacnacVMe_2$, reference Example 3a, and 0.151 mmoles of $B(C_6F_5)_3$ (77 mg) were dissolved in 100 ml of $CH_2Cl_2$ and the solution was placed in a Parr reactor. Ethylene (@700 psig) was charged to the reactor. After about five minutes, the ethylene supply was closed because the temperature of the reactor had reached 120° C. The pressure decreased steadily with stirring. After stirring for several hours, the reactor was opened to atmosphere. Dark colored polymer was found in blocks. The blocks were washed with a methanol/HCl mixture and deionized (DI) water and then dried in a vacuum oven at 60° C. overnight. 5.2 grams of polymer were collected. Polymer analysis: $M_w$=547,700; $M_w/M_n$=2.06; Peak DSC M.P.: 134.2° C.

Example 9
Polymerization Of Propylene in a NMR Tube Reactor in the Presence of $(Ph)_2nacnacVMe_2$ and Cocatalyst in $CD_2Cl_2$:

$4.53\times10-5$ moles(15 mg) of $(Ph)_2nacnacVMe_2$, reference Example 3a, and $4.53\times10^{-5}$ moles (23 mg) of $B(C_6F_5)_3$ were dissolved in $CD_2Cl_2$ and placed in a NMR tube reactor. Propylene (@1 atm.) was then charged to the NMR tube reactor. When a $^1H$ NMR spectrum was recorded after 10 minutes, there was no indication of reaction. $^1H$ NMR spectra obtained after several hours at room temperature and after heating to 60° C. overnight, continued to show no reaction.

Example 10
Polymerization of 1-Hexene in a NMR Tube Reactor in the Presence of $(Ph)_2nacnacVMe_2$ and Cocatalyst in $CD_2Cl_2$:

$(Ph)_2nacnacVMe_2[B(C_6F_5)_3]$ was prepared as described above, reference Example 9. 1-hexene (pre-dried over Na/K alloy) was vacuum transferred to a NMR tube reactor. A $^1H$ NMR spectrum was recorded after 10 minutes and then the NMR tube was heated to 60° C. overnight. Analysis of the resulting product indicated formation of oligomers, mostly dimers to hexamers, including branched oligomers.

Example 11
Copolymerization of Ethylene and 1-Hexene in a Parr Reactor in the Presence of $(Ph)_2nacnacVMe_2$ and Cocatalyst in $CH_2Cl_2$:

0.151 mmoles (50 mg) of $(Ph)_2nacnacVMe_2$, reference Example 3a, and 0.151 mmoles of $B(C_6F_5)_3$ (77 mg) were dissolved in a solvent mixture of 60 ml of $CH_2Cl_2$ and 30 ml of 1-hexene. The solution was placed in a Parr reactor. Ethylene (@800 psig) was charged to the reactor. Then the ethylene supply was closed because the temperature of the reactor reached nearly 120° C. With stirring, the pressure decreased steadily. After stirring for several hours, the reactor was opened and blocks of polymer were observed. The blocks were washed with a methanol/HCl mixture and deionized (DI) water and then dried in a vacuum oven at 60° C. overnight. 5.2 grams of polymer were collected. Polymer analysis: $M_w$=1,136,000; $M_w/M_n$=2.42; Peak DSC M.P: 131.4° C.;. $^{13}C$ NMR: no side chains were indicated.

Example 12
Polymerization of Ethylene in a NMR Tube Reactor in the Presence of $[(Ph)_2nacnacVMe(Et_2O)(THF)][B(C_6H_3(CF_3)_2)_4]$ in $CD_2Cl_2$:

$1.88\times10^{-5}$ moles (25 mg) $[(Ph)_2nacnacVMe(Et_2O)(THF)][B(C_6H_3(CF_3)_2)_4]$, reference Example 5A, in $CD_2Cl_2$ was introduced into a NMR tube reactor. Ethylene (@1 atm.) was charged into the NMR tube and the Teflon tab was closed. After 15 minutes, a fine precipitate of polyethylene was visible and a $^1H$ NMR spectrum recorded trace amounts of free diethylether peaks along with an intense ethylene monomer peak at $\delta$ 5.40 ppm. After allowing the reaction to stand overnight at room temperature, several particles of polymer were visually observed and $^1H$ NMR spectrum recorded free diethylether resonances and trace amounts of unreacted ethylene monomer. This reaction was run an additional two times substituting propylene (@1 atm.) and 1-hexene for ethylene and no polymerization was observed even with heating.

Example 13
Polymerization of Ethylene in a Parr Reactor in the Presence of [(Ph)$_2$nacnacVMe(Et$_2$O)(THF)][B(C$_6$H$_3$(CF$_3$)$_2$)$_4$] in CH$_2$Cl$_2$:

0.045 mmoles (60 mg) [(Ph)$_2$nacnacVMe(Et$_2$O)(THF)][B(C$_6$H$_3$(CF$_3$)$_2$)$_4$], reference Example 5A, dissolved in 100 ml of CH$_2$Cl$_2$ was introduced into a Parr reactor. Ethylene (@700 psig) was supplied to the reactor. Once the reactor was pressurized, the ethylene supply was shutoff. With stirring, the ethylene pressure decreased slowly. After stirring for several hours, the reactor was opened to atmosphere. After stirring for several hours, the reactor was opened and blocks of polymer were observed. The blocks were washed with a methanol/HCl mixture and deionized (DI) water and then dried in a vacuum oven at 60° C. overnight. 2.5 g of polymer were collected. Polymer analysis: M$_w$=450,600; M$_w$/M$_n$=1.96; and Peak DSC M.P: 135.9° C.

Example 14
Polymerization of Ethylene in a Parr Reactor in the Presence of (Ph)$_2$nacnacVCl$_2$(THF)$_2$ and Cocatalyst in CH$_2$Cl$_2$:

0.776 mmoles (40 mg) of (Ph)$_2$nacnacVCl$_2$(THF)$_2$, reference Example 1B, was dissolved in I0 ml, of dry CH$_2$Cl$_2$ in a Parr reactor. The color of the solution turned brown. Upon addition of 7.3 g (approx. 100 molar eq.) of MAO, 10 wt. % solution in toluene, the color of the solution instantaneously changed to dark red brown. Ethylene (@400 psig) was supplied to the reactor. Once the reactor was pressurized, the ethylene supply was shutoff. Pressure decreased slowly with stirring. After stirring for several hours, the reactor was opened and blocks of polymer were observed. The blocks were washed with a methanol/HCl mixture and deionized (DI) water and then dried in a vacuum oven at 60° C. overnight. 4.6 g of polymer were collected. Polymer analysis: M$_w$=350,032, M$_w$/M$_n$=10.84.

Example 15
Polymerization of Ethylene in a Parr Reactor in the Presence of (Ph)$_2$nacnacVCl$_2$(THF)$_2$ and Cocatalyst in Toluene:

1.20×10$^{-5}$ moles (8 mg) of (Ph)$_2$nacnacVCl$_2$(THF)$_2$, reference Example 1B, was dissolved in 50 ml of toluene in a Parr reactor and 1.2 g (approx. 100 molar eq.) of MAO, 10 wt. % solution in toluene, was added to the solution. Polymerization was performed under a constant pressure of ethylene (@300 psig) for 1 hour, after which the ethylene supply was closed. The reaction was allowed to continue for an additional ½ hour to monitor further ethylene uptake. During the ½ hour, the ethylene pressure decreased by 50 psi. The reaction temperature was maintained under 60° C. by cooling water circulation system. The resulting product was washed with a methanol/HCl mixture and deionized (DI) water and then dried in a vacuum oven at 60° C. overnight. 4.7 g of white polyethylene polymer was collected. Polymer Polyethylene analysis: M$_w$=1,958,584; M$_w$/M$_n$=1.75; and Peak DSC M.P: 135.4° C.

Compartive Example 1
Polymerization of Ethylene in a Parr Reactor in the Presence of VCl$_3$(THF)$_3$ and Cocatalyst in Toluene:

1.20×10$^{-4}$ moles (6 mg) of VCl$_3$(THF)$_3$ was dissolved in 50 ml of toluene in a Parr reactor. The color of the solution turned brown and VCl$_3$(THF)$_3$ was somewhat soluble. Upon addition of 1.2 g (approx. 100 molar eq.) of MAO, 10 wt. % solution in toluene, the color of the solution instantaneously changed to dark red brown. The reaction was allowed to proceed for 1.5 hours under the constant pressure of ethylene (@300 psig), after which the ethylene supply was closed to monitor ethylene uptake. A 0.5 hour after the ethylene supply was closed, the pressure had decreased by 130 psi. Over the course of the reaction, the reaction temperature was maintained under 60° C. with a water circulation pump. The resulting product was washed with a methanol/HCl mixture and deionized (DI) water and then dried in a vacuum oven at 60° C. overnight. 8.0 g of white polyethylene granules were collected. Polymer analysis: M$_w$=2,042,158; M$_w$/M$_n$=1.73 and Peak DSC M.P: 132.1° C.

Example 16
Copolymerization of Ethylene and 1-Hexene in a Parr Reactor in the Presence of (Ph)$_2$nacnacVCl$_2$(THF)$_2$ And Cocatalyst in CH$_2$Cl$_2$:

7.76×10$^{-5}$ moles (40 mg) of (Ph)$_2$nacnacVCl$_2$(THF)$_2$, reference Example 1B, was dissolved in 100 ml of CH$_2$Cl$_2$ and 7.3 g (approx. 100 molar eq.) MAO, 10 wt. % solution in toluene, was added to the solution and placed in a Parr reactor. 40 ml of dry 1-hexene was added to the reaction mixture. Ethylene (@350 psig) was introduced into the reactor and the ethylene supply was closed. After one minute, the temperature had increased to 52° C. The temperature then decreased slowly and stayed at 45° C. The reactor was stirred for an hour. When the reactor was opened to the atmosphere, the entire reactor was filled with white sticky polymer. The restulting product was washed with a methanol/HCl mixture and deionized (DI) water and then dried in a vacuum oven at 60° C. overnight. 23.6 g of polymer were collected. Polymer analysis: M$_w$=707,048; M$_w$/M$_n$=212.33; and total carbons on side chain/1000 carbons by $^{13}$C NMR: 48.3.

Example 17
Polymerization of 1-Hexene in the Presence of (Ph)$_2$nacnacV(Me)$_2$ and Cocatalyst in CH$_2$Cl$_2$:

6.04×10$^{-5}$ moles (20 mg) of (Ph)$_2$nacnacV(Me)$_2$, reference Example 3A, was dissolved in 40 ml of dry CH$_2$Cl$_2$ in an ampoule. MAO (approx. 100 molar eq. in toluene) was added into the solution of (Ph)$_2$nacnacV(Me)$_2$ in the ampoule and the ampoule was closed with a Teflon tap. After two cycles of freeze/pump/thaw, approx. 5 ml of 1-hexene was condensed into the ampoule. When the reaction mixture was stirred at room temperature for two hours, there was no apparent change in color or viscosity of the reaction mixture. The oil bath temperature was elevated to 80° C. and stirred overnight. The solution turned dark orange and became very viscous when cooled down to room temperature. The ampoule was opened to atmosphere and a MeOH/HCl solution was added to wash the resulting product. However, the dark orange color was not removed. All the volatile species were removed by distillation leaving a very dark brown oil. Polymer analysis: $^1$H NMR (CDC$_{13}$): broad peaks at δ 2.1, 1.3, 1.2, 0.8 ppm. Analysis of the resulting product indicated formation of oligomers, mostly dimers to hexamers, which included branched oligomers.

Example 18
Polymerization of Ethylene in the Presence of (Ph)$_2$nacnacTiCl$_2$(THF)$_2$ and Cocatalyst in CH$_2$Cl$_2$:

3.91×10$^{-5}$ moles (20 mg) of (Ph)$_2$nacnacTiCl$_2$(THF)$_2$, reference Example 1A, was dissolved in 50 ml of CH$_2$Cl$_2$ in a 100 ml Schlenk flask equipped with a stirring bar. 7.3 g of MAO, 10 wt. % in toluene, was added to the brown solution of (Ph)$_2$nacnacTiCl$_2$(THF)$_2$ and Teflon stopper equipped with a needle valve was attached. After two cycles of freeze/pump/thaw, ethylene (@1 atm.) was introduced into the flask at room temperature. Every five minutes over a 1 hour period, the decrease in pressure was monitored. A white powder of polyethylene (160 mg) was produced in one hour. Polymer analysis: $M_w$=195,015, $M_w/M_w$=21.11; and M.P by DSC=130.6° C.

Example 19
Polymerization of Ethylene in a Parr Reactor in the Presence of $(Ph)_2nacnacTiCl_2(THF)_2$ and Cocatalyst in $CH_2Cl_2$:

$1.57 \times 10^{-5}$ moles (8 mg) of $(Ph)_2nacnacTiCl_2(THF)_2$, reference 1A, was dissolved in 50 ml of $CH_2Cl_2$ and 1.2 g (approx. 100 molar eq.) of MAO, 10 wt. % solution in toluene, was added to the solution and the solution was placed into a Parr Reactor. The reaction was allowed to proceed for 1 hour under the constant pressure of ethylene (@300 psig), after which the ethylene supply was closed and the ethylene pressure decrease was monitored over the next 0.5 hour. However, there was no further decrease in ethylene pressure. The resulting product was washed with a methanol/HCl mixture and deionized (DI) water and then dried in a vacuum oven at 60° C. overnight. 6.1 g of white polyethylene granules were isolated. Polymer analysis: $M_w$=685,963; $M_w/M_n$=30.9; and M.P by DSC=132.2° C.

Example 20
Copolynmerization of Ethylene and 1-Hexene in a Parr Reactor in the Presence of $(Ph)_2nacnacTiCl_2(THF)_2$ and Cocatalyst in $CH_2Cl_2$:

$3.90 \times 10^{-5}$ moles (20 mg) of $(Ph)_2nacnacTiCl_2(THF)_2$, reference Example 1A, and 8.0 g (approx. 200 molar eq.) MAO,10 wt. % solution in toluene, were dissolved in the mixture of 1-hexene (30 ml) and $CH_2Cl_2$ (60 ml). This solution was placed in a Parr reactor. When ethylene (@350 psig) was introduced into the reactor, the temperature rapidly increased to 52° C. within a minute. The reaction was quenched after 25 minutes since the temperature suddenly increased very rapidly to 140° C. When the reactor was opened to atmosphere, a light brown rubbery polymer was observed. . The resulting product was washed with a methanol/HCl mixture and deionized (DI) water and then dried in a vacuum oven at 60° C. overnight. 12.5 g of polymer were collected. Polymer analysis: $M_w$=33,882; $M_w/M_n$=218.51; and total carbons on side chain/1000 carbons, by $^{13}C$ NMR=34.6.

Example 21
Polymerization of 1-Hexene in the Presence of $(Ph)_2nacnacTiCl_2(THF)_2$ and Cocatalyst in $CH_2Cl_2$:

The reaction was performed with $3.90 \times 10^{-5}$ moles (20 mg) of $(Ph)_2nacnacTiCl_2(THF)_2$, reference Example 1A, MAO (100 eq.) solution and 5 ml of 1-hexene in 20 ml of $CH_2Cl_2$ in an ampoule sealed with a Teflon stopper. After stirring for two hours at room temperature, the ampoule was allowed to stir at 80° C. overnight. The solution turned to dark orange and became very viscous when cooled down to room temperature. The ampoule was opened to atmosphere. The resulting product was washed but the dark orange color was not removed. All the volatile species were removed by distillation to give a very dark brown oil. Analysis of the resulting product indicated formation of oligomers, mostly dimers to hexamers, which included branched oligomers.

Example 22
Polymerization of Ethylene in a Parr Reactor in the Presence of $(Ph)_2nacnacTiCl_2(THF)_2$ and Cocatalyst in Toluene:

$1.20 \times 10^{-5}$ moles (8 mg) of $(Ph)_2nacnacTiCl_2(THF)_2$, reference Example 1A, was dissolved in 50 ml of toluene in a Parr reactor. 1.2 g (approx. 100 molar eq.) of MAO, 10 wt. % solution in toluene, was added to the solution. The reaction temperature was kept below 60° C. by circulating cooling water. The reaction proceeded for 1 hour under constant pressure maintained by ethylene (@300 psig), after which the ethylene supply was closed. The reaction was continued, with stirring, for another 0.5 hour to monitor further ethylene uptake. During that 0.5 hour, the pressure decreased by 100 psi. The resulting product was washed with a methanol/HCl mixture and deionized (DI) water and then dried in a vacuum oven at 60° C. overnight. 10.5 g of white polyethylene granules were collected. Polymer analysis: $M_w$=818,850; $M_w/M_n$=28.58; and Peak DSC M.P: 134.2° C.

Comparative Example 2
Polymerization of Ethylene in a Parr Reactor in the Presence of $TiCl_3(THF)_3$, and Cocatalyst in Toluene:

$1.20 \times 10^{-4}$ moles (6 mg) of $TiCl_3(THF)_3$ was dissolved in 50 ml of toluene in a Parr reactor. 1.2 g (approx. 100 molar eq.) of MAO, 10 wt. % solution in toluene, was added to the $TiCl_3(THF)_3$ solution. Upon addition of MAO, the color of the $TiCl_3(THF)_3$ solution changed instantaneously a darker brown. The reaction temperature was kept under 60° C. by circulating cooling water. The reaction proceeded for 1 hour under constant pressure maintained by ethylene (@300 psig), after which the ethylene supply was closed. The reaction was continued for another 0.5 hour during which the pressure decreased only 25 psi. The resulting product was washed with a methanol/HCl mixture and deionized (DI) water and then dried in a vacuum oven at 60° C. overnight. 3.4 g of white polymer granules were collected. Polymer analysis: $M_w$=1,479,060; $M_w/M_n$=153.12; Peak DSC M.P: 134.2° C.

Example 23
Polymerization of Ethylene in a Parr Reactor in the Presence of $(Ph)_2nacnacCrCl_2(THF)_2$ and Cocatalyst in $CH_2Cl_2$:

$7.76 \times 10^{-5}$ moles (40 mg) $(Ph)_2nacnacCrCl_2(THF)_2$, reference Example 1C, and 7.3 g (approx. 100 molar eq.) of MAO, 10 wt. % solution in toluene, were dissolved in 100 ml of $CH_2Cl_2$ and the solution was placed in a Parr reactor. Ethylene (@400 psig) was supplied to the reactor. Once the reactor was pressurized, the ethylene supply was shutoff. With stirring, the temperature increased slowly to a maximum of 110° C., after which is decreased slowly. After stirring for 30 minutes, a white powder of polyethylene was obtained. The resulting powder was washed with a methanol/HCl mixture and deionized (DI) water and then dried in a vacuum oven at 60° C. overnight. 6.0 g of white polymer powder was collected. Polymer analysis: $M_w$=48,613 and $M_w/M_n$=22.84.

Example 24
Polymerization of Ethylene in a Parr Reactor in the Presence of $(Ph)_2nacnacCrCl_2(THF)_2$ and Cocatalyst in Toluene:

$1.20 \times 10^{-5}$ moles (8 mg) $(Ph)_2nacnacCrCl_2(THF)_2$, reference Example 1C, and 1.2 g (approx. 100 molar eq.) of MAO, 10 wt. % solution in toluene, were dissolved in 50 ml of toluene in a Parr reactor. Ethylene (@300 psig) was supplied to the reactor. After stirring for 1 hour under constant ethylene pressure with cooling, the ethylene supply was closed. Over the course of the following 45 minutes, the ethylene pressure decreased by 100 psi. The resulting product was washed with a methanollHCl mixture and deionized (DI) water and then dried in a vacuum oven at 60° C. overnight. 10.5 g of a white solid polymer was isolated. Polymer analysis: $M_w$: 1,157,039; $M_w/M_n$: 72.81; and Peak DSC M.P: 134.9° C.

Comparative Example 3
Polymerization of Ethylene in a Parr Reactor in the Presence of $CrCl_3(THF)_3$ and Cocatalyst in Toluene:

$1.20 \times 10^{-4}$ moles (6 mg) of $CrCl_3(THF)_3$ was dissolved in 50 ml of toluene in a Parr reactor. 1.2 g (approx. 100 molar eq.) of MAO, 10 wt. % solution in toluene, was added to the $CrCl_3(THF)_3$ solution. Upon addition of MAO, the color of the solution was pale brown even after stirring for 10 minutes and solid $CrCl_3(THF)_3$ remained. The reaction proceeded for 1 hour under constant pressure maintained by ethylene supplied @300 psig. The ethylene supply was closed and there was no observable pressure decrease over the next 30 minutes. The reaction temperature remained essentially constant, around 23° C., throughout the reaction time, even without cooling. The resulting product was washed with a methanol/HCl mixture and deionized (DI) water and then dried in a vacuum oven at 60° C. overnight. 0.5 g of polyethylene were obtained. Polymer analysis: $M_w$=1,319,817; $M_w/M_n$=37.88; and Peak DSC M.P: 133.3° C.

Example 25
Copolymerization of Ethylene and 1-Hexene in a Parr Reactor in the Presence of $(Ph)_2nacnacCrCl_2(THF)_2$ and Cocatalyst in $CH_2Cl_2$:

The reaction was performed with $7.76 \times 10^{-5}$ moles (40 mg) of $(Ph)_2nacnacCrCl_2(THF)_2$, reference Example 1C, and 7.5 g (approx. 100 molar eq.) of MAO, 10 wt. % solution in toluene, in a solvent mixture of 40 ml of 1-hexene and 60 ml of $CH_2Cl_2$ in a Parr reactor. Ethylene (@350 psig) was supplied to the Parr reactor in accordance with the procedure set forth in Example 22. 8.7 g of white polymer powder was collected. Polymer analysis: $M_w$=9,659, $M_w/M_n$:=7, M.P. by DSC=109.6 and 125.4° C. and SCB=16.

Example 26
Copolymerization of Ethylene and Propylene in a Parr Reactor in the Presence of $(Ph)_2nacnacCrCl_2(THF)_2$ and Cocatalyst:

8 mg $(Ph)nacnacCrCl_2(THF)_2$ and 100 molar equivalents of MAO solution was dissolved in 50 ml of toluene in a Parr reactor. A gas mixture of ethylene and propylene (@100 psig) was charged into the reactor. After stirring for three hours the reaction was terminated. The resulting product was washed with a methanol/HCl mixture and deionized (DI) water and then dried in a vacuum oven at 60° C. overnight. 250 mg of white rubbery polymer was isolated. Polymer analysis: $M_w$=147,054, $M_w/M_n$:=82.14, M.P. by DSC=95.1, 113.8 and 125.1° C., and SCB=9.69.

Example 27
Polymerization of Propylene in a Parr Reactor in the Presence of $(Ph)_2nacnacCrCl_2(THF)_2$ and Cocatalyst:

Attempts to polymerize propylene using reaction conditions similar to those set forth resulted in a product that could not be readily characterized using the techniques employed herein. Additional test using the corresponding Vanadium and Titanium catalyst equally provided a product that could not be readily characterized.

Example 28
Copolymerization of Ethylene and Propylene in a Parr Reactor in the Presence of $(Ph)_2nacnacVCl_2(THF)_2$ and Cocatalyst:

8 mg. $(Ph)_2nacnacVCl_2(THF)_2$ and 100 molar equivalents of MAO solution was dissolved in 50 ml of toluene in a Parr reactor. A gas mixture gas of ethylene and propylene (@100 psi) was charged into the reactor. After stirring for three hours the reaction was terminated. After washing and drying 800 mg of white rubbery polymer was isolated. Polymer analysis: $M_w$=1,476,492 $M_w/M_n$:=3.94, M.P. by DSC=17.4° C., and SCB=14.88.

Example 29
Polymerization of Ethylene in a Parr Reactor with $[(Ph)_2nacnac]_2CrCl$ and methylaluminoxane (MAO) Cocatalyst in $CH_2Cl_2$:

7 mg., 1.20 moles $[(Ph)_2nacnac]_2CrCl$, reference Example 6B, as dissolved in 50 ml of $CH_2Cl_2$ and MAO (1.23 g, 10 wt% solution in toluene, 100 eq.) was added to the solution. Ethylene (@300 psi) was charged into the reactor and kept at constant pressure. At 78° C. the temperature was lowered by cooling with a water/ice circulation pump. After one hour the polymerization was stopped and the reactor was opened yielding a white-pinkish polymer. After washing and drying under vacuum, 20.05 grams of polymer were isolated. Polymer analysis: $M_w$=350,052 $M_w/M_n$:=49.5, M.P. by DSC=136.7° C.

Example 30
Copolymerization of Ethylene with 1-hexene in a Parr Reactor with $[(Ph)_2nacnac]_2CrCl$ and Methylaluminoxane (MAO) Cocatalyst in Toluene:

15 mg of $[(Ph)_2nacnac]_2CrCl$, reference Example 6B, was dissolved in 50 ml of toluene and MAO (1.25 g, 10 wt% solution in toluene, 100 eq.) was added to the solution. 23.1 g of dried 1-hexene was added to the reaction mixture. Ethylene (@300 psi) was charged into the reactor. After one hour of stirring the ethylene supply was closed. After washing and drying under vacuum, 1.6 grams of polymer were isolated. $M_w$=916,214, $M_w$=28,365, $M_w/M_n$=32.30 M.P. by DSC=131.4° C.

Example 31
Preparation of Bis-[2,4-Pentane di(N-2,6-diisopropyl phenyl) Iminato Chromium (II)] Chloride, $[(2,6-^iPr_2Ph)_2nacnacCr(\mu-Cl)]_2$:

10.8 mmole (4.530 g) of $(2,6-^iPrPh)nacnacH$ was dissolved in 50 ml of ether and cooled to −30° C. 10.8 mmole (5.4 ml, 2.0M) of BuLi was slowly added with stirring and allowed to warm to room temperature. The reaction mixture was stirred at room temperature for 30 minutes. The resulting solution was then slowly added to a suspension of 10.8 mmole (1.330 g) of $CrCl_2$ in 125 ml of ether. After stirring overnight the reaction mixture was filtered to remove LiCl and a dark green solution was obtained. Concentration and cooling to −30° C. yielded green crystals. After drying under vacuum, 7.54 mmole (3.807 g, 69%) of $[(2,6-^iPr_2Ph)_2nacnacCrCl]_2$ was isolated. Analysis provided the following results: $^1H$ NMR ($CD_2Cl_2$): 125.86 (br, 6H), 8.53 (br, 24H), 7.55 (br, 6H), 6.44 (br, 4H), 3.89 (br, 2H) ppm. IR (KBr): 3055 (w), 2962 (s), 2926 (s), 2867 (m), 1526 (s), 1462(s), 1437(s), 1386(s), 1371 (s), 1317(s), 1254(m), 1175(w), 1101 (w), 1056 (w), 1029 (w), 959 (m), 798 (m), 758 (m) $cm^{-1}$. UV/Vis ($Et_2O$): 451 ($\epsilon$=326.9 $M^{-1}$ $cm^{-1}$), 620 ($\epsilon$=182.2 $M^{-1}$ $cm^{-1}$), 626 ($\epsilon$=181.9 $M^{-1}$ $cm^{-1}$) nm. MP: >400° C. $\mu_{eff}$= 5.2(1) $\mu_B$/Cr (294K). Mass Spectrum, m/z (%): 1008 (1.46) [$M^+$], 504 (96.68) [$M^+/2$], 469 (88.5) [$M^+/2$-Cl].

Figure 7:
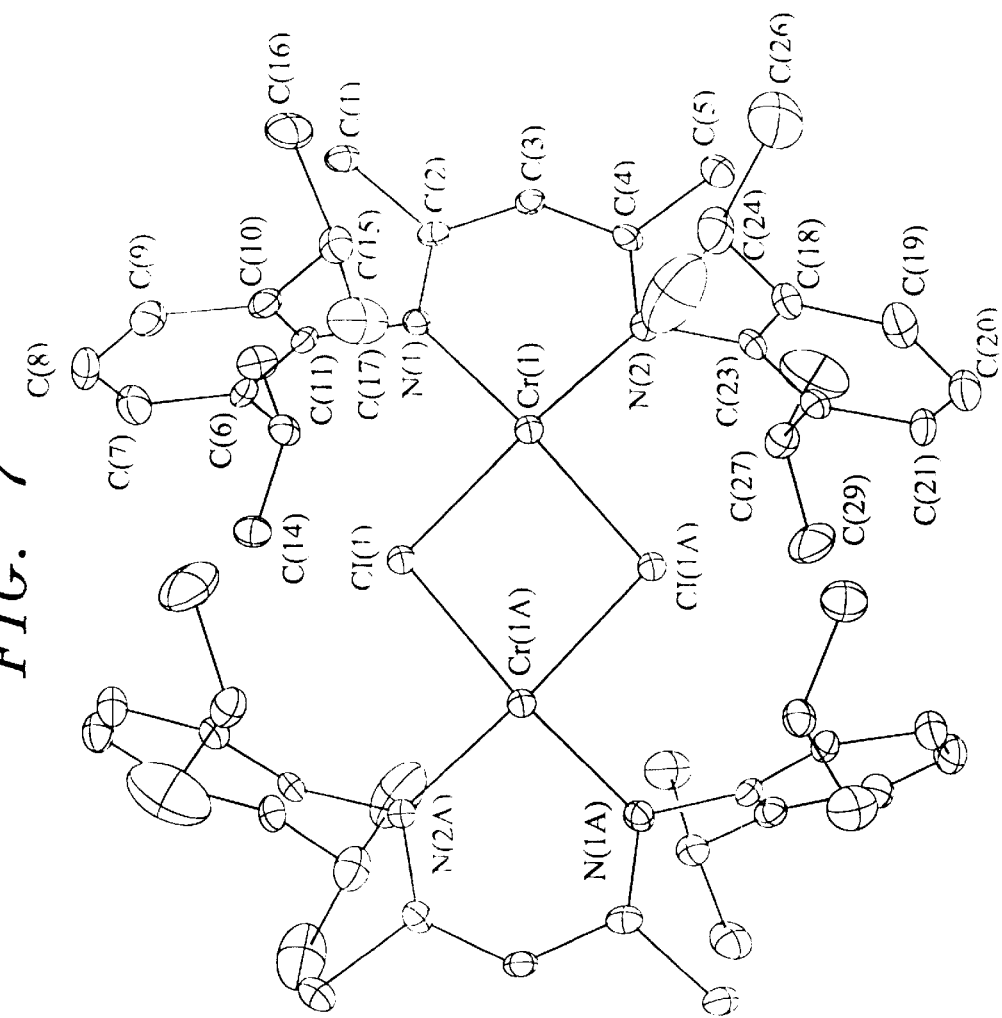
FIG. 7 depicts the crystal structure of the [(2,6-$^1$Pr$_2$Ph)$_2$nacnacCr($\mu$-Cl)]$_2$ prepared in Example 31.

The resulting compounds were analytically tested and the results are shown in Tables 31.1–2. The single crystal X-ray diffraction results are shown in FIG. 7.

TABLE 31.1

Interatomic Distances and Angles for
[(2,6-$^{i}$Pr$_2$Ph)$_2$nacnacCr($\mu$-Cl)]$_2$

| Bond | Distance (Å) | Bond | Distance (Å) |
|---|---|---|---|
| Cr(1)-N(1) | 2.042(3) | Cr(1)-N(2) | 2.058(3) |
| Cr(1)-Cl(1)#1 | 2.3895(11) | Cr(1)-Cl(1) | 2.4042(1) |
| Cl(1)-Cr(1)#(1) | 2.3895(11) | N(1)-C(2) | 1.337(5) |
| N(1)-C(11) | 1.461(4) | N(2)-C(4) | 1.334(5) |
| N(2)-C(23) | 1.466(5) | C(1)-C(2) | 1.619(5) |
| C(2)-C(3) | 1.400(5) | C(3)-C(4) | 1.396(5) |
| C(4)-C(5) | 1.514(5) | C(6)-C(11) | 1.390(5) |
| C(6)-C(7) | 1.406(5) | C(6)-C(12) | 1.535(5) |
| C(7)-C(8) | 1.379(5) | C(8)-C(9) | 1.374(6) |
| C(9)-C(10) | 1.398(5) | C(10)-C(11) | 1.414(5) |
| C(10)-C(15) | 1.516(5) | C(12)-C(13) | 1.527(6) |
| C(12)-C(14) | 1.528(5) | C(15)-C(17) | 1.533(6) |
| C(15)-C(16) | 1.533(5) | C(18)-C(19) | 1.396(6) |
| C(18)-C(23) | 1.399(5) | C(18)-C(24) | 1.525(6) |
| C(19)-C(20) | 1.398(6) | C(20)-C(21) | 1.377(7) |
| C(21)-C(22) | 1.404(6) | C(22)-C(23) | 1.410(5) |
| C(22)-C(27) | 1.523(6) | C(24)-C(25) | 1.526(8) |
| C(24)-C(26) | 1.552(7) | C(27)-C(28) | 1.517(7) |
| C(27)-C(29) | 1.522(6) | | |

| Bond Angle | Angle (deg.) | Bond Angle | Angle (deg.) |
|---|---|---|---|
| N(1)-Cr(1)-N(3) | 90.70(11) | N(1)-Cr(1)-Cl(1)#1 | 174.27(8) |
| N(2)-Cr(1)-Cl(1)#1 | 94.98(9) | N(1)-Cr(1)-Cl(1) | 93.08(8) |
| N(2)-Cr(1)-Cl(1) | 176.18(9) | Cl(1)#1-Cr(1)-Cl(1) | 81.23(4) |
| Cr(1)#1-Cl(1)-Cr(1) | 98.77(4) | C(2)-N(1)-C(11) | 115.4(3) |
| C(2)-N(1)-Cr(1) | 125.7(2) | C(11)-N(2)-Cr(1) | 118.9(2) |
| C(4)-N(1)-C(23) | 116.3(3) | C(4)-N(2)-Cr(1) | 125.0(2) |
| C(23)-N(2)-Cr(1) | 118.4(2) | N(1)-C(2)-C(3) | 123.5(3) |
| N(1)-C(2)-C(1) | 120.7(3) | C(3)-C(2)-C(1) | 115.7(3) |
| C(4)-C(3)-C(2) | 128.9(3) | N(2)-C(4)-C(3) | 123.8(3) |
| N(2)-C(4)-C(5) | 120.7(3) | C(3)-C(4)-C(5) | 115.3(3) |
| C(11)-C(6)-C(7) | 118.3(3) | C(11)-C(6)-C(12) | 122.5(3) |
| C(7)-C(6)-C(12) | 119.2(3) | C(8)-C(7)-C(6) | 120.5(4) |
| C(9)-C(8)-C(7) | 120.6(4) | C(8)-C(9)-C(10) | 121.3(4) |
| C(9)-C(10)-C(11) | 117.6(3) | C(9)-C(10)-C(15) | 120.0(3) |
| C(11)-C(10)-C(15) | 122.4(3) | C(6)-C(11)-C(10) | 121.7(3) |
| C(6)-C(11)-N(1) | 119.8(3) | C(10)-C(11)-N(1) | 118.5(3) |
| C(13)-C(12)-C(14) | 110.0(3) | C(13)-C(12)-C(6) | 111.6(3) |
| C(14)-C(12)-C(6) | 112.6(3) | C(10)-C(15)-C(17) | 110.5(3) |
| C(10)-C(15)-C(16) | 112.5(3) | C(17)-C(15)-C(16) | 108.9(4) |
| C(19)-C(18)-C(23) | 118.3(3) | C(19)-C(18)-C(24) | 119.6(4) |
| C(23)-C(18)-C(24) | 122.0(4) | C(18)-C(19)-C(20) | 120.8(4) |
| C(21)-C(20)-C(19) | 119.9(4) | C(20)-C(21)-C(22) | 121.6(4) |
| C(21)-C(22)-C(23) | 117.4(4) | C(21)-C(22)-C(27) | 119.6(4) |
| C(23)-C(22)-C(27) | 123.1(4) | C(18)-C(23)-C(22) | 122.0(4) |
| C(18)-C(23)-N(2) | 118.4(3) | C(22)-C(23)-N(2) | 119.6(3) |
| C(18)-C(24)-C(25) | 110.3(4) | C(18)-C(24)-C(26) | 111.2(4) |
| C(25)-C(24)-C(26) | 112.2(5) | C(28)-C(27)-C(29) | 110.4(5) |
| C(28)-C(27)-C(22) | 111.7(4) | C(29)-C(27)-C(22) | 113.1(4) |

(Note: the bond designations are with reference to FIG. 6 and the values noted in parentheses after the distances and angles represent the estimated standard deviation.)

TABLE 31-2

Structure Determination Summary for
[(2,6-$^{i}$Pr$_2$Ph)$_2$nacnacCr($\mu$-Cl)]$_2$ Crystal Data and Structure Refinement

| | |
|---|---|
| Empirical Formula | C$_{58}$H$_{82}$Cl$_2$Cr$_2$N$_4$ |
| Formula Weight | 1010.18 |
| Temperature | 173(2) |
| Wavelength | 0.71073 Å |
| Crystal System | Monoclinic |
| Space Group | P2$_1$/n |
| Unit Cell Dimensions | a = 9.1807(2)Å |
| | b = 14.4077(2)Å |
| | c = 21.1565(3)Å |

TABLE 31-2-continued

Structure Determination Summary for
[(2,6-$^{i}$Pr$_2$Ph)$_2$nacnacCr($\mu$-Cl)]$_2$

| | |
|---|---|
| | $\alpha$ = 90° |
| | $\beta$ = 91.9075° |
| | $\gamma$ = 90° |
| Volume | 2796.85(5)Å$^3$ |
| Z | 2 |
| Density (calc.) | 1.200 g/cm$^3$ |
| Absorption Coefficient | 0.523 mm$^{-1}$ |
| F(000) | 1080 |
| Crystal size | 0.40 × 0.30 0.15 mm |
| Crystal color | Deep purple block |
| $\theta$ range for data collection | 1.71 to 25.00° |
| Limiting indices | $-10 \leq h \leq 9, -15 \leq k \leq 17,$ |
| | $-24 \leq 1 \leq 25$ |
| Reflections Collected | 13676 |
| Independent Reflections | 4902 (R$_{int}$ = 0.0626%) |
| Absorption correction | None |
| Refinement Method | Full-Matrix least-squares on F$^2$ |
| Data/restraints/parameters | 4902/0/298 |
| Goodness-of-fit on F$^2$ | 1.346 |
| Final R indices [I > 2$\sigma$(I)] | R1 = 0.0633, wR2 = 0.1757 |
| R indices (all data) | R1 = 0.0886, wR2 = 0.1981 |
| Largest diff. peak and hole | 0.459 and $-0.469$ eÅ$^{-3}$ |

Example 32

Preparation of Bis-[2,4-Pentane-di(N-2,6-diisopropylphenyl)iminato Methyl] Chromium (II), [(2,6-$^{i}$Pr$_2$Ph)$_2$nacnacCr($\mu$-Me)]$_2$:

0.297 mmole (0.301 mg) of [(2,6-$^{i}$Pr$_2$Ph)$_2$nacnacCrCl]$_2$, as prepared in Example 31, was dissolved in 40 ml of ether and cooled to $-30°$ C. 0.426 ml (2 eq) of MeLi (1.4 M in ether, 0.594 mmole) was slowly added with stirring. The color of the solution quickly changed from dark green to brown-red. The reaction mixture was stirred for one hour and then filtered. The filtrate was concentrated and cooled to $-30°$ C. for crystallization. Dark purple crystals (0.175 g, 61%) were isolated by filtration and dried under vacuum. $^1$H NMR (C$_6$D$_6$): $\delta$ 12.81(b), 7.07(b), 3.04(b), 1.33(b) ppm. IR (KBr): 3056(w), 2956(s), 2925(s), 2866(s), 1520(s), 1461(s), 1435(s), 1401(s), 1309(s), 1253(s), 1171(m), 1099(m), 1067(w), 1022(w), 933(w), 850(w), 793(m), 761(m) cm. UV/Vis (Et$_2$O): $\lambda_{max}$ ($\epsilon$)=480 (573 M$^{-1}$ cm$^{-1}$), 540 (305.1 M$^{-1}$ cm$^{-1}$) nm. Mp: 201–203° C. $\mu_{eff}$=1.8(1$\mu_B$/Cr (294 K). Mass Spectrum, m/z (%): 953 (3.63) [M$^+$—CH$_3$], 469 (100) [M$^+$/2—CH$_3$].

Figure 8:
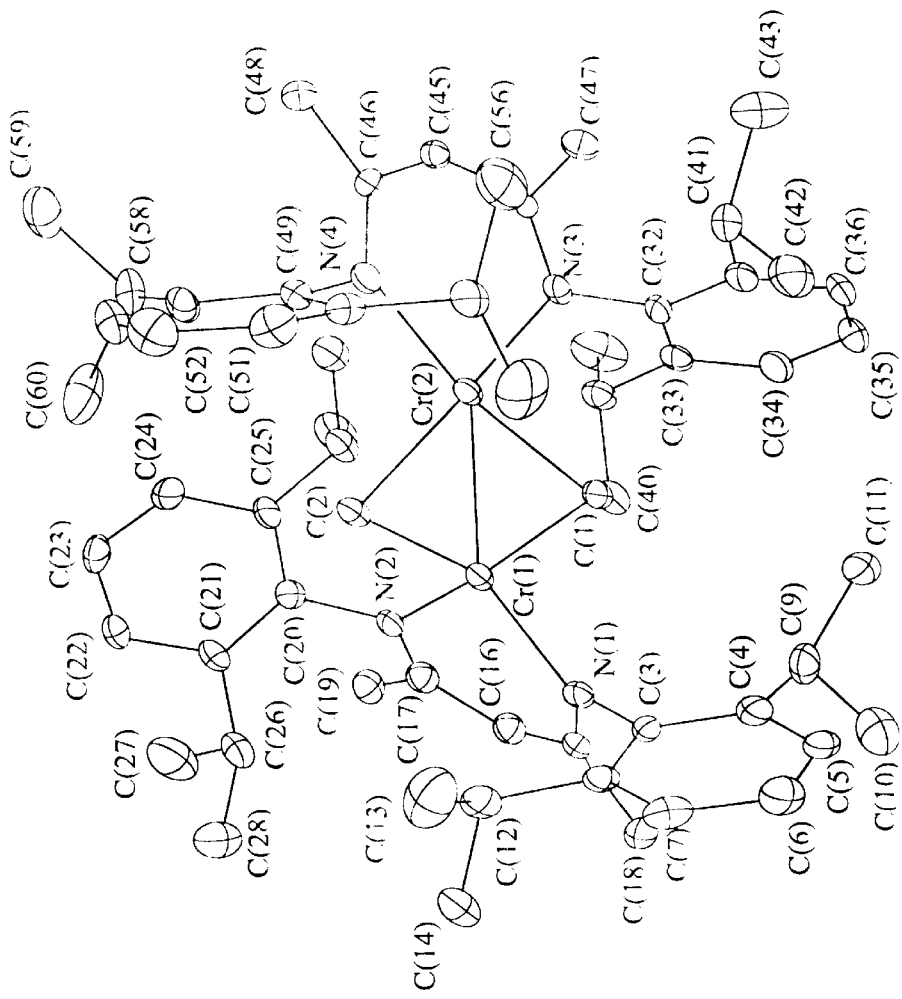
FIG. 8 depicts the crystal structure of the [(2,6-$^1$Pr$_2$Ph)$_2$nacnacCr($\mu$-Me)]$_2$ prepared in Example 32.

The resulting compounds were analytically tested and the results are shown in Tables 32. 1–2. The single crystal X-ray diffraction results are shown in FIG. 8.

TABLE 32.1

Interatomic Distances and Angles for
[(2,6-$^{i}$Pr$_2$Ph)$_2$nacnacCr($\mu$-Me)]$_2$

| Bond | Distance (Å) | Bond | Distance (Å) |
|---|---|---|---|
| Cr(1)-N(2) | 2.063(4) | Cr(1)-N(1) | 2.116(4) |
| Cr(1)-C(3) | 2.192(6) | Cr(1)-C(1) | 2.225(5) |
| Cr(1)-Cr(3) | 2.5967(10) | Cr(2)-N(3) | 2.061(4) |
| Cr(2)-N(4) | 2.111(4) | Cr(2)-C(1) | 2.200(5) |
| Cr(2)-C(2) | 2.231(5) | N(1)-C(15) | 1.325(6) |
| N(1)-C(3) | 1.449(6) | N(2)-C(17) | 1.332(6) |
| N(2)-C(20) | 1.470(6) | N(3)-C(44) | 1.340(6) |
| N(3)-C(32) | 1.454(6) | N(4)-C(46) | 1.329(6) |
| N(4)-C(49) | 1.450(6) | C(1)-H(1B) | 0.9600(10) |
| C(1)-H(1C) | 0.9600(11) | C(1)-H(1A) | 0.98(6) |
| C(2)-H(2A) | 0.99(8) | C(2)-H(2B) | 1.01(7) |

TABLE 32.1-continued

Interatomic Distances and Angles for
[(2,6-$^i$Pr$_2$Ph)$_2$nacnacCr($\mu$-Me)]$_2$

| | | | |
|---|---|---|---|
| C(2)-H(2C) | 1.02(6) | C(3)-C(4) | 1.404(7) |
| C(3)-C(8) | 1.416(7) | C(4)-C(5) | 1.399(7) |
| C(4)-C(9) | 1.499(8) | C(5)-C(6) | 1.388(9) |
| C(6)-C(7) | 1.381(9) | C(7)-C(8) | 1.377(8) |
| C(8)-C(12) | 1.539(8) | C(9)-C(11) | 1.529(9) |
| C(9)-C(10) | 1.548(9) | C(12)-C(14) | 1.525(9) |
| C(12)-C(13) | 1.530(9) | C(15)-C(16) | 1.413(7) |
| C(15)-C(18) | 1.506(7) | C(16)-C(17) | 1.399(7) |
| C(17)-C(19) | 1.513(7) | C(20)-C(25) | 1.403(7) |
| C(20)-C(21) | 1.401(7) | C(21)-C(22) | 1.407(8) |
| C(21)-C(26) | 1.514(8) | C(22)-C(23) | 1.389(9) |
| C(23)-C(24) | 1.373(9) | C(24)-C(25) | 1.392(7) |
| C(25)-C(29) | 1.523(7) | C(26)-C(27) | 1.503(9) |
| C(26)-C(28) | 1.526(9) | C(29)-C(30) | 1.528(8) |
| C(29)-C(31) | 1.529(8) | C(32)-C(33) | 1.396(8) |
| C(32)-C(37) | 1.413(7) | C(33)-C(34) | 1.389(7) |
| C(33)-C(38) | 1.537(7) | C(34)-C(35) | 1.375(8) |
| C(35)-C(36) | 1.390(8) | C(36)-C(37) | 1.388(7) |
| C(37)-C(41) | 1.524(8) | C(38)-C(39) | 1.517(8) |
| C(38)-C(40) | 1.532(8) | C(41)-C(43) | 1.530(8) |
| C(41)-C(42) | 1.530(8) | C(44)-C(45) | 1.383(7) |
| C(44)-C(47) | 1.531(7) | C(45)-C(46) | 1.405(7) |
| C(46)-C(48) | 1.521(7) | C(49)-C(50) | 1.398(7) |
| C(49)-C(54) | 1.416(7) | C(50)-C(51) | 1.404(8) |
| C(50)-C(55) | 1.516(7) | C(51)-C(52) | 1.377(9) |
| C(52)-C(53) | 1.390(9) | C(53)-C(54) | 1.390(8) |
| C(54)-C(58) | 1.509(8) | C(55)-C(56) | 1.516(8) |
| C(55)-C(57) | 1.524(8) | C(58)-C(60) | 1.535(10) |
| C(58)-C(59) | 1.540(9) | O(1)-C(61)#1 | 1.88(2) |
| O(1)-C(61) | 1.88(2) | C(62)-C(61) | 1.85(5) |

| Bond Angle | Angle (deg.) | Bond Angle | Angle (deg.) |
|---|---|---|---|
| N(2)-Cr(1)-N(1) | 90.06(16) | N(2)-Cr(1)-C(2) | 95.37(19) |
| N(1)-Cr(1)-C(2) | 147.02(18) | N(2)-Cr(1)-C(1) | 165.75(19) |
| N(1)-Cr(1)-C(1) | 91.30(18) | C(2)-Cr(1)-C(1) | 91.2(2) |
| N(2)-Cr(1)-Cr(2) | 121.48(11) | N(1)-Cr(1)-Cr(2) | 143.72(11) |
| C(2)-Cr(1)-Cr(2) | 54.75(13) | C(1)-Cr(1)-Cr(2) | 53.62(14) |
| N(3)-Cr(2)-N(4) | 90.20(16) | N(3)-Cr(2)-C(1) | 95.86(10) |
| N(4)-Cr(2)-C(1) | 147.46(19) | N(3)-Cr(2)-C(2) | 165.0(3) |
| N(4)-Cr(2)-C(2) | 91.39(18) | C(1)-Cr(2)-C(2) | 90.8(2) |
| N(3)-Cr(2)-Cr(1) | 121.21(12) | N(4)-Cr(2)-Cr(1) | 143.47(11) |
| C(1)-Cr(2)-Cr(1) | 54.52(14) | C(2)-Cr(2)-Cr(1) | 53.35(15) |
| C(15)-N(1)-C(3) | 117.7(4) | C(15)-N(1)-Cr(1) | 124.3(3) |
| C(3)-N(1)-Cr(1) | 117.4(3) | C(17)-N(2)-C(20) | 113.6(4) |
| C(17)-N(2)-Cr(1) | 123.8(3) | C(20)-N(2)-Cr(1) | 122.5(3) |
| C(44)-N(3)-C(32) | 115.5(4) | C(44)-N(3)-Cr(2) | 123.1(3) |
| C(32)-N(3)-Cr(2) | 121.4(3) | C(46)-N(4)-C(49) | 116.8(4) |
| C(46)-N(4)-Cr(2) | 124.4(3) | C(49)-N(4)-Cr(2) | 117.6(3) |
| H(1B)-C(1)-H(1C) | 116(5) | H(1B)-C(1)-H(1A) | 128(5) |
| H(1C)-C(1)-H(1A) | 97(5) | H(1B)-C(1)-Cr(2) | 119(4) |
| H(1C)-C(1)-Cr(2) | 123(4) | H(1A)-C(1)-Cr(2) | 61(4) |
| H(1B)-C(1)-Cr(1) | 98(4) | H(1C)-C(1)-Cr(1) | 86(4) |
| H(1A)-C(1)-Cr(1) | 125(4) | Cr(2)-C(1)-Cr(1) | 71.85(15) |
| H(2A)-C(2)-H(2B) | 107(5) | H(2A)-C(2)-H(2C) | 120(6) |
| H(2B)-C(2)-H(2C) | 110(5) | H(2A)-C(2)-H(1) | 118(4) |
| H(2B)-C(2)-Cr(1) | 130(3) | H(2C)-C(2)-Cr(1) | 66(3) |
| H(2A)-C(2)-Cr(2) | 99(5) | H(2B)-C(2)-Cr(2) | 80(3) |
| H(2C)-C(2)-Cr(2) | 132(3) | Cr(1)-C(2)-Cr(2) | 71.90(16) |
| C(4)-C(3)-C(8) | 120.4(5) | C(4)-C(3)-N(1) | 121.9(4) |
| C(8)-C(3)-N(1) | 117.6(4) | C(5)-C(4)-C(3) | 117.7(5) |
| C(5)-C(4)-C(9) | 117.9(5) | C(3)-C(4)-C(9) | 124.4(5) |
| C(6)-C(5)-C(4) | 122.2(5) | C(7)-C(6)-C(5) | 119.0(5) |
| C(8)-C(7)-C(6) | 121.4(6) | C(7)-C(8)-C(3) | 119.3(5) |
| C(7)-C(8)-C(12) | 119.6(5) | C(3)-C(8)-C(12) | 121.0(4) |
| C(4)-C(9)-C(11) | 112.8(6) | C(4)-C(9)-C(10) | 111.7(5) |
| C(11)-C(9)-C(10) | 107.0(5) | C(14)-C(12)-C(13) | 110.9(6) |
| C(14)-C(12)-C(8) | 110.8(5) | C(13)-C(12)-C(8) | 112.7(6) |
| N(1)-C(15)-C(16) | 122.3(4) | N(1)-C(15)-C(18) | 122.0(4) |
| C(16)-C(15)-C(18) | 115.3(4) | C(17)-C(16)-C(15) | 130.3(5) |
| N(2)-C(17)-C(16) | 123.5(5) | N(2)-C(17)-C(19) | 121.7(5) |
| C(16)-C(17)-C(19) | 114.9(5) | C(25)-C(20)-C(21) | 121.5(5) |
| C(25)-C(20)-N(2) | 120.6(4) | C(21)-C(20)-N(2) | 117.8(4) |
| C(20)-C(21)-C(22) | 118.2(5) | C(20)-C(21)-C(26) | 123.1(5) |
| C(22)-C(21)-C(26) | 118.5(5) | C(23)-C(22)-C(21) | 120.7(5) |
| C(24)-C(23)-C(22) | 119.7(5) | C(23)-C(24)-C(25) | 122.0(5) |
| C(24)-C(25)-C(20) | 117.9(5) | C(24)-C(25)-C(29) | 118.6(5) |
| C(20)-C(25)-C(29) | 123.5(4) | C(27)-C(26)-C(21) | 112.1(5) |
| C(27)-C(26)-C(28) | 109.8(5) | C(21)-C(26)-C(28) | 111.5(6) |
| C(25)-C(29)-C(30) | 110.0(5) | C(25)-C(29)-C(31) | 112.6(5) |
| C(30)-C(29)-C(31) | 110.4(5) | C(33)-C(32)-C(37) | 119.7(5) |
| C(33)-C(32)-N(3) | 121.5(4) | C(37)-C(32)-N(3) | 118.8(5) |
| C(34)-C(33)-C(32) | 119.6(5) | C(34)-C(33)-C(38) | 118.9(5) |
| C(32)-C(33)-C(38) | 121.5(5) | C(35)-C(34)-C(33) | 121.3(5) |
| C(34)-C(35)-C(36) | 119.2(5) | C(35)-C(36)-C(37) | 121.3(5) |
| C(36)-C(37)-C(32) | 118.9(5) | C(35)-C(36)-C(37) | 118.6(5) |
| C(32)-C(37)-C(41) | 122.6(5) | C(39)-C(38)-C(40) | 109.1(5) |
| C(39)-C(38)-C(33) | 112.3(5) | C(40)-C(38)-C(33) | 110.1(4) |
| C(37)-C(41)-C(43) | 111.7(5) | C(37)-C(41)-C(42) | 112.3(5) |
| C(43)-C(41)-C(42) | 109.6(5) | N(3)-C(44)-C(45) | 125.0(5) |
| N(3)-C(44)-C(47) | 119.4(5) | C(45)-C(44)-C(47) | 115.5(4) |
| C(44)-C(45)-C(46) | 129.2(5) | N(4)-C(46)-C(45) | 123.2(4) |
| N(4)-C(46)-C(48) | 121.5(5) | C(45)-C(46)-C(48) | 115.3(4) |
| C(50)-C(49)-C(54) | 121.1(5) | C(50)-C(49)-N(4) | 118.0(4) |
| C(54)-C(49)-N(4) | 120.9(4) | C(49)-C(50)-C(51) | 118.4(5) |
| C(49)-C(50)-C(55) | 122.2(5) | C(51)-C(50)-C(55) | 119.3(5) |
| C(52)-C(51)-C(50) | 121.2(6) | C(51)-C(52)-C(53) | 119.7(5) |
| C(52)-C(53)-C(54) | 121.5(5) | C(53)-C(54)-C(49) | 118.0(5) |
| C(53)-C(54)-C(58) | 118.0(5) | C(49)-C(54)-C(58) | 124.0(5) |
| C(50)-C(55)-C(56) | 110.8(5) | C(50)-C(55)-C(57) | 113.0(5) |
| C(56)-C(55)-C(57) | 111.2(6) | C(54)-C(58)-C(60) | 110.6(6) |
| C(54)-C(58)-C(59) | 112.3(5) | C(60)-C(58)-C(59) | 108.1(5) |
| C(61)#1-O(1)-C(61) | 179.998(3) | C(62)-C(61)-O(1) | 90.2(13) |

(Note: the bond designations are with reference to FIG. 6 and the values noted in parentheses after the distances and angles represent the estimated standard deviation.)

TABLE 32-2

Structure Determination Summary for
[(2,6-$^i$Pr$_2$Ph)$_2$nacnacCr($\mu$-Me)]$_2$ Crystal Data and Structure Refinement

| | |
|---|---|
| Empirical Formula | C$_{62}$H$_{93}$Cr$_2$N$_4$O$_{0.5}$ |
| Formula Weight | 1006.40 |
| Temperature | 173(2)K |
| Wavelength | 0.71073 Å |
| Crystal System | Triclinic |
| Space Group | P1 |
| Unit Cell Dimensions | a = 13.0661(3)Å |
| | b = 13.7664(3)Å |
| | c = 16.6601(4)Å |
| | α = 95.1228(6)° |
| | β = 92.0025(9)° |
| | γ = 91.1435(9)° |
| Volume | 2982.10(17)Å$^3$ |
| Z | 2 |
| Density (calc.) | 1.221 g/cm$^3$ |
| Absorption Coefficient | 0.404 mm$^{-1}$ |
| F(000) | 1090 |
| Crystal color | Dark blue plate |
| Crystal Size (mm) | 0.30 × 0.20 0.10 mm |
| 2θ range for data collection | 1.49 to 24.50° |
| Limiting indices | −13 ≤ h ≤ 15 |
| | −16 ≤ k ≤ 16 |
| | −19 ≤ l ≤ 19 |
| Reflections Collected | 17563 |
| Independent Reflections | 9495 (R$_{int}$ = 0.0561) |
| Absorption correction | None |
| Max. and min. transmission | 0.9607 and 0.8884 |
| Refinement Method | Full-Matrix least-squares on F$^2$ |
| Final R indices [I > 2σ(I)] | R1 = 0.0838, wR2 = 0.2105 |
| R indices (all data) | R1 = 0.1154, wR2 = 0.2362 |
| Largest diff. peak and hole | 0.683 and −0.836 eÅ$^{-3}$ |

Example 33

Preparation of Bis-[2,4-Pentane-di(N-2,6-diisopropylphenyl)iminato (trimethylsilylmethyl) Chromium (II), [(2,6-$^i$Pr$_2$Ph)$_2$nacnacCr(TMSM)]$_2$:

0.396 mmole of [(2,6-$^i$PrPh)nacnacCrCl]$_2$, as prepared in Example 31, was dissolved in 40 ml of diethyl ether and cooled to –30° C. 0.074 g (0.792 mmole) of TMSMLi was added as a solid with stirring. The reaction was stirred for one hour during which the color of the solution slowly changed from dark green to brown. The solvent was removed and the resulting solid was extracted with pentane. Concentrating followed by cooling to –30° C. yielded brown-green crystals (.275 g, 62%). $^1$H NMR (C$_6$D$_6$): 161 (vb), 126.1 (b), 11.4(b), 8.72(b), 7.16(vb) ppm. IR (KBr): 3056(m), 2961 (s), 2867(m), 1529(s), 1459(m), 1438(s), 1383(s), 1317(s), 1257(m), 1177(w), 1100(w), 1074(w), 1025(w), 936(w), 856(m), 796(m), 756(m). UV/Vis (Et$_2$O): $\lambda_{max}$ ($\epsilon$)=480 (114.8 M$^{-1}$ cm$^{-1}$), 510 (111.6 M$^{-1}$ cm$^{-1}$) nm. $\mu_{eff}$=5.48(1) $\mu_B$ (294K). Mp: 124–127° C.

Figure 9:
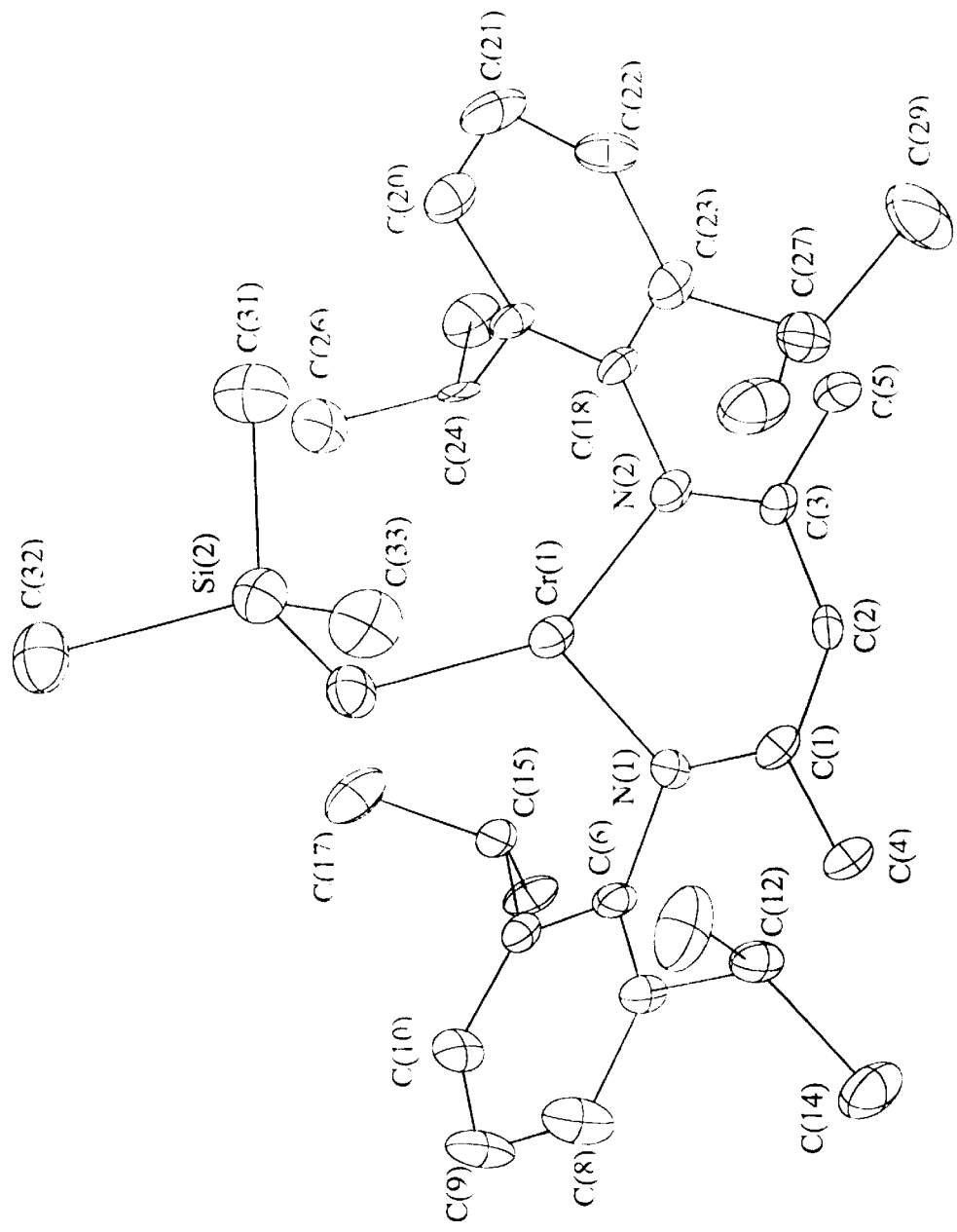
FIG. 9 depicts the crystal structure of the (2,6-$^1$Pr$_2$Ph)$_2$nacnacCr(TMSM) prepared in Example 33.

The resulting compounds were analytically tested and the results are shown in Tables 33. 1–2. The single crystal X-ray diffraction results are shown in FIG. 9.

TABLE 33.1

Interatomic Distances and Angles for [(2,6-$^i$Pr$_2$Ph)$_2$nacnacCr(TMSM)]$_2$

| Bond | Distance (Å) | Bond | Distance (Å) |
| --- | --- | --- | --- |
| Cr(1)-N(1) | 1.983(7) | Cr(1)-N(2) | 2.002(7) |
| Cr(1)-C(30) | 2.099(9) | Si(2)-C(30) | 1.859(10) |
| Si(2)-C(31) | 1.874(10) | Si(2)-C(33) | 1.877(9) |
| Si(2)-C(32) | 1.888(9) | N(1)-C(1) | 1.324(11) |
| N(1)-C(6) | 1.418(10) | N(2)-C(3) | 1.323(10) |
| N(2)-C(18) | 1.450(10) | C(1)-C(2) | 1.382(11) |
| C(1)-C(4) | 1.515(11) | C(2)-C(3) | 1.407(11) |
| C(3)-C(5) | 1.470(12) | C(6)-C(7) | 1.407(11) |
| C(6)-C(11) | 1.447(10) | C(7)-C(8) | 1.357(12) |
| C(7)-C(12) | 1.537(11) | C(8)-C(9) | 1.396(12) |
| C(9)-C(10) | 1.385(12) | C(10)-C(11) | 1.372(11) |
| C(11)-C(15) | 1.515(11) | C(12)-C(13) | 1.495(13) |
| C(12)-C(14) | 1.541(11) | C(15)-C(16) | 1.528(12) |
| C(15)-C(17) | 1.534(12) | C(18)-C(19) | 1.389(10) |
| C(18)-C(23) | 1.404(11) | C(19)-C(20) | 1.398(11) |
| C(19)-C(24) | 1.525(11) | C(20)-C(21) | 1.372(12) |
| C(21)-C(22) | 1.382(12) | C(22)-C(23) | 1.399(11) |
| C(23)-C(27) | 1.517(11) | C(24)-C(26) | 1.495(13) |
| C(24)-C(25) | 1.543(12) | C(27)-C(28) | 1.507(14) |
| C(27)-C(29) | 1.521(12) | | |

| Bond Angle | Angle (deg.) | Bond Angle | Angle (deg.) |
| --- | --- | --- | --- |
| N(1)-Cr(1)-N(2) | 89.3(3) | N(1)-Cr(1)-C(30) | 122.1(3) |
| N(2)-Cr(1)-C(30) | 147.8(3) | C(30)-Si(2)-C(31) | 111.2(5) |
| C(30)-Si(2)-C(33) | 111.6(4) | C(31)-Si(2)-C(33) | 109.0(5) |
| C(30)-Si(2)-C(32) | 112.1(4) | C(31)-Si(2)-C(32) | 105.6(5) |
| C(33)-Si(2)-C(32) | 106.9(5) | C(1)-N(1)-C(6) | 120.0(7) |
| C(1)-N(1)-Cr(1) | 128.6(6) | C(6)-N(1)-Cr(1) | 111.2(5) |
| C(3)-N(2)-C(18) | 119.1(7) | C(3)-N(2)-Cr(1) | 129.6(5) |
| C(18)-N(2)-Cr(1) | 111.3(5) | N(1)-C(1)-C(2) | 123.1(7) |
| N(1)-C(1)-C(4) | 120.1(8) | C(2)-C(1)-C(4) | 116.8(8) |
| C(1)-C(2)-C(3) | 128.3(8) | N(2)-C(3)-C(2) | 121.0(8) |
| N(2)-C(3)-C(5) | 120.4(7) | C(2)-C(3)-C(5) | 118.6(8) |
| C(7)-C(6)-N(1) | 121.4(6) | C(7)-C(6)-C(11) | 119.0(7) |
| N(1)-C(6)-C(11) | 119.4(7) | C(8)-C(7)-C(6) | 120.0(7) |
| C(8)-C(7)-C(12) | 121.1(7) | C(6)-C(7)-C(12) | 118.9(7) |
| C(7)-C(8)-C(9) | 122.2(8) | C(10)-C(9)-C(8) | 117.9(8) |
| C(11)-C(10)-C(9) | 123.0(7) | C(10)-C(11)-C(6) | 117.8(7) |
| C(10)-C(11)-C(15) | 122.3(7) | C(6)-C(11)-C(15) | 119.9(7) |
| C(13)-C(12)-C(14) | 108.7(8) | C(13)-C(12)-C(7) | 110.1(8) |
| C(14)-C(12)-C(7) | 111.6(7) | C(11)-C(15)-C(16) | 111.4(6) |
| C(11)-C(15)-C(17) | 110.3(7) | C(16)-C(15)-C(17) | 110.3(6) |
| C(19)-C(18)-C(23) | 121.9(7) | C(19)-C(18)-N(2) | 118.5(7) |
| C(23)-C(18)-N(2) | 119.5(6) | C(18)-C(19)-C(20) | 117.6(7) |
| C(18)-C(19)-C(24) | 123.8(7) | C(20)-C(19)-C(24) | 118.6(6) |

TABLE 33.1-continued

Interatomic Distances and Angles for [(2,6-$^i$Pr$_2$Ph)$_2$nacnacCr(TMSM)]$_2$

| | | | |
| --- | --- | --- | --- |
| C(21)-C(20)-C(19) | 122.0(7) | C(20)-C(21)-C(22) | 119.5(8) |
| C(21)-C(22)-C(23) | 121.0(8) | C(22)-C(23)-C(18) | 117.9(7) |
| C(22)-C(23)-C(27) | 120.0(7) | C(18)-C(23)-C(27) | 122.1(7) |
| C(26)-C(24)-C(19) | 112.5(8) | C(26)-C(24)-C(25) | 112.3(7) |
| C(19)-C(24)-C(25) | 110.7(7) | C(28)-C(27)-C(23) | 109.0(8) |
| C(28)-C(27)-C(29) | 111.1(8) | C(23)-C(27)-C(29) | 112.8(7) |
| Si(2)-C(30)-Cr(1) | 122.1(5) | | |

(Note: the bond designations are with reference to FIG. 6 and the values noted in parentheses after the distances and angles represent the estimated standard deviation.)

TABLE 33-2

Structure Determination Summary for [(2,6-$^i$Pr$_2$Ph)$_2$nacnacCr(TMSM)]$_2$

Crystal Data and Structure Refinement

| | |
| --- | --- |
| Empirical Formula | C$_{33}$H$_{52}$CrN$_2$Si |
| Formula Weight | 556.86 |
| Temperature | 173(2)K |
| Wavelength | 0.71073 Å |
| Crystal System | Monoclinic |
| Space Group | P2$_1$/n |
| Unit Cell Dimensions | a = 10.6689(2)Å |
| | b = 20.9702(4)Å |
| | c = 15.0075(3)Å |
| | α = 90° |
| | β = 95.2432(17)° |
| | γ = 90° |
| Volume | 3343.56(14)Å$^3$ |
| Z | 4 |
| Density (calc.) | 1.106 g/cm$^3$ |
| Absorption Coefficient | 0.400 mm$^{-1}$ |
| F(000) | 1208 |
| Crystal color | Brown rod |
| Crystal Size (mm) | 0.30 × 0.20 0.15 mm |
| θ range for data collection | 1.67 to 22.00° |
| Limiting indices | –10 ≦ h ≦ 11 |
| | –22 ≦ k ≦ 22 |
| | –15 ≦ 1 ≦ 8 |
| Reflections Collected | 10554 |
| Independent Reflections | 3777 (R$_{int}$ = 0.0988) |
| Absorption correction | None |
| Max. and min. transmission | 0.9425 and 0.8895 |
| Refinement Method | Full-Matrix least-squares on F$^2$ |
| Data/Restrains/Parameters | 3777/0/334 |
| Goodness-of-Fit on F$^2$ | 1.630 |
| Final R indices [I > 2σ(I)] | R = 0.0977, wR2 = 0.2370 |
| R indices (all data) | R1 = 0.1400, wR2 = 0.2657 |
| Largest difference peak and hole | 0.766 and –0.509 eÅ$^{-3}$ |

Example 34

Polymerization of Ethylene in a Parr Reactor with [(2,6-$^i$Pr$_2$Ph)$_2$nacnacCr([-Cl]$_2$ and Methylaluminoxane (MAO) Cocatalyst is Toluene:

2.0×10$^{-5}$ moles (10 mg) of [(2,6-$^i$Pr$_2$Ph)$_2$nacnacCr($\mu$-Cl]$_2$ and 1.18 g (100 eq., 10 wt. % in toluene) of MAO were dissolved in 50 ml of toluene in the Parr reactor. 300 psi of ethylene was introduced to the reactor. After stirring for 1.5 hours under constant ethylene pressure the ethylene supply was closed. Over the next 20 minutes the ethylene pressure decreased 100 psi. After washing with CH$_3$OH/HCl and drying under vacuum 11.8 g of polymer were isolated. Polymer analysis: M$_w$=276,712, M$_w$/M$_n$=13.3, M.P. by DSC: 133.

Example 35
Polymerization of Ethylene in a Parr Reactor with [(2,6-$^i$Pr Ph)nacnacCr($\mu$-Me]$_2$ and methylaluminoxane cocatalyst in toluene:

2.5×10$^{-5}$ moles (12 mg) of [(2,6-$^i$Pr$_2$Ph)$_2$nacnacCrMe]$_2$ and 1.49 g (100 eq, 10 wt. % in toluene) of MAO were dissolved in 50 ml. of toluene in the Parr reactor. 300 psi of ethylene was charged into the reactor. After stirring for 1 hour under a constant pressure of ethylene the ethylene supply was closed. Over the next 30 minutes the ethylene supply decreased by 120 psi. After washing with CH$_3$OH/HCl and drying under vacuum 10.02 g of polymer were isolated. Polymer analysis: M$_w$=200,168, M$_w$/M$_n$=15.5, M.P. by DSC: 131.9.

Example 36
Preparation of (Ph)$_2$nacnac)CrCl$_2$(THF)$_2$ on Silica Support 0.9 g of silica (having a Surface Area of 306 m$^2$/g, Pore Volume of 3.1 cm$^3$/g, and a Mean Particle Diameter of 90 microns), commercially available as MS3030 from PQ Corporation, is calcined to 400° C. and slurried in 30 ml of toluene. The slurried support was treated with a 20 ml toluene solution comprising 0.1 g of (Ph)$_2$nacnac)CrCl$_2$(THF)$_2$, as in Example 1C. The supernatant solution had been virtually completely decolorized by this time. The dark tan solid was isolated by filtration washed with toluene (5 ml) and dried in vacuo. This procedure allows for the preparation of a supported catalyst with a 1% Cr loading.

Example 37
Polymerization of Ethylene with [(2,6-$^i$PrPh)nacnacCr($\mu$-Me]$_2$ and Methylaluminoxane Cocatalyst in n-heptane:

A 1-liter autoclave reactor was charged with 0.20 g of a silica supported catalyst [(Ph$_2$nacnac)CrCl$_2$(THF)$_2$ on MS3030 silica, calcined to 400° C., 1% wt. Cr] in 400 ml of n-heptane and MAO (Albemarle) (Al/Cr=300/1). The reactor was then charged with ethylene. @300 psi and maintained at that pressure for the duration of the run. After one hour the reaction was. stopped and the polymer worked-up by treatment with 1 M HCl in MeOH, and heptane washing and drying. The reaction yielded 54 g of polymer having M$_w$: 343,580, M$_w$/M$_n$: 15.09 and a melting point of 135.3° C. it was also determined that the catalyst activity was 1.4 kgPEmol$^{-1}$ Cr.

Having described specific embodiments of the present invention, it will be understood that many modifications thereof will readily appear or may be suggested to those skilled in the art, and it is intended therefore that this invention is limited only by the spirit and scope of the following claims.

What is claimed is:

1. A process for producing polyolefins comprising polymerizing olefin monomers in the presence of a catalyst compound comprising a transition metal and a monoanioric bidentate ligand represented by Formula (II):

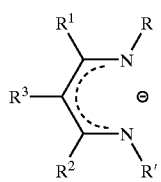

(II)

wherein
R and R' independently represent a hydrogen atom, or a substituted or unsubstituted, branched or unbranched hydrocarbyl or organosilyl radical;

R$^1$, R$^2$ and R$^3$ independently represent a hydrogen atom or a substitued or unsubstituted, branched or unbranched hydrocarbyl radical; and said transition metal is selected from a group consisting of IIIB, IVB, VB, VIB and VIIB transition metals.

2. A process for producing polyolefins comprising polymerizing olefin monomers with a supported catalyst compound comprising a transition metal and a monoanionic bidentate ligand represented by Formula (II):

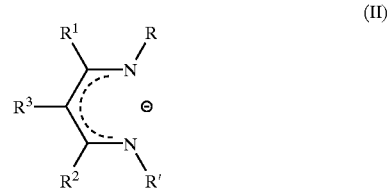

(II)

wherein
R and R' independently represent a hydrogen atom, or a substituted or unsubstituted, branched or unbranched hydrocarbyl or organosilyl radical wherein the carbon atom, directly bound to the nitrogen, has two carbon atoms bound thereto; and R$^1$, R$^2$ and R$^3$ independently represent a hydrogen atom, or a substituted or unsubstituted, branched or unbranched hydrocarbyl radical; and said transition metal is selected from a group consisting of IIIB, IVB, VB, VIB and VIIB transition metals.

3. A compound comprising a group IIIB to VIIB transition metal and at least two β-diiminate bidentate ligands, each β-diiminate bidentate ligand independently represented by Formula II:

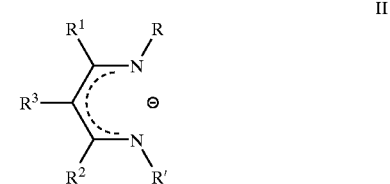

II wherein
R and R' independently represent a subslirued or unsubstituted organosilyl radical; and R$^1$, R$^2$ and R$^3$ independently represent a hydrogen atom, or a substituted or unsubstituted, branched or unbranched hydrocarbyl radical.

4. The compound of claim 3, wherein said compound is represented by the following formula I(A):

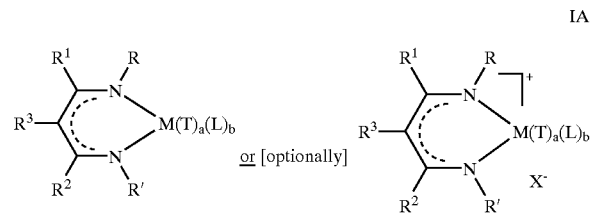

IA wherein
R, R', R$^1$, R$^2$, and R$^3$ are the same as in claim 3
M independently represents a group IIIB, IVB, VB, VIB, or VIIB transition metal;

a=an integer from 1 to 4 inclusive, b=an integer from 1 to 4 inclusive, provided a+b≦4, X⁻ represents a relatively weakly coordinated anion;

at least one L group together with at least one T group represent a β-diiminate ligand if either a or b is greater than 1, additional L groups independently represent a sigma donor stabilizing ligand, and additional T groups independently represent a univalent anionic ligand or, if more than 1 additional T groups are present, two T groups may together form other anionic ligands or an additional L group together with an additional T group may represent an additional βp-diiminate ligand.

5. A catalyst compound, useful for the polymerization of olefin monomers, wherein said catalyst compound is represented by Formula I(B) or comprises a cation represented by Formula I(B), as follows:

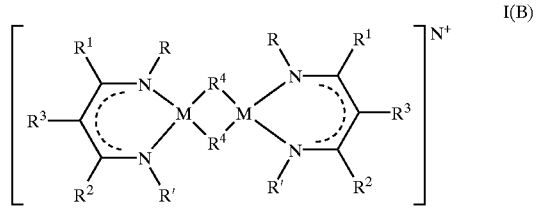

wherein

R, R', R¹, R², and R³ are the same as in claim 3;

R⁴ independently represents a bridging ligand;

M independently represents a group IIIB, IVB, VB, VIB, or VIIB transition metal; and N=an integer from 0 to 3.

6. A catalyst compound affixed to a solid support wherein said catalyst compound comprises a transition metal and a monoanionic bidentate ligand represented by Formula (II):

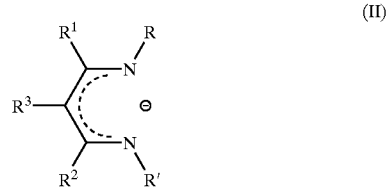

wherein

R and R' independently represent an unbranched organosilyl radical, or branched organosilyl raical, wherein the carbon, directly bound to the nitrogen, has two carbon atoms bound thereto; and R¹, R² and R³ independently represent a hydrogen atom, or a substituted or unsubstituted, branched or unbranched hydrocarbyl radical; and said transition metal is selected from a group consisting of IIIB, IVB, VB, VIB and VIIB transition metals.

7. A catalyst compound useful for the polymerization of olefin monomers, said catalyst compound comprising a transition metal and a monoanionic bidentate ligand represented by Formula II:

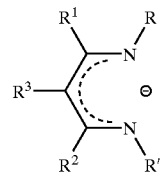

wherein

R and R' independently represent a 2,6-diisopropylphenyl, 2,6-dimethylphenyl, 2,6-diethylphenyl, 2,4,6-trimethylphenyl or 2-t-butylphenyl radical;

R¹, R² and R³ independently represent a hydrogen atom, or a substituted or unsubstituted, branched or unbranched hydrocarbyl radical; and said transition metal is selected from the group consisting of IIIB, IVB, VB, VIB, or VIIB.

8. The catalyst compound of claim 7 wherein said transition metal is a group IVB, VB, or VIB transition metal.

9. The catalyst compound of claim 8, wherein said transition metal is selected from the group consisting of titanium, vanadium, and chromium.

10. The catalyst compound of claim 7, wherein R¹ and R² independently represent a hydrogen atom, or an alkyl radical having 1–6 carbon atoms.

11. The catalyst compound of claim 7, wherein R¹ and R² independently represent a hydrogen atom or a methyl radical.

12. The catalyst compound of claim 7, further comprising a metal alkyl co-catalyst.

13. The catalyst compound of 12, claim wherein said co-catalyst is an alkyl aluminum compound.

14. The catalyst compound of claim 13, wherein said alkyl aluminum compound includes a trialkylaluminum or an aluminoxane.

15. The catalyst compound of claim 14 wherein said aluminoxane is selected from the group consisting of ethyl aluminoxane, isobutyl aluminoxane, and methyl aluminoxane.

16. The catalyst compound of claim 13, wherein said alkyl aluminum compound is trialkylaluminum.

17. A compound useful as a catalyst represented by Formula (I):
wherein

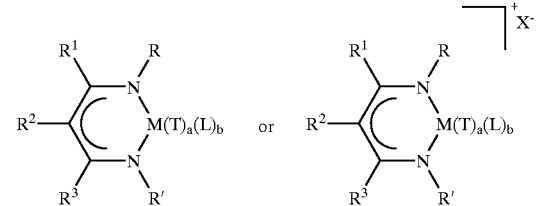

R and R' independently represent 2,6-diisopropylphenyl, 2,6-dimtehylphenyl, 2,6-diethylphenyl, 2,4,6-trimethylphenyl or 2-t-butylphenyl radicals;

R¹, R² and R³ independent represent a hydrogen atom or a substituted or unsubstituted, branched or unbranched hydxocarbyl radical;

M is a group IIIB, IVB, VB, VIB, or VIIB transition metal;

each T independently represent, a hydrogen atom, or a substituted or unsubstituted hydrocarbyl, halogeno, aryloxido, aryorganosilyl, alkylorganosilyl, amido, arylamido, phosphido, or arylphosphido group, or two T groups taken together represent an alkylidene or a cyclometallated hydrocarbyl bidentate ligand;

each L independently repents a sigma donor stabilizing ligand; X, which is optional, represents a relatively weakly coordinated aniom; and a=0 to 4 inclusive, b=0 to 4 inclusive, provided a+b≦4.

18. The compound of claim 17, wherein M is a group IVB, VB, or VIB transition metal.

19. The compound of claim 17, wherein M is selected from the group consisting of titanium, vanadium, and chromium.

20. The compound of claim 17, wherein $R^1$, $R^2$ and $R^3$ represent a hydrogen atom or an alkyl radical having 1–6 carbon atoms.

21. The compound of claim 17, wherein $R^1$, $R^2$ and $R^3$ independently represent a hydrogen atom or methyl radical.

22. The compound of claim 17, wherein $R^3$ represents hydrogen.

23. The compound of claim 22, wherein $R^1$ and $R^2$ each represent a methyl radical.

24. The compound of claim 17, wherein X represents a tetrakis(3,5-bis(trifluoromethyl)phenyl)borate, (phenyl)$_4$B$^-$, ($C_6F_5$)$_4$B$^-$, PF$_6^-$, BF$_4^-$, SbF$_6^-$, triflate or p-tosylate group.

25. The compound of claim 17, wherein X represents a tetrakis(3,5-bis(trifluoromethyl)phenyl)borate, ($C_6F_5$)$_4$B$^-$, PF$_6^-$, BF$_4^-$ or SbF$_6^-$ group.

26. The compound of claim 17, wherein at least one L represents a ligand comprising an oxygen, nitrogen, phosphorus or sulfur atom, said atom having a non-bonded electron pair.

27. The compound of claim 26, wherein said L ligand comprises an ether, amine, phosphine or thioester.

28. The compound of claim 27, wherein said ligand comprises THF or pyridine.

29. The compound of claim 17 wherein at least one T represents a methyl, ethyl, propyl, butyl, amyl, isoamyl, hexyl, iso-butyl, heptyl, octyl, nonyl, decyl, cetyl, 2-ethylhexyl, or phenyl group.

30. The compound of claim 17, wherein at least one T represents a chloro, bromo, fluoro, or iodo group.

31. The compound of claim 17 wherein in at least one T is a chloro group.

32. The compound of claim 17 wherein at least one T represents an alkoxido or an aryloxido group.

33. The compound of claim 17 wherein at least one T independently represents methoxide or ethoxide.

34. The compound of claim 17 wherein a=2.

35. The compound of claim 34, wherein b=2.

36. A compound comprising a group IIIB, IVB, VB, VIB, or VIIB transition metal; and at lease two β-diiminate bidentate ligands, each β-diminate bidentate ligand independently represented by Formula II:

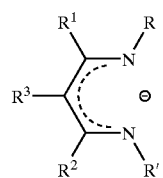

wherein

R and R' independently represent a 2,6-diisopropylphenyl, 2,6-dimetylphenyl, 2,6diethylphenyl, 2,4,6-trimethylphenyl or 2-t-butylpheuyl radical; and $R^1$, $R^2$ and $R^3$ independently represent a hydrogen atom, or a substituted or unsubstituted, branched or unbranched hydrocarbyl radical.

37. The compound of claim 36, wherein each of said at least two β-diiminate bidentate ligands are coordinated to a group IIIB, IVB, VB, VIB, VIIB or VIII transition metal.

38. The compound of claim 37, wherein at least two of said at least two β-diiminate bidentate ligands are coordinated to the same group IIIB, IVB, VB, VIB, VIIB or VIII transition metal.

39. The compound of claims, wherein said compound is a polynuclear metal complex with at least two metal atoms.

40. The compound of claim 36, wherein said compound comprises at least two group IIIB, IVB, VB, VIB, VIIB or VIII transition metal atoms.

41. The compound of claim 36, wherein said compound comprises at least two group IIIB, IVB, VB, VIB, VIIB or VIII transition metal atoms joined by at least one bridging ligand.

42. The compound of claim 41, wherein said at least one bridging ligand independently comprises a hydrogen atom, or a substituted or unsubstituted, branched or unbranched hydrocarbyl, halogeno, aryloxido, arylorganosilyl, alkylorganosilyl, amido, arylamido, phosphido, or arylphosphido group.

43. The compound of claim 36, wherein ad compound is represented by the following formula I(A):

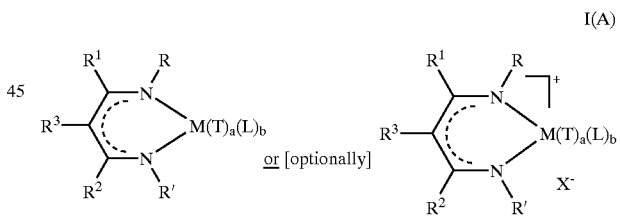

wherein

R and R' independently represent a 2,6-diisopropylphenyl, 2,6-dimethylphenyl, 2,6-diethylphenyl, 2,4,6-trimethylphenyl or 2-t-butylphenyl radical;

$R^1$, $R^2$ and $R^3$ independently represent a hydrogen atom, or a substituted or unsubstituted, branched or unbranched hydrocarbyl radical;

M independently represents a group IIIB, IVB, VB, VIB, VIIB or VIII transition metal;

a=an integer from 1 to 4 inclusive, b=an integer from 1 to 4 inclusive, provided a+b≦4, X$^-$ represents a relatively weakly coordinated anion;

at least one L group together with at least one T group represent a β-diiminate ligand represented by Formula II, if either a or b is greater than 1, additional L groups independently represent a sigma donor stabilizing ligand, and additional T groups independently represent a univalent anionic ligand or, if more than 1 additional T groups are present, two T groups together may form an alkylidene or a cyclometallated hydrocarbyl radical or an additional L group together with an additional T group may represent an additional β-diiminate ligand.

44. The compound of claim 36, wherein said compound is represented by Formula I(B) or comprises a cation represented by Formula I(B), as follows:

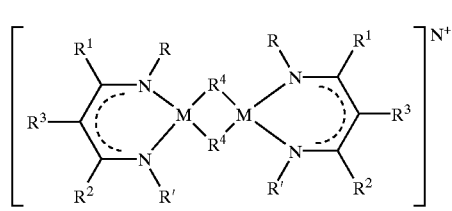

wherein

R and R' independently represent a 2,6-diisopropylphenyl, 2,6-dimethylphenyl, 2,6-diethylphenyl, 2,4,6-trimethylphenyl or 2-t-butylphenyl radical;

$R^1$, $R^2$ and $R^3$ independently represent a hydrogen atom, or a substituted or unsubstituted, branched or unbranched hydrocarbyl radical;

$R^4$ independently represents a bridging ligand;

M independently represents a group IIIB, IVB, VB, VIB, VIIB or VIII transition metal; and N=an integer from 0 to 3.

45. The compound of claim 44, wherein N is 0.

46. The compound of claim 44, wherein at least one of the transition metals is in the 2+ oxidation state.

47. The compound of claim 44, wherein at least one of the transition metals is chromium(II).

48. A catalyst compound useful for the polymerization of olefin monomers, said catalyst compound comprising a transition metal and a monoanionic bidentate ligand represented by Formula (II):

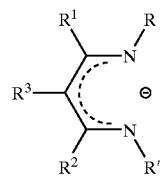

wherein

R and R' independently represent an organosilyl radical and $R^1$, $R^2$ and $R^3$ independently represent a hydrogen atom or a substituted or unsubstituted, branched or unbranched hydrocarbyl radical; and said transition metal is selected from the group consisting of IIIB, IVB, VB, VIB, or VIIB.

49. The catalyst compound of claim 48, wherein R and R' independently represent a radical selected from the group consisting of arylorganosilyl and alkylorganosilyl.

50. The compound of claim 49, wherein said organosilyl radical is an arylorganosilyl radical.

51. A compound useful as a catalyst represented by Formula (I):

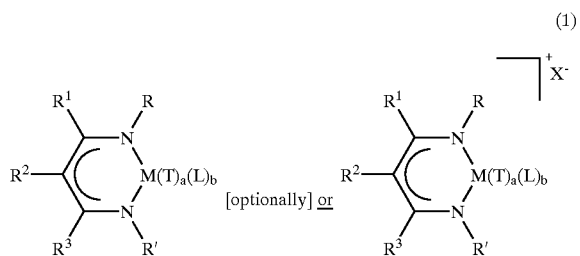

wherein

R and R' independently represent an organosilyl radical; $R^1$, $R^2$ and $R^3$ independently represent a hydrogen atom or a substituted or unsubstituted, branched or unbranched hydrocarbyl radical; and M is a group IIIB, IVB, VB, VIB, or VIIB transition metal;

each T independently represents a univalent anionic ligand selected from a hydrogen atom, or a substituted or unsubstituted hydrocarbyl, halogeno, aryloxido, arylorganosilyl, alkylorganosilyl, amido, arylamido, phosphido, or arylphosphido group, or two T groups taken together represent an alkylidene or a cyclometallated hydrocarbyl bidentate ligand;

each L independently represents a sigma donor stabilizing ligand; X represents a relatively weakly coordinated anion; and a=0 to 4 inclusive, b=0 to 4 inclusive, provided a+b≦4.

* * * * *